United States Patent
Cho et al.

(10) Patent No.: US 8,242,113 B2
(45) Date of Patent: Aug. 14, 2012

(54) OXAZOLIDINONE DERIVATIVES WITH CYCLIC AMIDOXIME OR CYCLIC AMIDRAZONE PHARMACEUTICAL COMPOSITIONS THEREOF

(75) Inventors: Young Lag Cho, Daejeon (KR); Sang Eun Chae, Daejeon (KR); Sung Yoon Baek, Daejeon (KR); Yeon Ok Kim, Daejeon (KR); Seong Jin Kim, Daejeon (KR); Hyang Sook Lee, Daejeon (KR); Ju Hyun Park, Daejeon (KR); Tae Kyo Park, Daejeon (KR); Sung Ho Woo, Daejeon (KR); Yong Zu Kim, Daejeon (KR)

(73) Assignee: Legochem Biosciences, Inc., Deajeon (KR)

( * ) Notice: Subject to any disclaimer, the term of this patent is extended or adjusted under 35 U.S.C. 154(b) by 0 days.

(21) Appl. No.: 13/120,568

(22) PCT Filed: Sep. 22, 2009

(86) PCT No.: PCT/KR2009/005376
§ 371 (c)(1),
(2), (4) Date: Mar. 23, 2011

(87) PCT Pub. No.: WO2010/036000
PCT Pub. Date: Apr. 1, 2010

(65) Prior Publication Data
US 2011/0178293 A1    Jul. 21, 2011

(30) Foreign Application Priority Data

Sep. 24, 2008 (KR) .......................... 10-2008-0093712

(51) Int. Cl.
*C07D 403/08*  (2006.01)
*A61K 31/5377* (2006.01)

(52) U.S. Cl. ...................... 514/229.2; 514/241; 514/242; 544/66; 544/180; 544/182

(58) Field of Classification Search ................... 544/66, 544/180, 182; 514/229.2, 241, 242
See application file for complete search history.

(56) References Cited

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Banker, G.S. et al, "Modern Pharmaceutices, 3ed." Marcel Dekker, New York, 1996, pp. 451 and 596.*

* cited by examiner

*Primary Examiner* — Kahsay T Habte
(74) *Attorney, Agent, or Firm* — Hyunsuk Min; SIMI Law Group, P.C.

(57) ABSTRACT

Disclosed is a novel oxazolidinone derivative, particularly a novel oxazolidinone compound with a cyclic amidoxime or cyclic amidrazone group. Also disclosed is a pharmaceutical antibiotic composition including a novel oxazolidinone derivative, in vivo hydrolysable ester thereof, in vivo hydrolysable phosphate ester thereof, an isomer thereof or a pharmaceutically acceptable salt thereof as an effective ingredient. Because the novel oxazolidinone derivative, in vivo hydrolysable ester thereof, in vivo hydrolysable phosphate ester thereof, an isomer thereof or a pharmaceutically acceptable salt thereof exhibits a wide antibacterial spectrum against resistant bacteria, a low toxicity, and a strong antibacterial activity against Gram-positive and Gram-negative bacteria, it can be usefully used as an antibiotic.

22 Claims, No Drawings

OXAZOLIDINONE DERIVATIVES WITH CYCLIC AMIDOXIME OR CYCLIC AMIDRAZONE PHARMACEUTICAL COMPOSITIONS THEREOF

TECHNICAL FIELD

The present invention relates to novel oxazolidinone derivatives represented by Chemical Formula 1, particularly to novel oxazolidinone derivatives having a cyclic amidoxime or a cyclic amidrazone group.

[Chemical Formula 1]

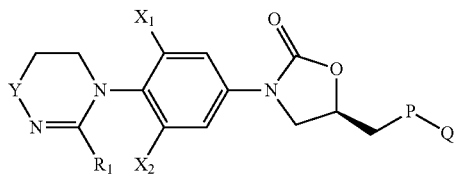

The present invention also relates to pharmaceutical antibiotic compositions including novel oxazolidinone derivatives represented by Chemical Formula 1, prodrugs thereof, hydrates thereof, solvates thereof, isomers thereof or pharmaceutically acceptable salts thereof as an effective ingredient.

BACKGROUND ART

Ever since the discovery of penicillin, numerous antibiotics have been developed by the pharmaceutical companies worldwide, including β-lactam antibiotics against bacterial infections, sulfonamides, tetracyclines, aminoglycosides, macrolides, quinolones, glycopeptides, and the like. And yet, new antibiotic resistant bacteria or multidrug resistant bacteria are incessantly occurring because of misuse or abuse of antibiotics. Due to this, concerns are increasing worldwide. The international microbiological community concerns that, with the evolution of antibiotic resistance, new resistant bacteria that are not affected by any currently used antibiotics might be rampant in near future.

In general, bacterial pathogens can be classified into Gram-positive or Gram-negative bacteria. In particular, Gram-positive bacteria, e.g. *Staphylococcus, Enterococcus, Streptococcus* and acid-fast bacteria, are very important. It is because, once occurring in a hospital environment, they are difficult to be eradicated and tend to develop into intractable resistant bacteria. Such resistant bacteria include methicillin-resistant *Staphylococcus* (MRSA), methicillin-resistant coagulase-negative *Staphylococcus* (MRCNS), penicillin-resistant *Streptococcus pneumoniae*, multiple-resistant *Enterococcus faecium*, or the like.

For the clinically effective treatment of the Gram-positive bacteria, vanomycin, a glycopeptide antibiotic, is often used. However, vancomycin is related with a variety of toxicities and, since the emergence of vancomycin-resistant *Enterococcus* (VRE) in 1990s, bacteria resistant to vancomycin and other glycopeptide-based antibiotics are emerging.

And, for antibiotics such as β-lactam, quinolone and macrolide used to treat infections of the upper respiratory tract caused by specific Gram-negative bacteria including *Haemophilus influenzae* (*H. influenzae*) and *Moraxella catarrhalis* (*M. catarrhalis*), resistant bacteria like quinoline-resistant *Staphylococcus aureus* (QRSA) are emerging. Hence, researches on new antibiotics are under way.

Accordingly, in order to fundamentally solve the antibiotic resistance problem, development of antibiotics with new chemical structure and antibacterial mechanism is urgent. In this respect, since an oxazolidinone antibiotic with a new chemical structure was first reported in 1984 by DuPont (European Paten Publication No. 127,902), a variety of oxazolidinone derivatives have been designed and synthesized by many pharmaceutical companies.

Those oxazolidinone derivatives are new synthetic antibiotics and might be administered orally. The oxazolidinone antibiotics have a totally different chemical backbone from the classical antibiotics. Since they inhibit the initial stage of protein synthesis, they exhibit superior antibacterial activity against antibiotic-resistant bacteria, particularly Gram-positive bacteria, such as methicillin-resistant *Staphylococcus aureus* (MRSA), methicillin-resistant *Staphylococcus epidermidis* (MRSE), quinolone-resistant *Staphylococcus aureus* (QRSA), vancomycin-resistant *Enterococcus* (VRE) and multidrug-resistant *Mycobacterium tuberculosis* (MDRTB).

As examples of oxazolidinone compounds including an oxazolidinone ring, 3-phenyl-2-oxazolidinone derivatives having one or two substituent(s) are described in U.S. Pat. Nos. 4,948,801, 4,461,773, 4,340,606, 4,476,136, 4,250,318 and 4,128,654, and 3-[(mono-substituted)phenyl]-2-oxazolidinone derivatives represented by Chemical Formula A are described in EP 0312000, *J. Med. Chem.* 32, 1673(1989), *J. Med. Chem.* 33, 2569 (1990), *Tetrahedron Lett.* 45,123(1989), and the like.

[Chemical Formula A]

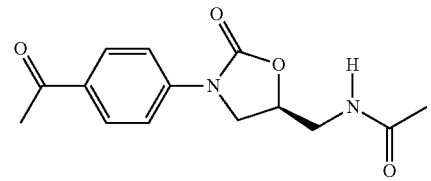

And, oxazolidinone derivatives represented by Chemical Formula B and Chemical Formula C were synthesized by Pharmacia & Upjohn (WO 93/23384, WO 95/14684 and WO 95/07271). The compound of Chemical Formula B, "linezolid", is the first oxazolidinone antibiotic and is marketed under the trade name "zyvox" for oral administration and injection, approved by the U.S. Food and Drug Administration (FDA). However, most of synthetic oxazolidinone compounds are associated with some limitations, such as toxicity, low in vivo efficacy and low solubility. As for linezolid, solubility in water is only about 3 mg/mL, which causes its use as injection limited.

[Chemical Formula B]

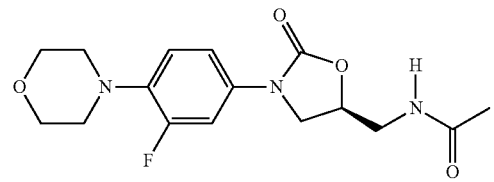

-continued

[Chemical Formula C]

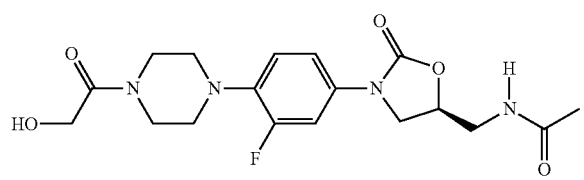

WO 93/09103 discloses phenyl oxazolidinone derivatives having a heterocyclic ring, including pyridine, thiazole, indole, oxazole, quinol, etc., at the 4-position of the phenyl group. But, the substituents of the heterocyclic ring are merely simple alkyl or amino group, and the activities are not so excellent.

In order to solve these problems, WO 01/94342 discloses phenyloxazolidinone derivatives having various pyridine or phenyl derivatives at the 4-position of the phenyl group. The synthetic compounds have wide antibacterial spectrum and excellent antibacterial activity. Although the oxazolidinone compounds having various pyridine derivatives at the 4-position of the phenyl group of oxazolidinone have wider antibacterial spectrum and excellent antibacterial activity as compared to linezolid, most of them have aqueous solubility of 30 μg/mL or less, and thus have limitation in preparing injections.

TR-700 and TR-701, represented by Chemical Formula D, are developed by Dong-A Pharmaceutical and recently licensed to Trius Therapeutics. TR-701 is a prodrug of TR-700 and it is in the phase II clinical trial. TR-701 solves the solubility problem via formation of prodrug from TR-700, exhibits an antibacterial activity superior to that of linezolid. However, the compound shows higher toxicities (cytotoxicity, MAO profile, myelosuppression, etc.) than linezolid, and, thus, is expected to have many limitations.

[Chemical Formula D]

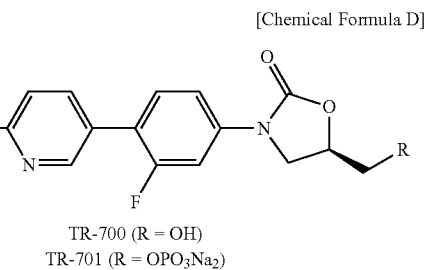

TR-700 (R = OH)
TR-701 (R = OPO$_3$Na$_2$)

As described above, a compound having superior antibacterial activity, satisfactory solubility and lower toxicity is yet to be found.

DISCLOSURE OF INVENTION

Technical Problem

The inventors of the present invention have synthesized novel oxazolidinone derivatives in order to develop antibiotics having superior antibacterial activity as compared to existing antibiotics and having higher solubility for easier preparation into oral administration and injection formulations. The novel oxazolidinone derivatives according to the present invention have been confirmed to have superior antibacterial activity and significantly improved antibacterial spectrum.

Especially, the cyclic amidoxime or cyclic amidrazone compound presented by the present invention has not been studied before. Whereas acyclic amidoxime or amidrazone is relatively well known, the cyclic amidoxime or cyclic amidrazone compound like those disclosed in the present invention is hardly known. Introduction of the cyclic form results in remarkably improved absorptivity and allows the formation of a salt having an adequate basicity, thereby greatly increasing solubility in water. The increased solubility in water makes it possible to prepare injections without using a prodrug and with little toxicity.

Accordingly, an object of the present invention is to provide novel oxazolidinone derivatives, particularly novel oxazolidinone compounds with a cyclic amidoxime or a cyclic amidrazone group so as to improve solubility, and methods for preparing the same.

Another object of the present invention is to provide pharmaceutical antibiotic compositions including novel oxazolidinone derivatives, prodrugs thereof, hydrates thereof, solvates thereof, isomers thereof, or pharmaceutically acceptable salts thereof as an effective ingredient.

The novel oxazolidinone derivatives according to the present invention can be used for treatment of hospital-acquired pneumonia, socially acquired pneumonia, complicated skin and skin structure infections, uncomplicated skin and skin structure infections, or infections caused by antibiotic resistance bacteria, particularly septicemia caused by vancomycin-resistant *Enterococcus faecium* (VRE) or linezolid-resistant *Enterococcus faecalis*, or for combination therapy for Gram-negative bacteria-associated diseases.

Solution to Problem

Hereinafter, the embodiments of the present invention will be described in detail.

The present invention relates to novel oxazolidinone derivatives represented by Chemical Formula 1, particularly novel oxazolidinone compounds with a cyclic amidoxime or a cyclic amidrazone group. The present invention also relates to pharmaceutical antibiotic compositions comprising a novel oxazolidinone derivative represented by Chemical Formula 1, a prodrug thereof, a hydrate thereof, a solvate thereof, an isomer thereof, or a pharmaceutically acceptable salt thereof as an effective ingredient.

[Chemical Formula 1]

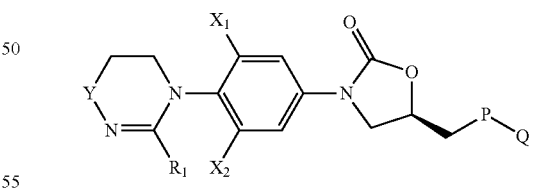

In Chemical Formula 1,
R$_1$ represents hydrogen, (C$_1$-C$_6$)alkyl or (C$_3$-C$_6$)cycloalkyl;
Y represents —O— or —N(R$_2$)—;
R$_2$ represents hydrogen, cyano, (C$_1$-C$_6$)alkyl, (C$_3$-C$_6$)cycloalkyl, —(CH$_2$)$_m$OC(=O)R$_{11}$, —(CH$_2$)$_m$C(=O)$_{12}$, —(CH$_2$)$_m$C(=S)$_{12}$, or —SO$_2$R$_{13}$, wherein the alkyl of R$_2$ may be further substituted by one or more substituent(s) selected from a group consisting of (C$_2$-C$_6$)alkenyl, (C$_2$-C$_6$)alkynyl, halogen, halo(C$_1$-C$_6$)alkyl, (C$_1$-C$_6$)alkyl(C$_2$-C$_6$)alkynyl, hydroxyl, (C$_3$-C$_6$)cycloalkyl and cyano;

$R_{11}$ through $R_{13}$ independently represent hydrogen, $(C_1-C_6)$alkyl, $(C_1-C_6)$alkoxy, amino, $(C_3-C_6)$cycloalkyl, $(C_2-C_6)$alkenyl, $(C_2-C_6)$alkynyl, or $(C_1-C_6)$alkylcarbonyl, wherein the alkyl, alkoxy, or amino of $R_{11}$ through $R_{13}$ may be further substituted by one or more substituent(s) selected from halogen, amino, hydroxyl, cyano, $(C_1-C_6)$alkyl, $(C_1-C_6)$alkylcarbonyloxy and hydroxy$(C_1-C_6)$alkyl;

m represents an integer from 0 to 2;

$X_1$ and $X_2$ independently represent hydrogen or fluorine;

P represents —O—, —NH—, or a five-membered aromatic heterocycle with the following structure

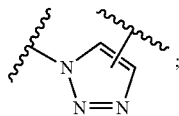

Q represents hydrogen, —C(=O)$R_3$, —C(=S)$R_4$, —C(=O)N$R_5R_6$, —C(=S)N$R_5R_6$, or a five-membered aromatic heterocycle with a structure selected from the followings:

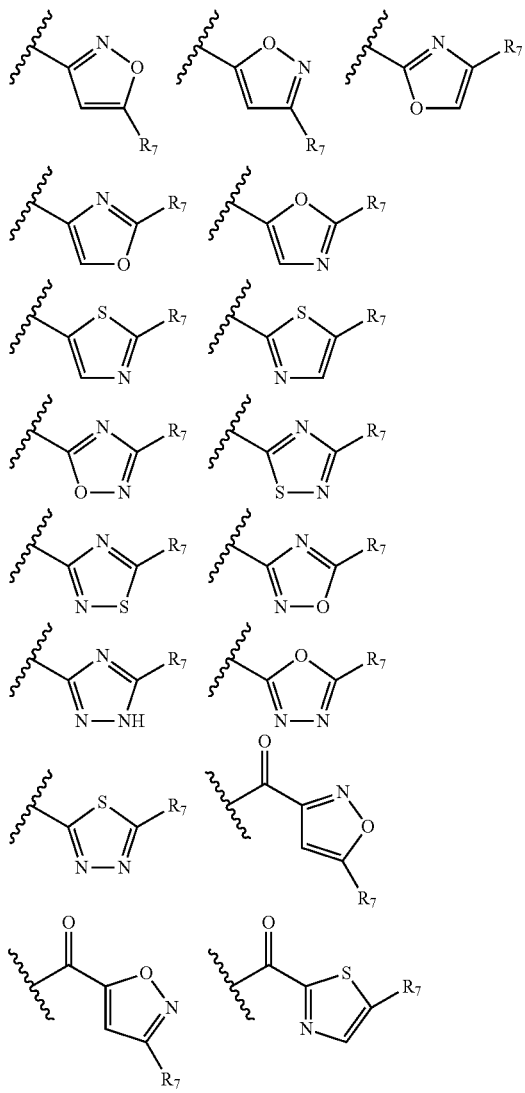

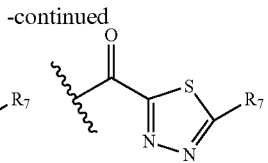

$R_3$ and $R_4$ independently represent hydrogen, $(C_1-C_6)$alkyl, $(C_1-C_6)$alkoxy, $(C_3-C_6)$cycloalkyl, $(C_2-C_6)$alkenyl, or $(C_2-C_6)$alkynyl;

$R_5$ and $R_6$ independently represent hydrogen, $(C_1-C_6)$alkyl, $(C_3-C_6)$cycloalkyl or $(C_2-C_6)$alkenyl;

$R_7$ represents hydrogen, halogen, $(C_1-C_6)$alkyl, or $(C_3-C_6)$cycloalkyl; and the alkyl of $R_3$ through $R_7$ may be further substituted by one or more substituent(s) selected from a group consisting of hydroxyl, cyano, halogen, $(C_1-C_6)$alkylcarbonyloxy and amino.

As used herein, the term 'alkyl' includes linear and branched structures. For example, the term "$(C_1-C_6)$alkyl" includes all possible positional and geometrical isomers, such as methyl, ethyl, propyl, isopropyl, butyl, isobutyl, tert-butyl, pentyl, hexyl, and the like.

The term "$(C_3-C_6)$cycloalkyl" includes all possible positional and geometrical isomers, such as cyclopropyl, cyclobutyl, cyclopentyl, cyclohexyl, cyclopropylmethyl, and the like.

The term "$(C_2-C_6)$alkenyl" includes all possible positional and geometrical isomers, such as vinyl, propenyl, 1- and 2-butenyl, pentenyl, and the like.

The term "$(C_2-C_6)$alkynyl" includes all possible positional and geometrical isomers, such as acetylenyl, propargyl, 1-propynyl, 2-pentynyl, and the like.

The oxazolidinone derivatives according to the present invention can be represented by Chemical Formula 2 or 3:

[Chemical Formula 2]

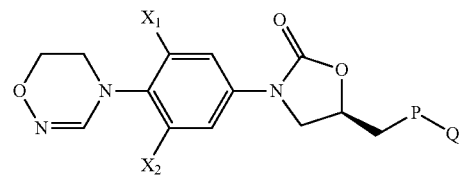

[Chemical Formula 3]

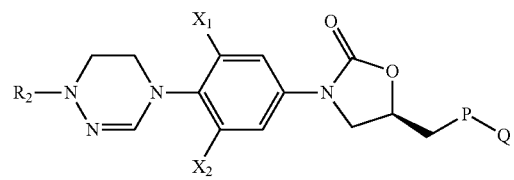

In Chemical Formulas 2 and 3, $R_2$, $X_1$, $X_2$, P and Q are the same as defined in Chemical Formula 1.

More preferably, the oxazolidinone derivatives according to the present invention include the compounds represented by Chemical Formulas 4 to 9:

[Chemical Formula 4]

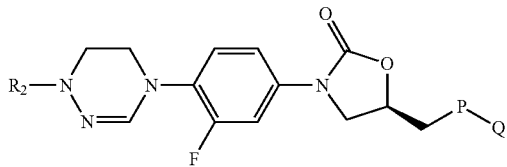

[Chemical Formula 5]

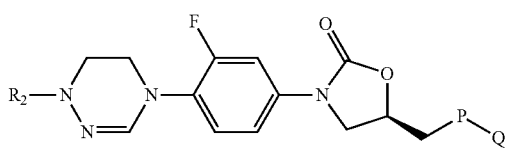

[Chemical Formula 6]

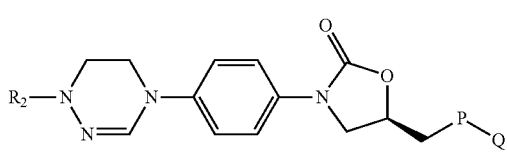

[Chemical Formula 7]

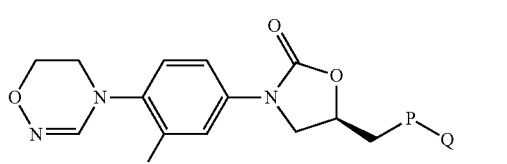

[Chemical Formula 8]

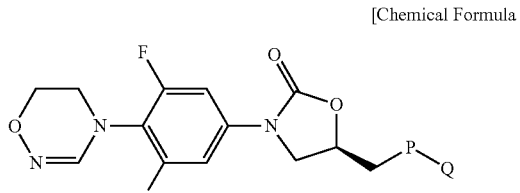

[Chemical Formula 9]

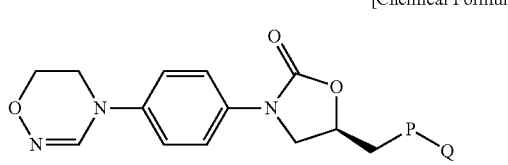

In Chemical Formulas 4 to 9, $R_2$ represents hydrogen, cyano, $(C_1-C_6)$alkyl, $(C_3-C_6)$cycloalkyl, $-(CH_2)_mOC(=O)R_{11}$, $-(CH_2)_mC(=O)R_{12}$, $-(CH_2)_mC(=S)_{12}$, or $-SO_2R_{13}$, wherein the alkyl of $R_2$ may be further substituted by one or more substituent(s) selected from a group consisting of $(C_2-C_6)$alkenyl, $(C_2-C_6)$alkynyl, halogen, halo$(C_1-C_6)$alkyl, $(C_1-C_6)$alkyl$(C_2-C_6)$alkynyl, hydroxyl, $(C_3-C_6)$cycloalkyl and cyano;

$R_{11}$ through $R_{13}$ independently represent hydrogen, $(C_1-C_6)$alkyl, $(C_1-C_6)$alkoxy, amino, $(C_3-C_6)$cycloalkyl, or $(C_1-C_6)$alkylcarbonyl, wherein the alkyl, alkoxy or amino of $R_{11}$ through $R_{13}$ may be further substituted by one or more substituent(s) selected from halogen, amino, hydroxyl, cyano, $(C_1-C_6)$alkyl, $(C_1-C_6)$alkylcarbonyloxy and hydroxy$(C_1-C_6)$alkyl;

m represents an integer from 0 to 2;

P represents —O—, —NH— or a five-membered aromatic heterocycle with the following structure

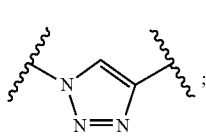

Q represents hydrogen, —C(=O)R$_3$, —C(=S)R$_4$, —C(=O)NR$_5$R$_6$, —C(=S)NR$_5$R$_6$, or a five-membered aromatic heterocycle with a structure selected from the followings

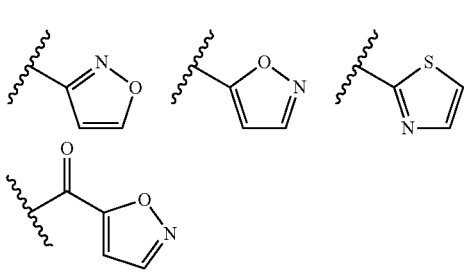

$R_3$ and $R_4$ independently represent hydrogen, $(C_1-C_6)$alkyl or $(C_1-C_6)$alkoxy;

$R_5$ and $R_6$ independently represent hydrogen or $(C_1-C_6)$alkyl; and the alkyl of $R_3$ through $R_6$ may be further substituted by one or more substituent(s) selected from a group consisting of hydroxyl, cyano, halogen, $(C_1-C_6)$alkylcarbonyloxy and amino.

Examples of the novel oxazolidinone derivatives according to the present invention include the following compounds, but the scope of the present invention is not limited to them:

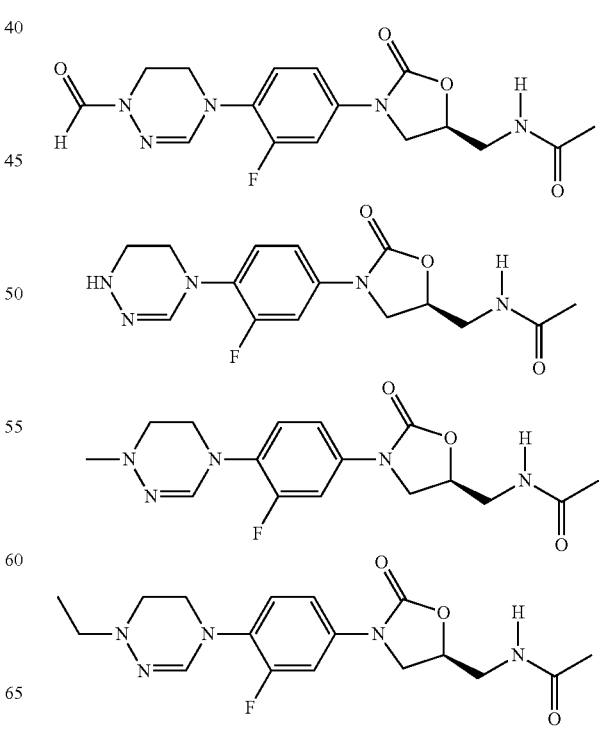

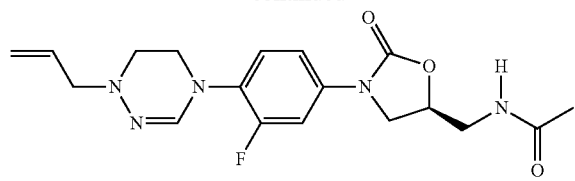
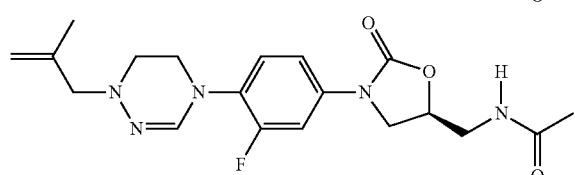
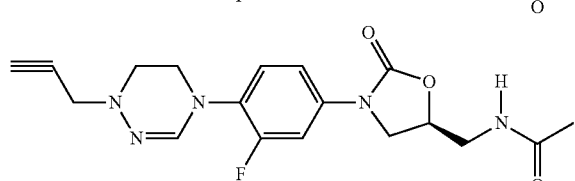
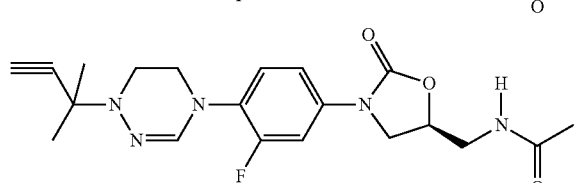
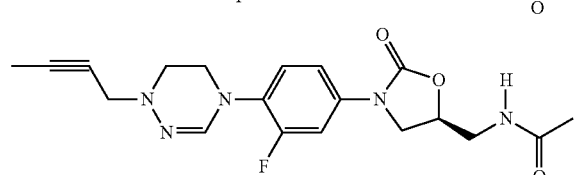
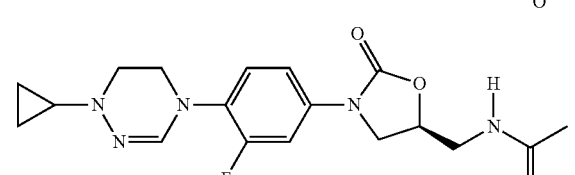
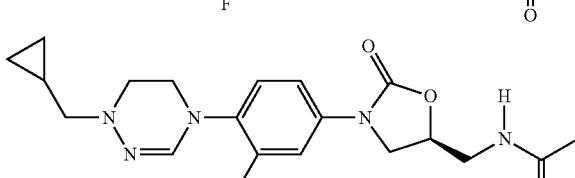
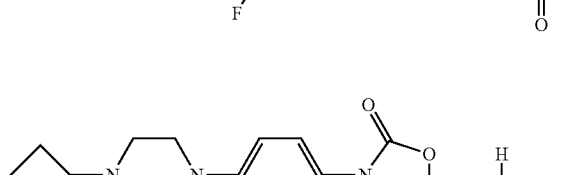
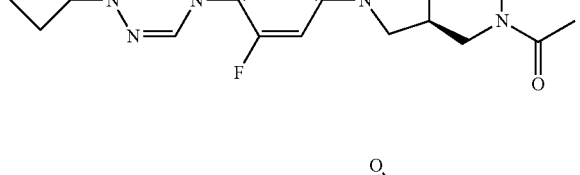
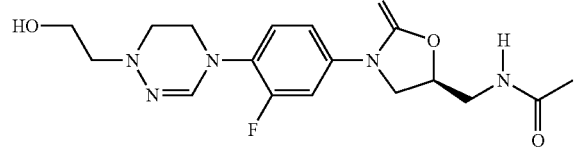
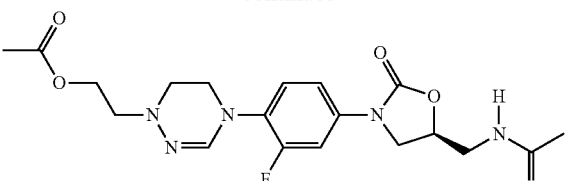
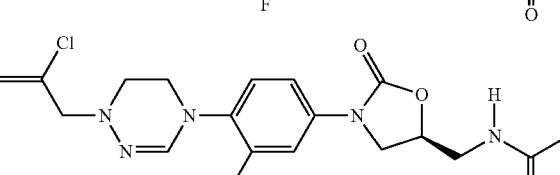
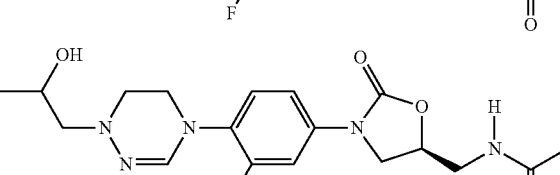
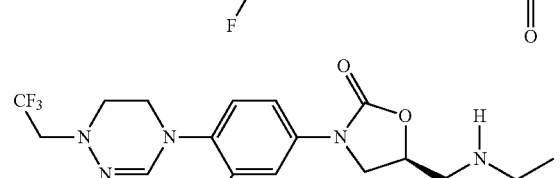
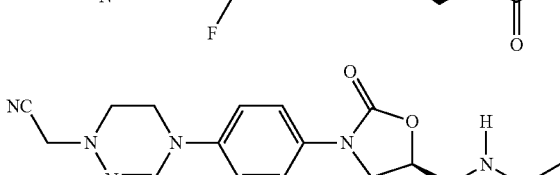
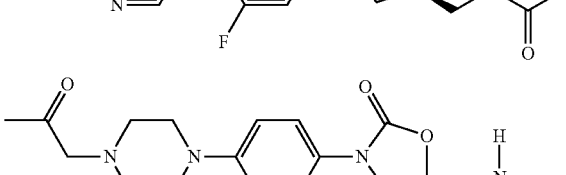
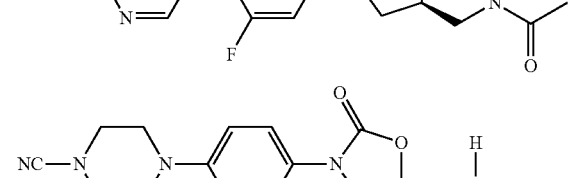
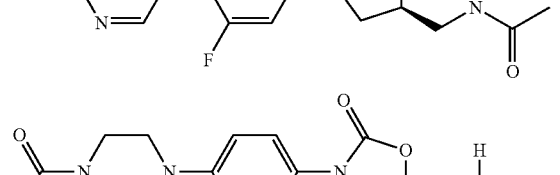
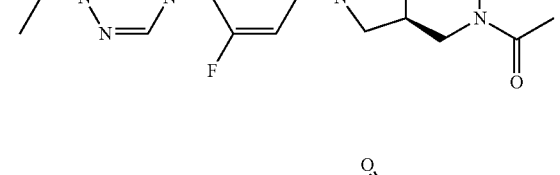
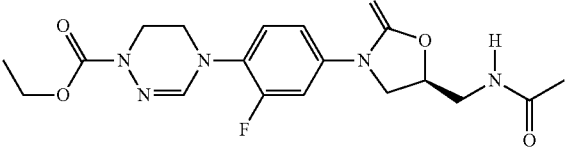

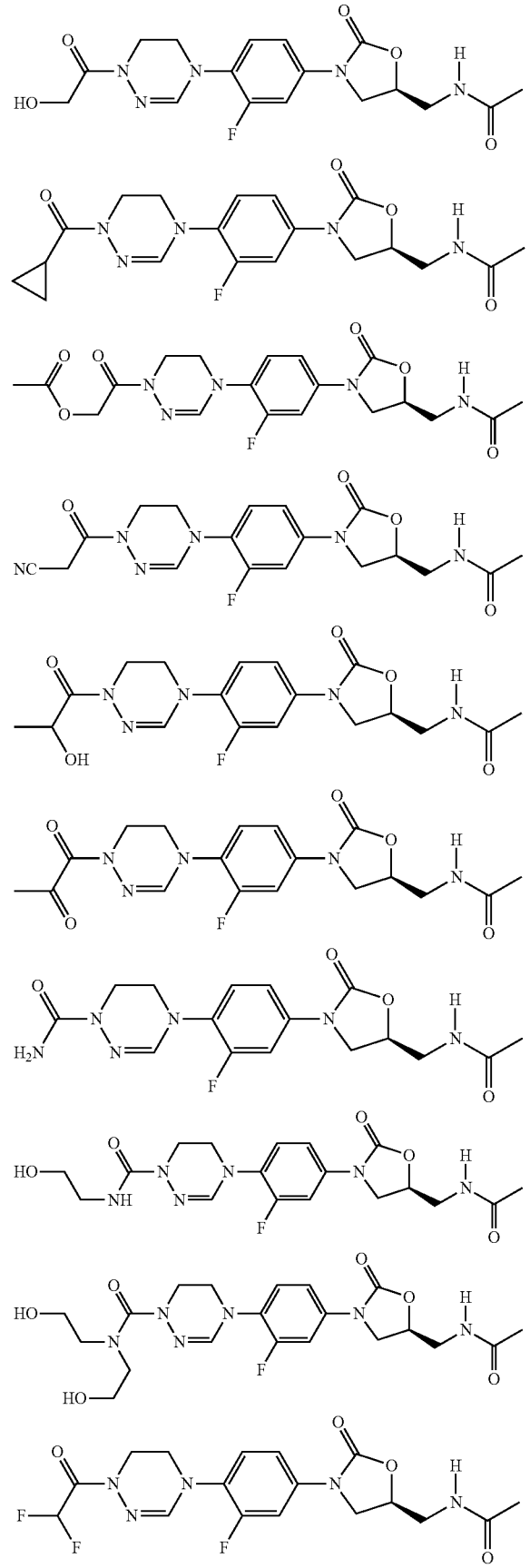
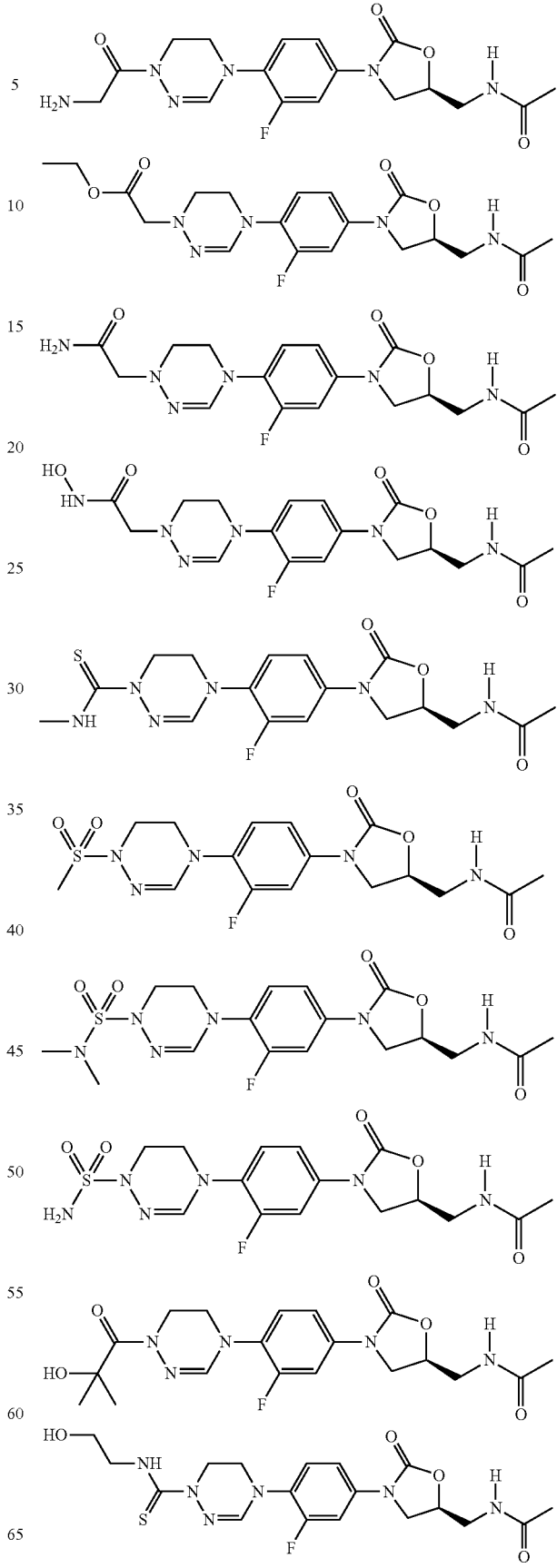

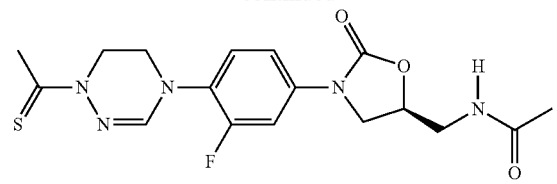
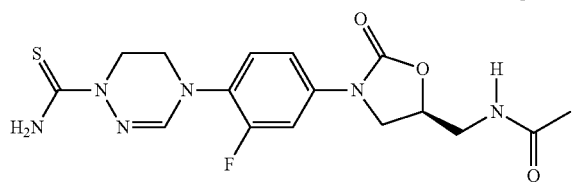
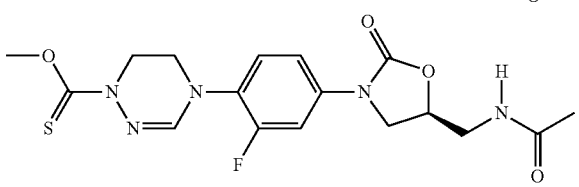
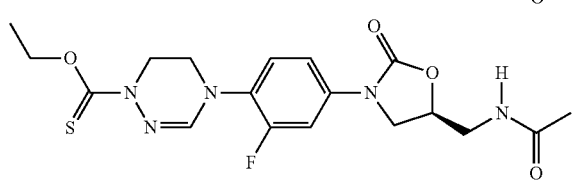
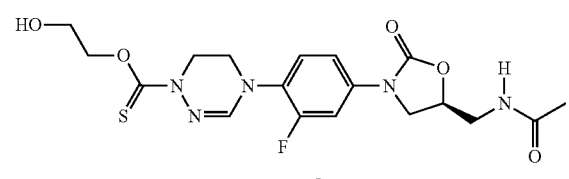
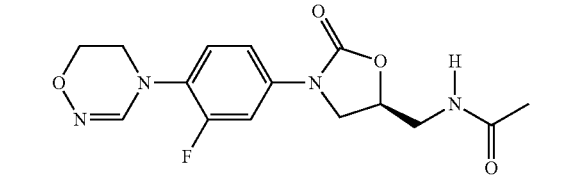
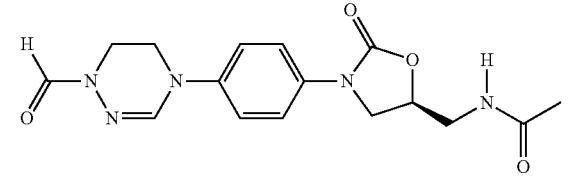
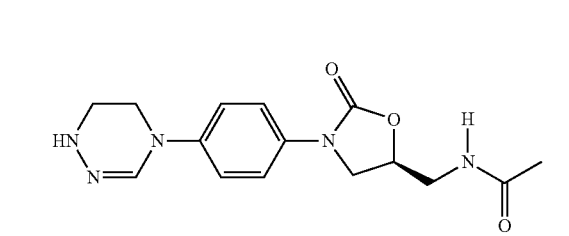
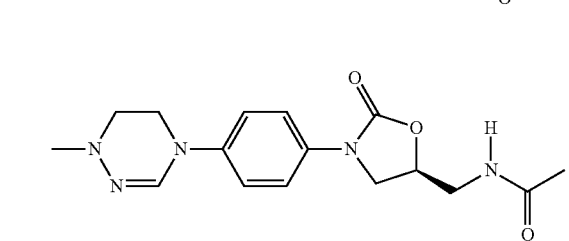
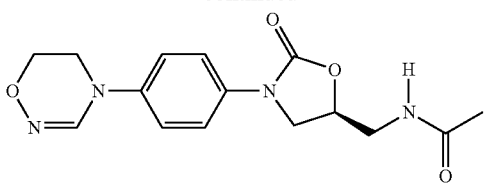
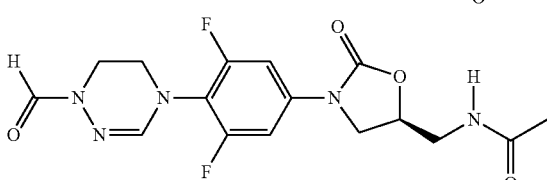
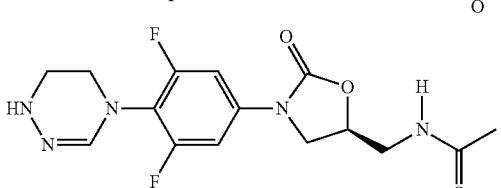
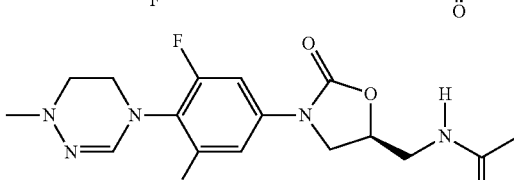
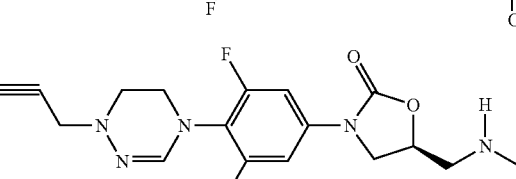
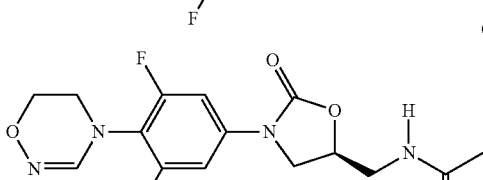
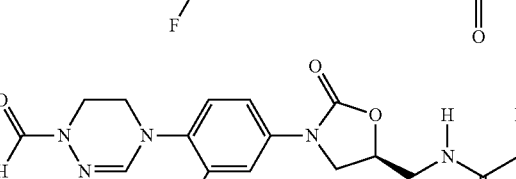
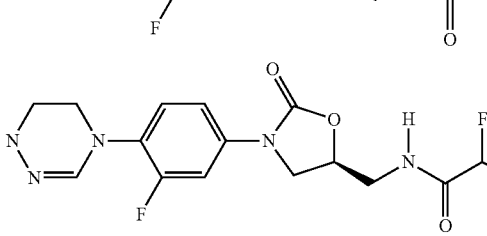
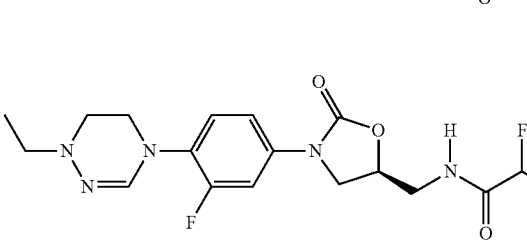

15
-continued
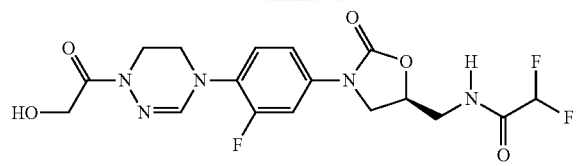
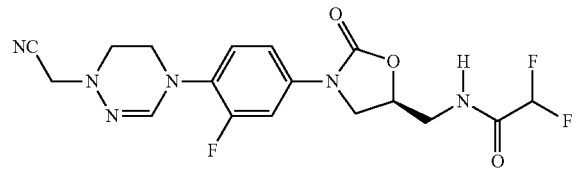
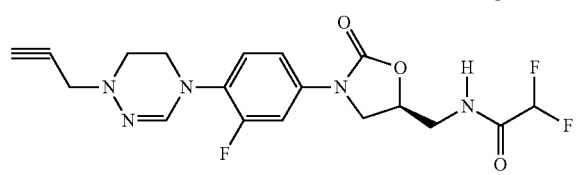
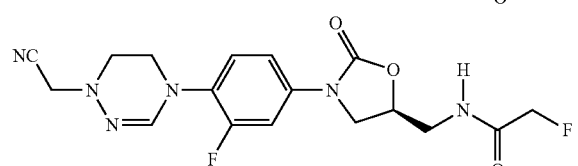
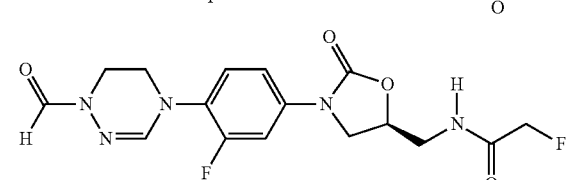
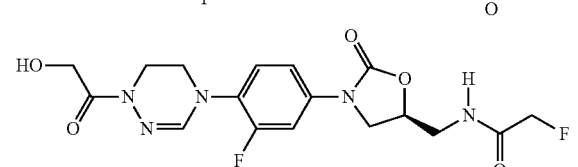
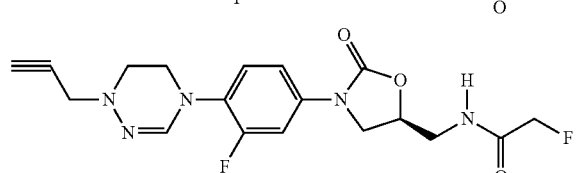
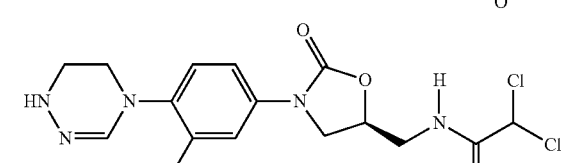
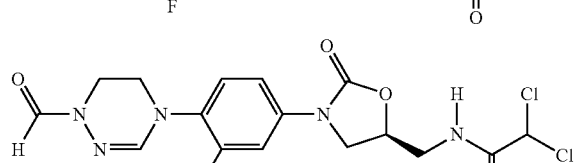
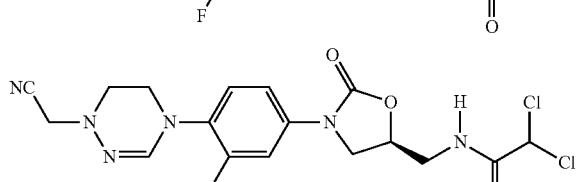
16
-continued
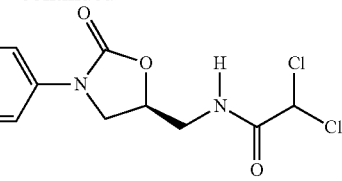
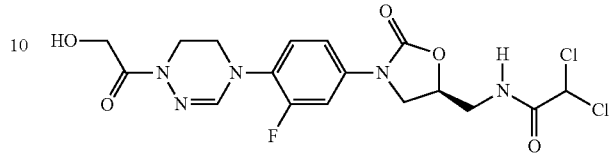
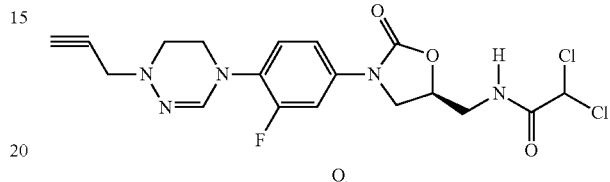
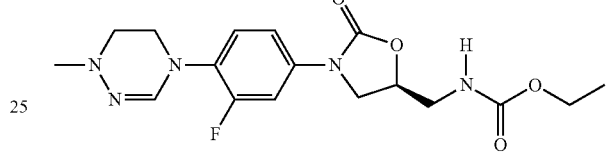
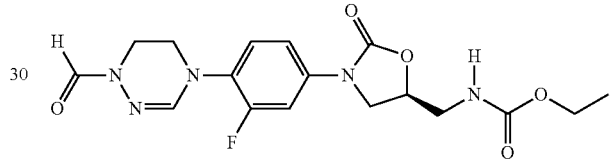
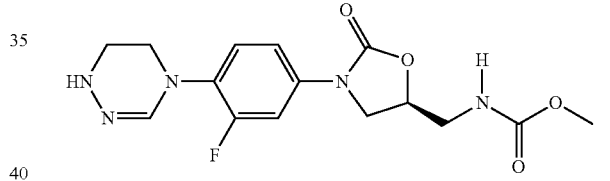
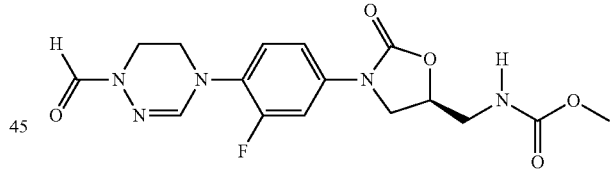
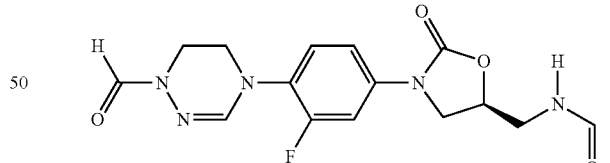
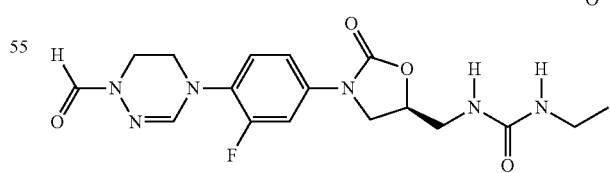
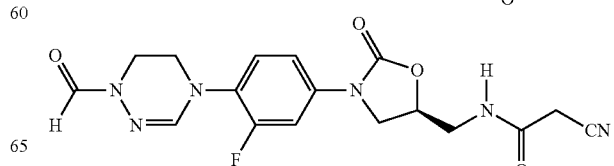

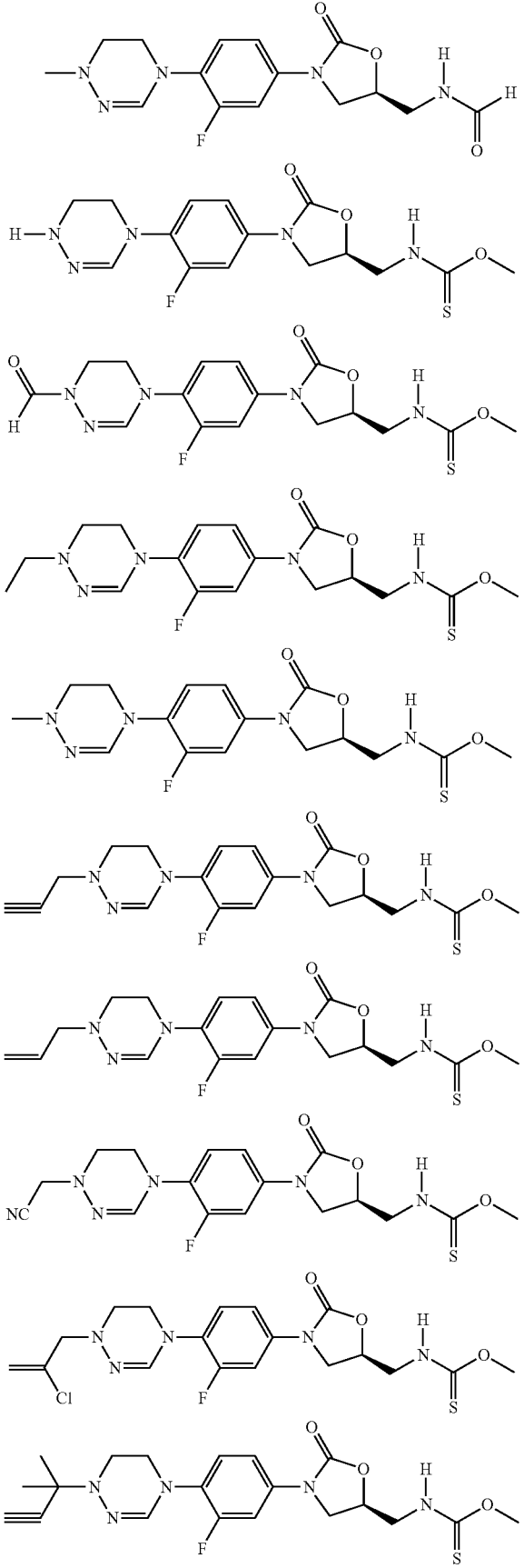
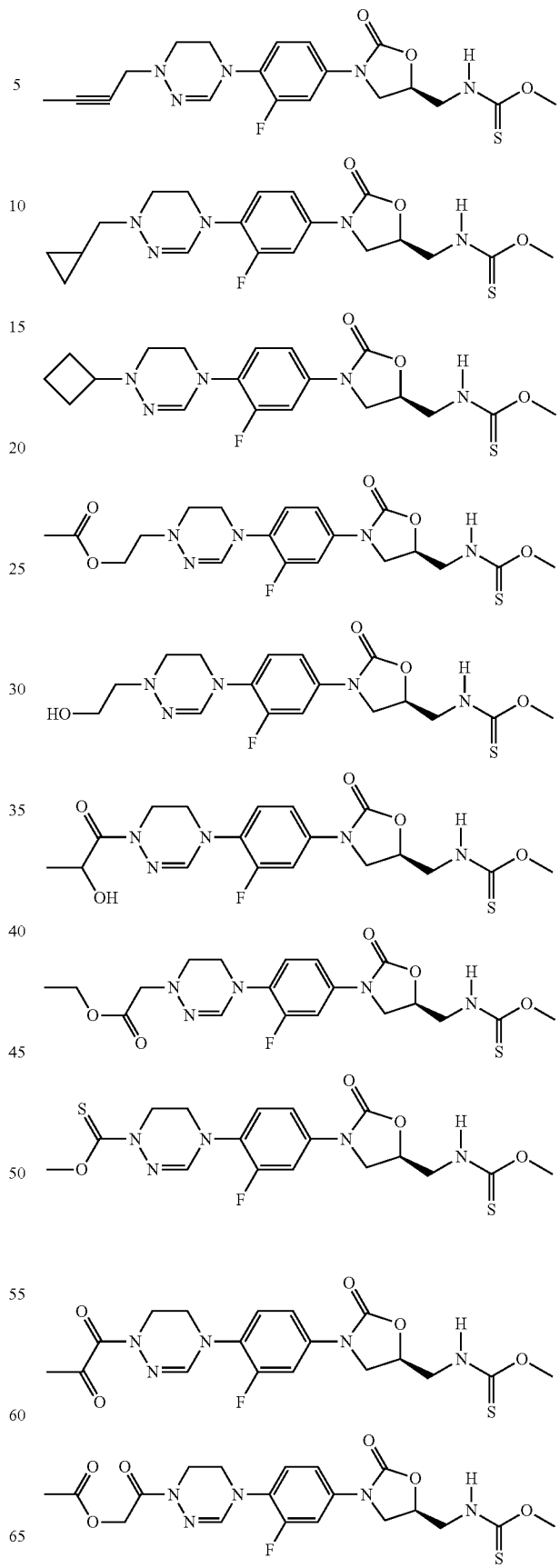

-continued
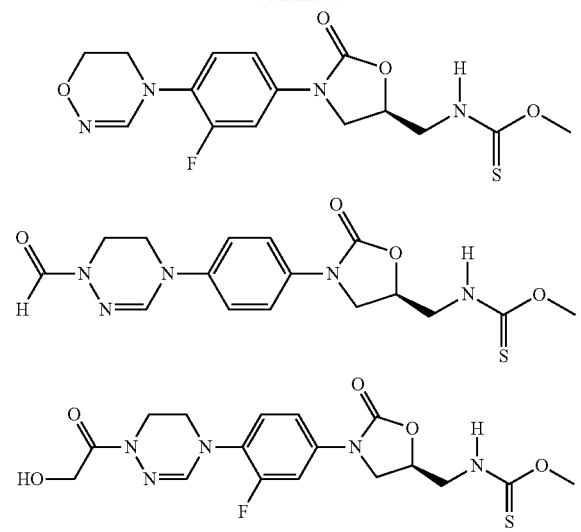
-continued
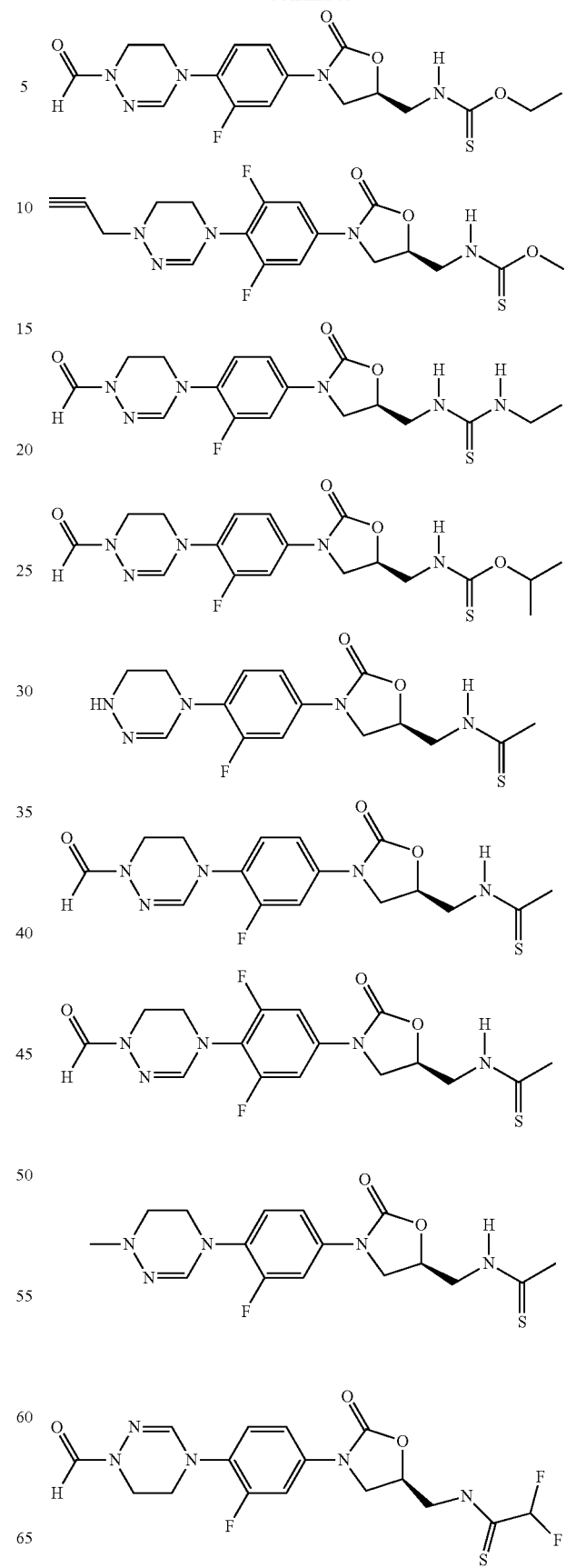

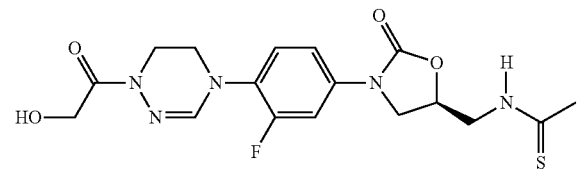
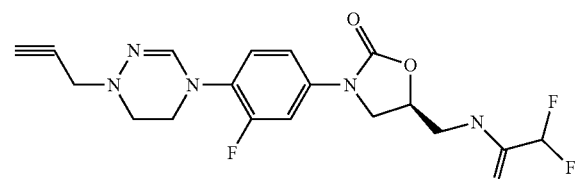
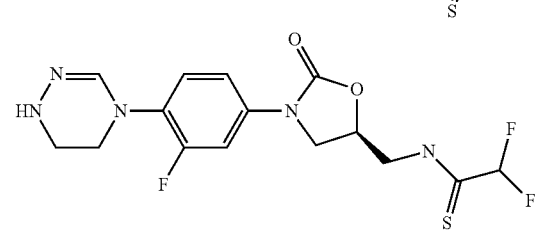
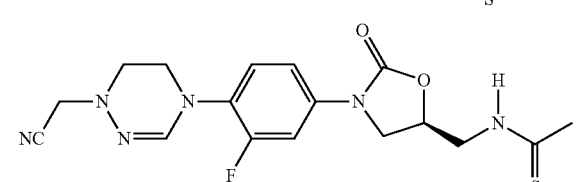
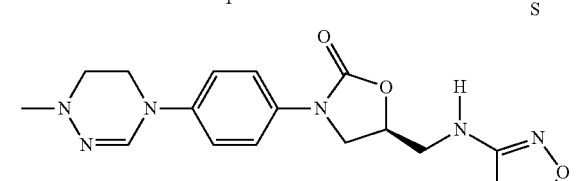
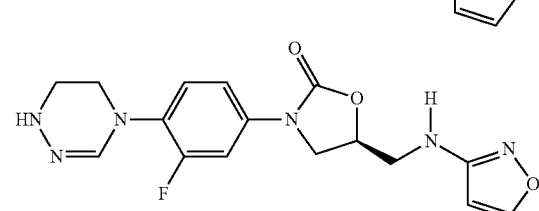
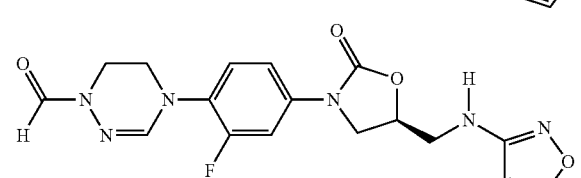
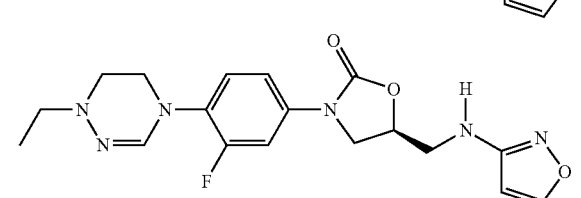
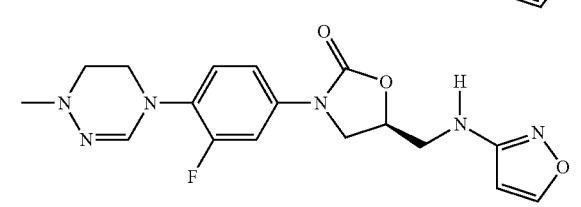
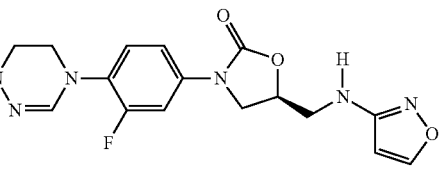
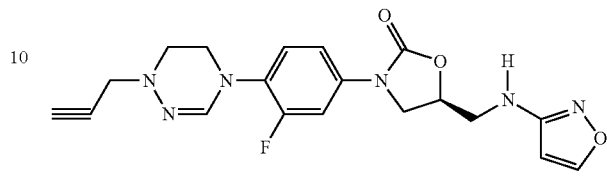
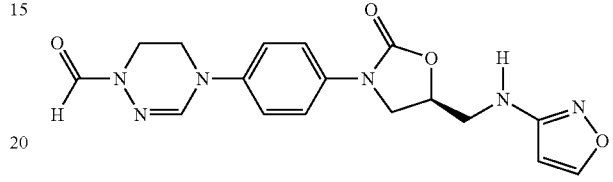
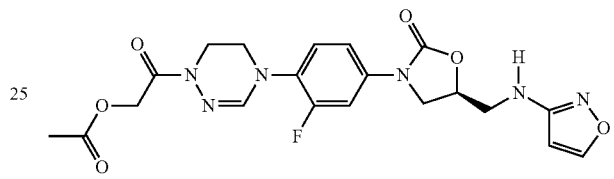
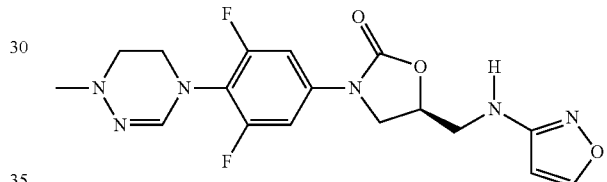
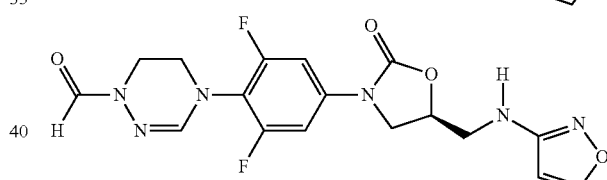
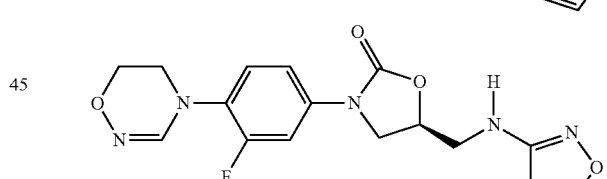
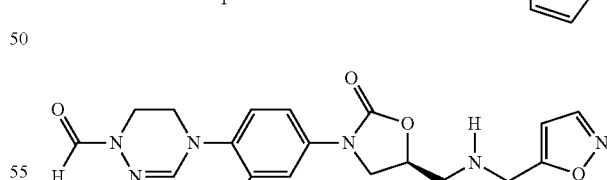
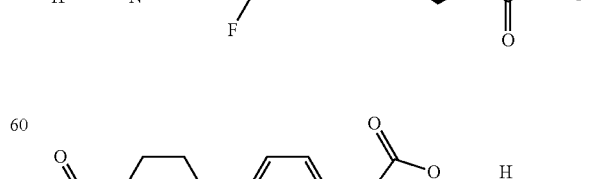
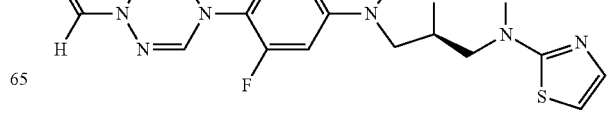

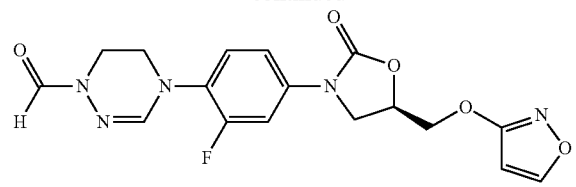
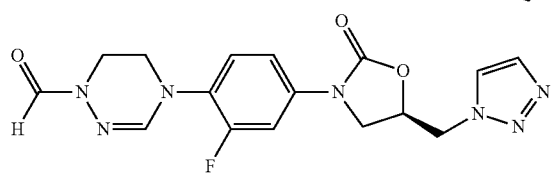
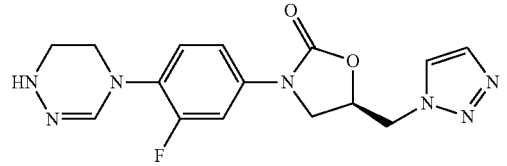
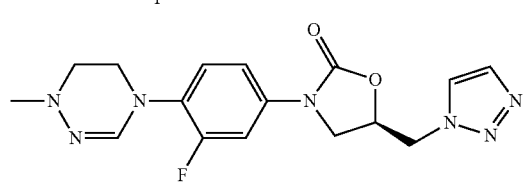
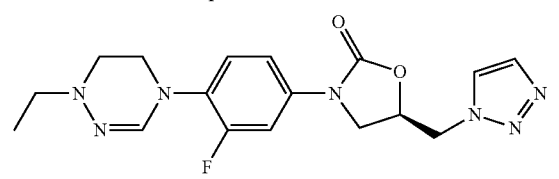
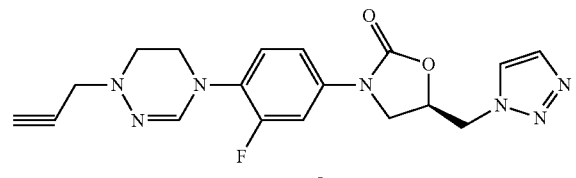
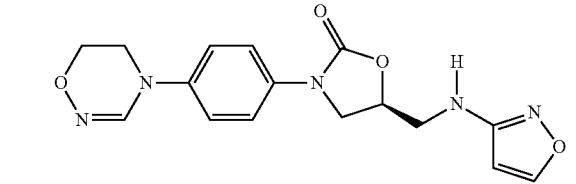
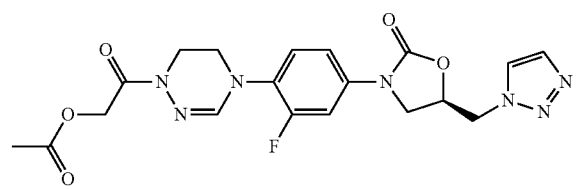
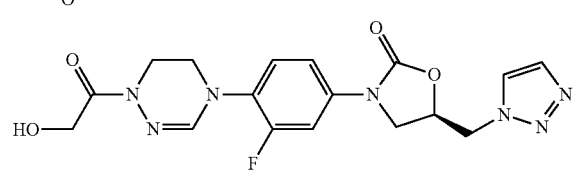
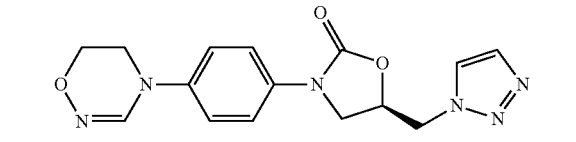
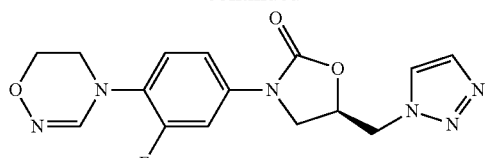
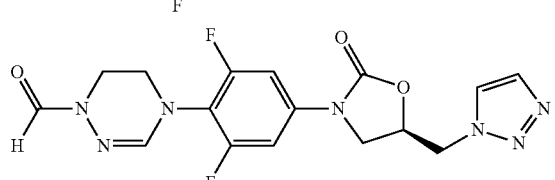
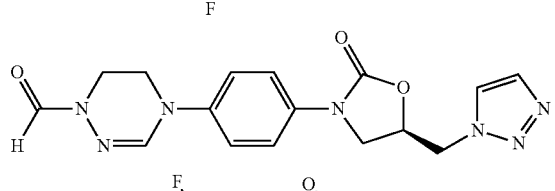
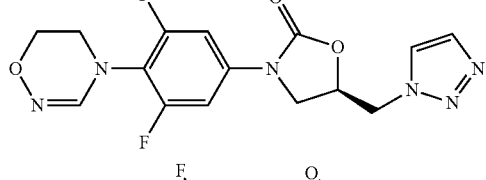
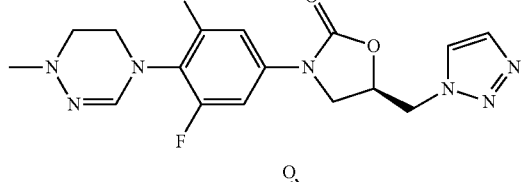
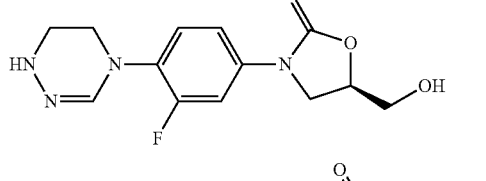
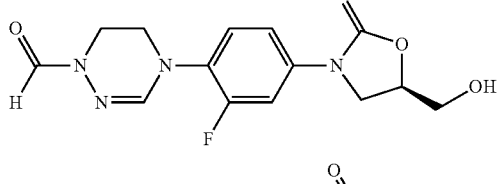
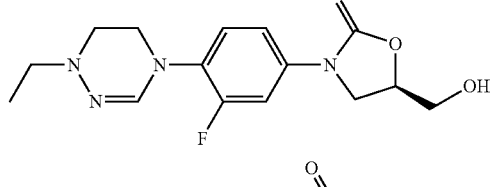
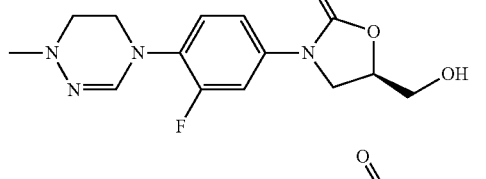
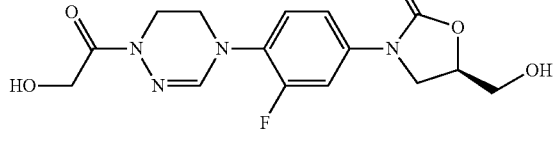

-continued

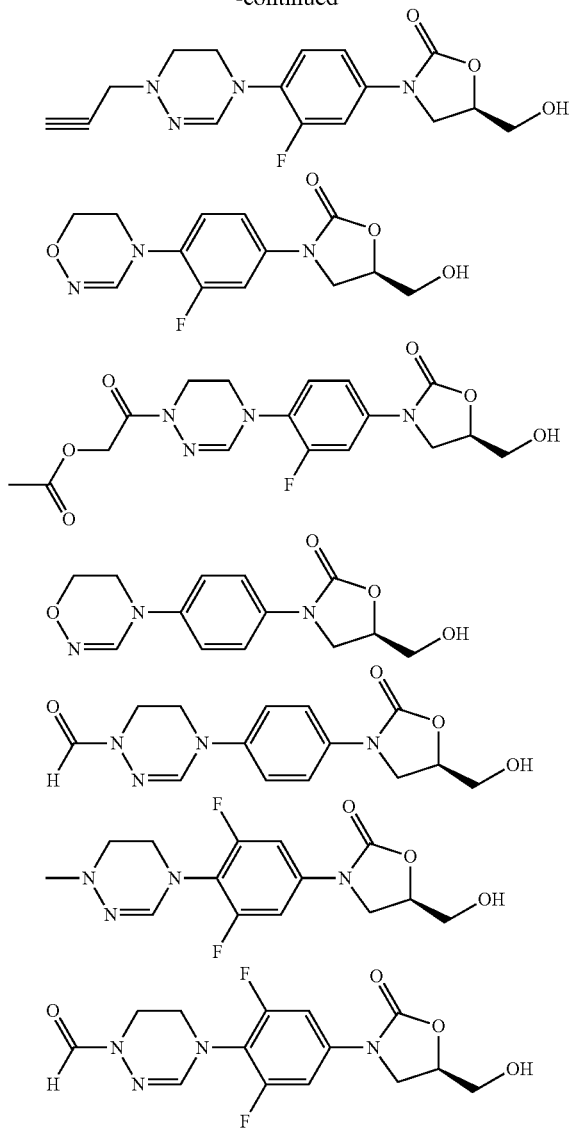

The novel oxazolidinone derivatives according to the present invention have a cyclic amidoxime or a cyclic amidrazone group and can be prepared into prodrugs, hydrates, solvates, isomers or pharmaceutically acceptable salts in order to improve absorption into the body or to enhance solubility. Therefore, the prodrugs, hydrates, solvates, isomers or pharmaceutically acceptable salts also fall within the scope of the present invention.

The novel oxazolidinone derivatives according to the present invention can be converted to pharmaceutically acceptable salts. The term "pharmaceutically acceptable salts refers to acid addition salts" useful for administering the compounds of this invention, and include methanesulfonate, ethanesulfonate, fumarate, succinate, hydrochloride, citrate, malate, tartrate and (less preferably) hydrobromide, phosphate, sulfate and the like. Further, an adequate basic salt includes, for example, an alkali metal salt (e.g., sodium salt) or an alkaline earth metal salt (e.g., calcium or magnesium salt), an organic amine salt (e.g., triethylamine, morpholine, N-methylpiperidine, N-ethylpiperidine, dibenzylamine, N,N-dibenzylethylamine and tris-(2-hydroxyethyl)amine), or an amino acid (e.g., N-methyl-d-glutamine and lysine). The salts may include one or more cation(s) or anion(s) depending on the number of charged group(s) and the valence of the corresponding cation(s) or anion(s). A preferred pharmaceutically acceptable basic salt is a sodium salt. However, in order to facilitate release of salt during preparation, a salt less soluble in the selected solvent may be preferred.

The oxazolidinone derivative of the present invention may be present either in a solvated form, e.g. as a hydrate, or in a non-solvated form. The solvates of the oxazolidinone derivatives according to the present invention include all pharmaceutically active solvated forms.

The oxazolidinone derivatives of the present invention may be administered in a prodrug form, which is transformed in the body of human or animal to provide the active ingredient of the present invention. The prodrug may be formed by introducing an adequate group or substituent capable of modifying or improving the physical and/or pharmacological profile of the parent compound. Examples of the prodrug include esters of the compounds of the present invention and pharmaceutically acceptable salts thereof that can be hydrolyzed in vivo.

Various types of prodrug forms are known in the related art. For example, refer to:

a) Design of Prodrugs, edited by H. Bundgaard, (Elsevier, 1985) and Methods in Enzymology, Vol. 42, p. 309-396, edited by K. Widder, et al. (Academic press, 1985);

b) A Textbook of Drug Design and Development, edited by Krogsgaard-Larsen and H. Bundgaard, Chapter 5 "Design and Application of Prodrugs", by H. Bundgaard p. 113-191 (1991);

c) H. Bundgaard, Advanced Drug Delivery Reviews, 8, 1-38 (1992);

d) H. Bundgaard, et al., *Journal of Pharmaceutical Sciences*, 77, 285 (1988); and e) N. Kakeya, et al., *Chem. Pharm. Bull.*, 32, 692 (1984).

Examples of the prodrug according to the present invention include the following compounds.

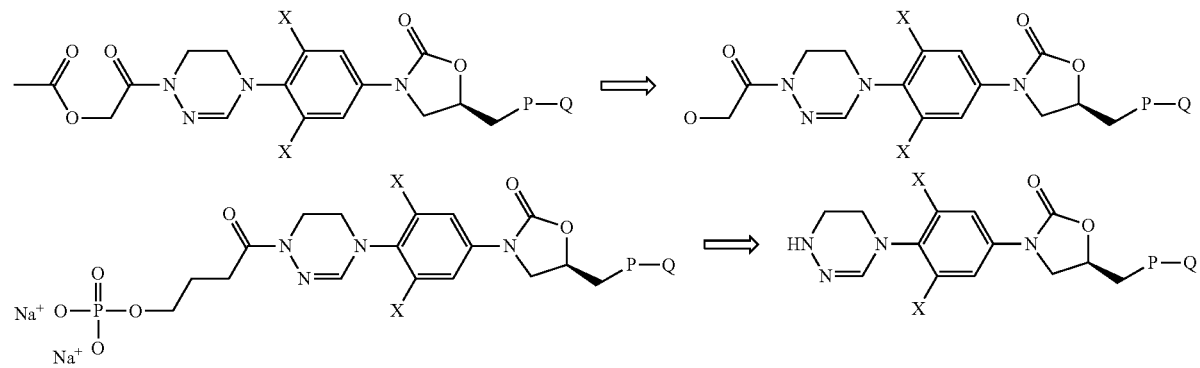

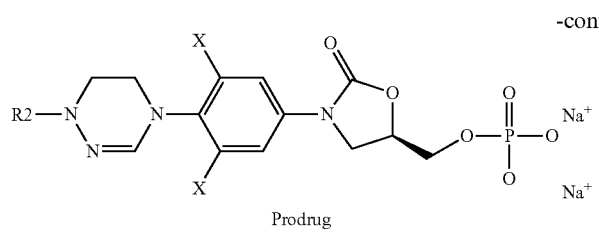

Prodrug

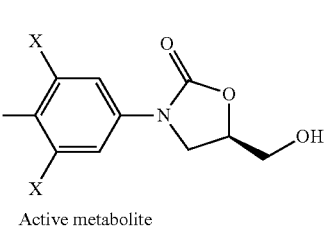

Active metabolite

As in the foregoing examples, a phosphonate or acetyl group may be attached on the hydroxyl group, so that the prodrug is transformed to an active form after administration. Alternatively, an amino acid may be attached or a carbonate form may be prepared. The prodrug form is used mainly when the solubility is relatively low or absorptivity is low. The use of the prodrug may lead to the improvement of absorption, distribution, metabolism and excretion (ADME) and PK profile, in addition to the enhancement of solubility and absorptivity.

The compound of the present invention has a chiral center at the C-5 position of the oxazolidinone ring. A preferred diastereomer of the oxazolidinone derivative compound according to the present invention is represented by Chemical Formula 1. Compared to the epimer represented by Chemical Formula 1b, it exhibits a better MAO profile.

[Chemical Formula 1b]

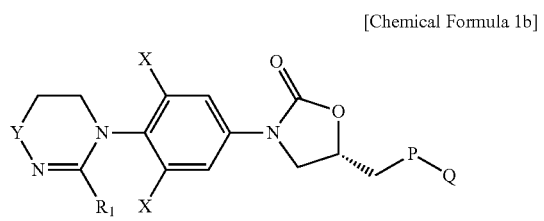

When a mixture of epimers with respect to the oxazolidinone chiral center is used, the amount may be controlled considering the proportion of the enantiomers (or diastereomers) in order to attain a comparable pharmacological effect as compared to when the mirror-image isomer is used alone.

Further, some compounds of the present invention may have a different chiral center depending on their substituent(s). All optical isomers, diastereomers and mixtures having antibacterial activity are included in the scope of the present invention. The method for preparing optically active forms (e.g., recrystallization, chiral synthesis, enzymatic resolution, biotransformation, or separation of mixtures by chromatography) and the method for measurement of antibacterial activity are known in the related art.

As the compounds represented by Chemical Formula 1 or the salts thereof may tautomerize, even though only one of possible tautomers is described in the chemical formulas or reaction schemes in the description, the present invention encompasses all the tautomers having antibacterial activity and is not limited to the tautomer form described in the chemical formulas or reaction schemes.

Further, the compound of the present invention may exhibit polymorphism. Thus, all the polymorphic compounds having antibacterial activity are included in the present invention.

The novel oxazolidinone derivatives according to the present invention may be prepared through alternative methods depending on their substituents. For example, they may be prepared according to the methods exemplified by Schemes 1 to 6. The preparation methods described in Schemes 1 to 6 are only exemplary and may be easily modified by those skilled in the art depending on the particular substituents. Accordingly, the methods exemplified in Schemes 1 to 6 do not limit the method for preparing the oxazolidinone compounds of the present invention. Unless otherwise specified, definitions for the substituents in the reaction schemes are the same as in Chemical Formula 1.

The oxazolidinone derivatives of Chemical Formula 1 according to the present invention may be synthesized via different synthetic routes, depending on $X_1$, $X_2$, Y, P and Q. Representative synthesis methods in the cases where $X_1$ is fluorine atom (F) and $X_2$ is hydrogen atom (H) are exemplified in Schemes 1 to 5. And, the case where both $X_1$ and $X_2$ are H or F is exemplified in Scheme 6.

For preparations of cyclic amidrazone compounds, with Y being nitrogen atom (N—$R_2$), synthesis methods in the case where P is NH are exemplified in Schemes 1 and 2, a synthesis method in the case where P is a aromatic heterocycle (e.g., Triazole) is exemplified in Scheme 3, and the case where P is oxygen atom (O) is exemplified in Scheme 4. Further, a synthesis method of cyclic amidoxime compounds, with Y being O, is exemplified in Scheme 5.

Referring to Scheme 1, 3, 4-difluoronitrobenzene is reacted with ethanolamine to give Compound I. After protecting the alcohol and amine groups with (t-butyldimethylsilyl (TBS) and tert-butyloxycarbonyl (boc)sequentially (Compound II), the nitro group is reduced to amine using Pd/C (Compound III). Benzyloxycarbonyl group (cbz) is attached using benzyl chloroformate (Cbz-Cl) to synthesize Compound IV. Compound IV is reacted with (R)-glycidyl butyrate and n-butyllithium (n-BuLi) to synthesize chiral Compound V. Compound V is reacted with methanesulfonyl chloride (Ms-Cl) (Compound VI), and then with sodium azide (NaN$_3$) (Compound VII). After converting the azide group into amine using Pd/C under hydrogen gas, a cbz group is attached using Cbz-Cl to synthesize Compound VIII. Compound VIII is treated with hydrochloric acid to remove the protecting groups (boc and tbs) to give Compound IX, which is reacted with methanesulfonyl chloride (Ms-Cl) to synthesize Compound X. Reaction of compound X with hydrazine followed by reaction with trimethyl orthoformate gives a cyclic amidrazone compound XII. After removing the cbz group from Compound XII (Compound XIII), a variety of Q groups can be introduced thereto. Further, after removing the formyl group, a variety of $R_2$ groups can be introduced. Specific examples are described in the preparation compounds.

[Scheme 1]

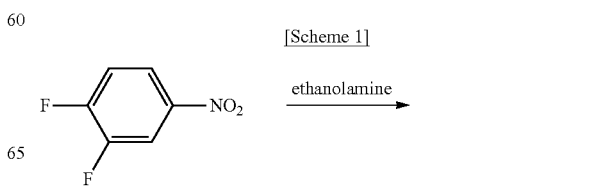

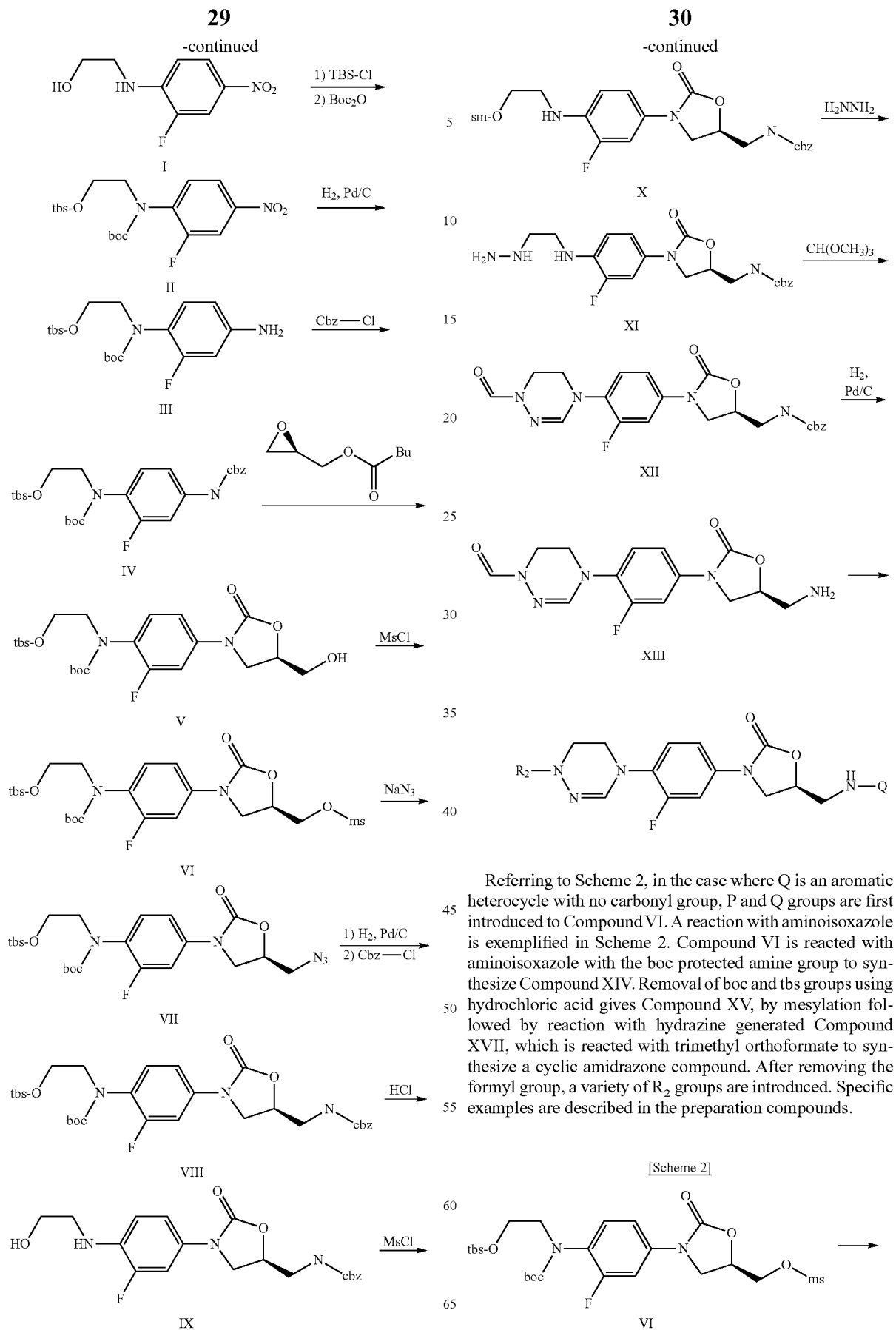

Referring to Scheme 2, in the case where Q is an aromatic heterocycle with no carbonyl group, P and Q groups are first introduced to Compound VI. A reaction with aminoisoxazole is exemplified in Scheme 2. Compound VI is reacted with aminoisoxazole with the boc protected amine group to synthesize Compound XIV. Removal of boc and tbs groups using hydrochloric acid gives Compound XV, by mesylation followed by reaction with hydrazine generated Compound XVII, which is reacted with trimethyl orthoformate to synthesize a cyclic amidrazone compound. After removing the formyl group, a variety of $R_2$ groups are introduced. Specific examples are described in the preparation compounds.

[Scheme 2]

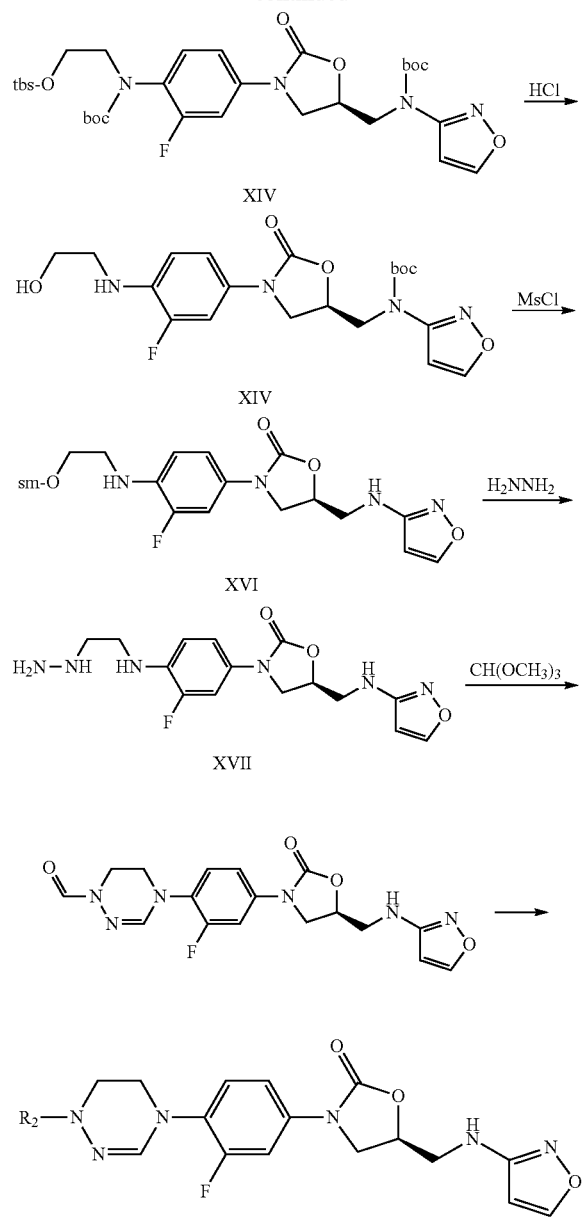
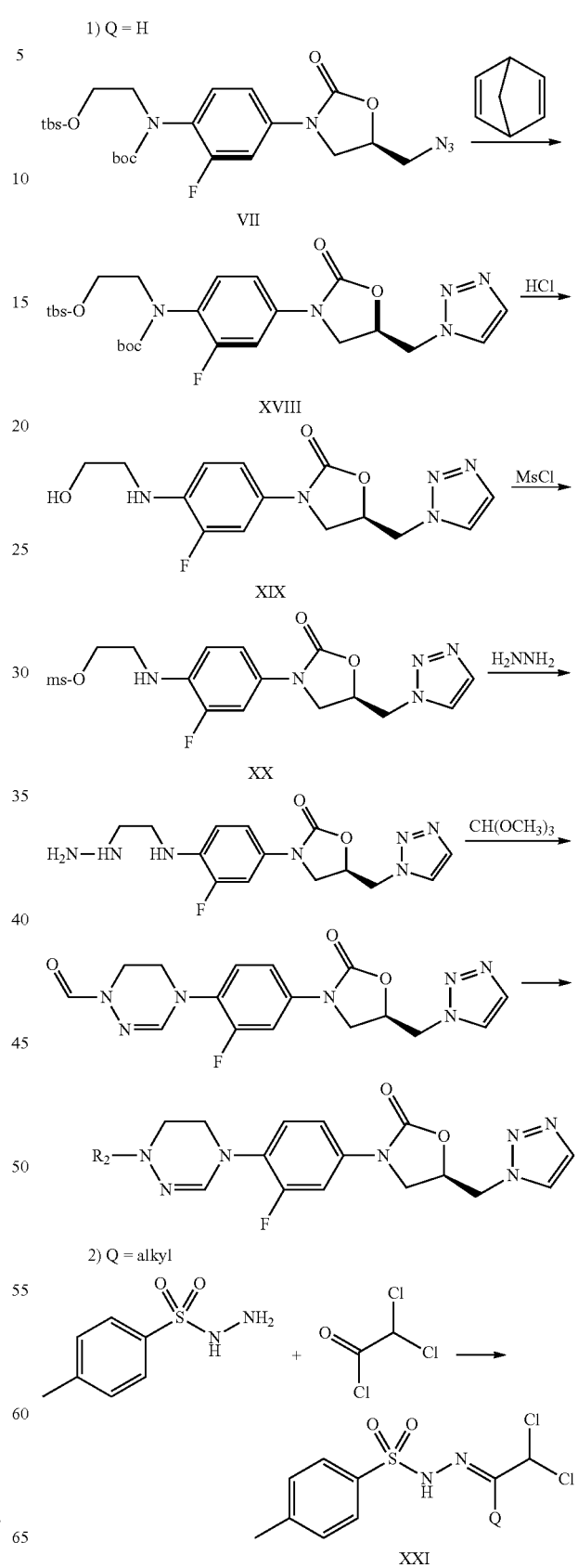

Referring to Scheme 3, the case where P is an aromatic heterocycle is subdivided into 1) where Q is H and 2) where Q is a substituent other than H. First, for a compound wherein Q is H, an azido compound (Compound VII) is reacted with 2,5-norbornadiene to synthesize a triazole compound (Compound XVIII). Removal of boc and tbs groups using hydrochloric acid gives Compound XIX. Mesylation (Compound XX), treatment with hydrazine followed by trimethyl orthoformate gives a cyclic amidrazone compound. Compounds wherein Q is a substituent other than H can be prepared as follows; a dichlorotosylhydrazone compound XXI is prepared by reacting tosylhydrazide and acid chloride as shown. Reaction of the amine XIII and tosylhydrazone XXI gives cyclic amidrazone intermediate, which after removal of formyl group is dervatized with variety of R₂ groups. Specific examples are described in the preparation compounds.

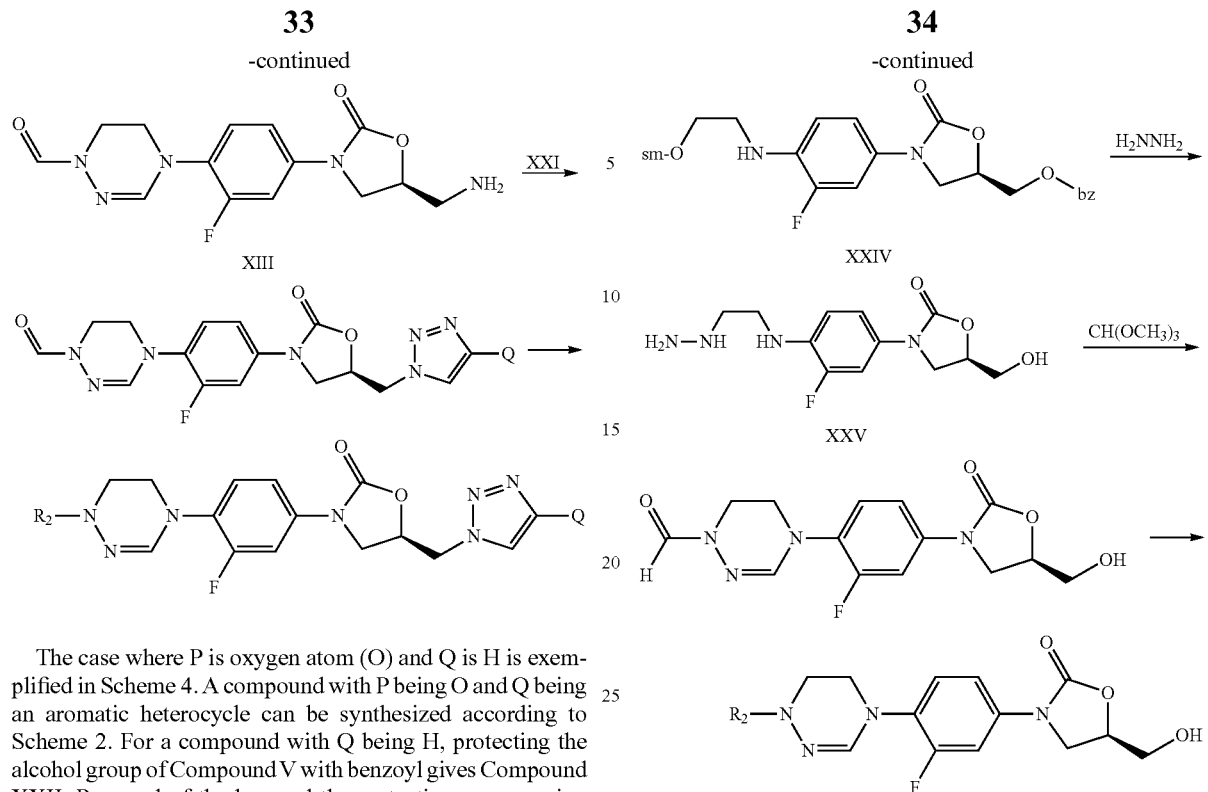

The case where P is oxygen atom (O) and Q is H is exemplified in Scheme 4. A compound with P being O and Q being an aromatic heterocycle can be synthesized according to Scheme 2. For a compound with Q being H, protecting the alcohol group of Compound V with benzoyl gives Compound XXII. Removal of the boc and tbs protecting groups using hydrochloric acid (Compound XXIII) and mesylation gives Compound XXIV, which is reacted with hydrazine to give Compound XXV. During the reaction with hydrazine, the benzoyl group is found to be removed. The hydrazine compound is reacted with trimethyl orthoformate to synthesize a cyclic amidrazone compound. After removing the formyl group, a variety of R₂ groups are introduced. Specific examples are described in the preparation compounds.

A synthesis method of a cyclic amidoxime compound with Y being O is exemplified in Scheme 5. Depending on whether P-Q is OH or not, the cases are subdivided into 1) and 2).

1) Unless P-Q is OH, P and Q groups are introduced to Compound VI according to Schemes 1 to 4 to synthesize Compound XXVI, which is treated with hydrochloric acid to remove boc and tbs groups yielding Compound XXVII. Compound XXVII is subjected to Mitsunobu condition with hydroxyphthalimide to obtain Compound XXVIII. Removal of phthalimide using hydrazine followed by reaction with trimethyl orthoformate gives a cyclic amidoxime compound.

2) When P-Q is OH, the alcohol group of oxazolidinone part has to be protected with benzoyl group (Compound XXIII). Mitsunobu reaction with hydroxyphthalimide gives Compound XXIX. Removal of phthalimide using hydrazine followed by reaction with trimethyl orthoformate gives a cyclic amidoxime compound. Again, the benzoyl group is removed during the hydrazine reaction. A cyclic amidoxime compound can also be obtained by reacting with trimethyl orthoformate.

[Scheme 4]

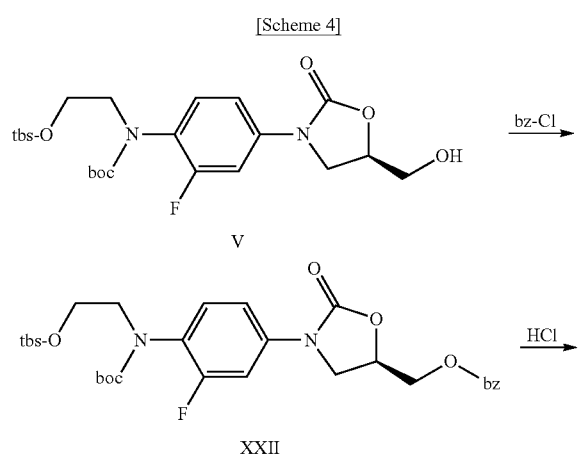

[Scheme 5]

1)

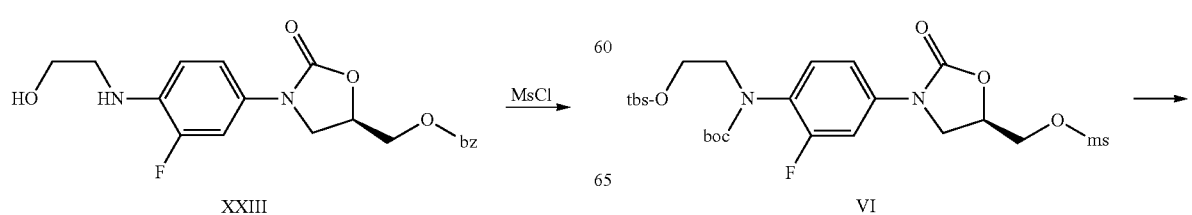

-continued

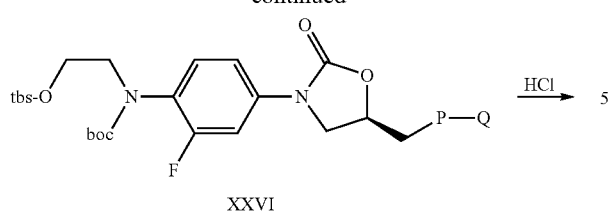

XXVI

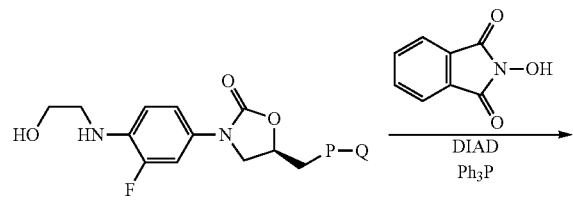

XXVII

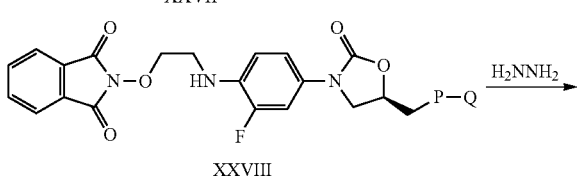

XXVIII

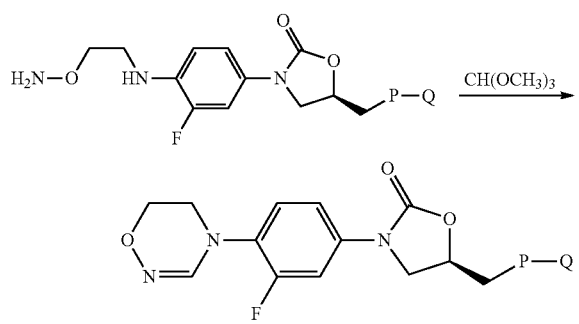

2)

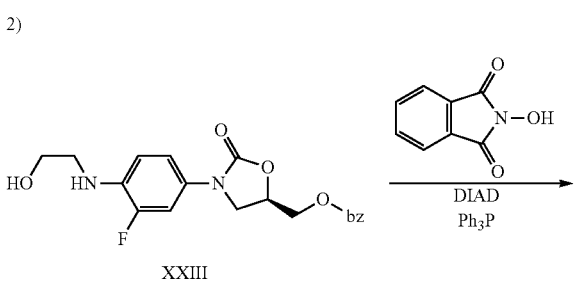

XXIII

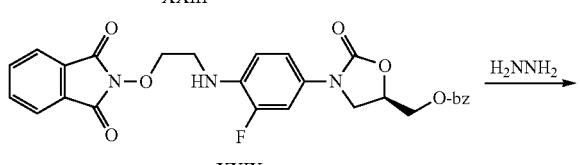

XXIX

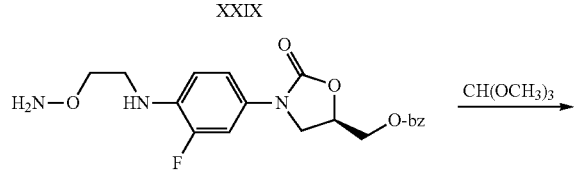

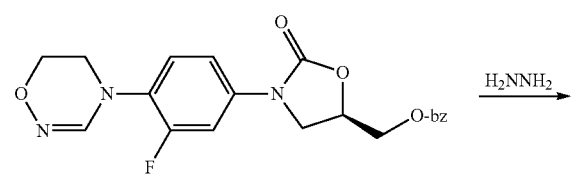

-continued

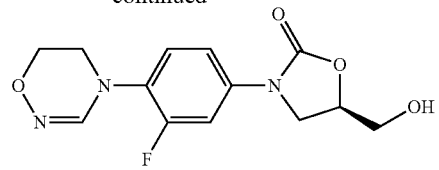

The cases where $X_1$ is F and $X_2$ is H were described in Schemes 1 to 5. Referring to Scheme 6, a compound with both $X_1$ and $X_2$ being H or F can be synthesized in the same manner as Schemes 1 to 5, the only difference is that 4-fluoronitrobenzene or 3,4,5-trifluoronitrobenzene is used as a starting material.

*[Scheme 6]

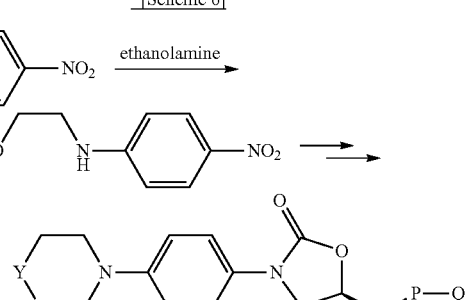

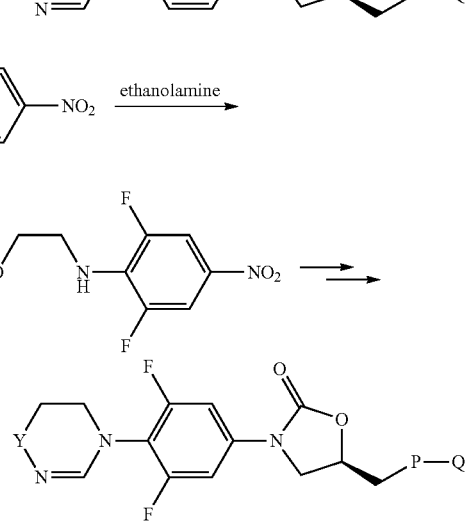

The compositions of the present invention can be in a adequate form for oral administration (e.g., tablet, lozenge, hard or soft capsule, aqueous or oily suspension, emulsion, dispersible powder or granule, syrup or elixir), in a form adequate for topical application (e.g., cream, ointment, gel, aqueous or oily solution or suspension), in a form adequate for ocular administration, in a form adequate for administration by inhalation (e.g., finely divided powder or liquid aerosol), in a form adequate for administration by insufflation (e.g., finely divided powder), or in a form adequate for parenteral administration (e.g., aqueous or oily sterile solution for intravenous, subcutaneous, sublingual or intramuscular injection, or rectal suppository).

In addition to the compounds of the present invention, the pharmaceutical compositions of the present invention may further comprise (i.e., formulated together with) one or more known drug(s) selected from clinically useful antibacterial agents (e.g., β-lactam, macrolide, quinolone or aminoglycoside) and antiinflammatory agents (e.g., antifungal triazole or amphotericin), or may be administered in combination with one or more the known drug(s). The compositions may further comprise carbapenem, e.g., meropenem or imipenem, to enhance therapeutic effect. Further, the compounds of the present invention may be formulated together with or administered in combination with a bactericidal/permeability increasing protein (BPI) product or an efflux pump inhibitor, in order to increase activity against Gram-negative bacteria and antibiotic resistant bacteria.

The compounds of the present invention may be formulated together with or administered in combination with vitamin, e.g., vitamin B, such as vitamin B2, vitamin B6 or vitamin B12, and folic acid. Further, the compounds of the present invention may be formulated together with or administered in combination with a cyclooxygenase (COX) inhibitor, particularly COX-2 inhibitor. In addition, the compounds of the present invention may be formulated together with or administered in combination with an antibacterial agent active against Gram-positive bacteria or Gram-negative bacteria.

The compositions of the present invention may be prepared using a commonly used known pharmaceutical excipient. Accordingly, a composition intended for oral administration may comprise, for example, one or more coloring agent, sweetening agent, flavoring agent and/or antiseptic. Preferably, a pharmaceutical composition for intravenous administration may comprise (for example, in order to enhance stability) adequate bactericide, antioxidant, reducing agent, or sequestrant.

A composition for oral administration may be in the form of hard gelatin capsule prepared by mixing the active ingredient with an inert solid diluent, e.g., calcium carbonate, calcium phosphate or kaolin, or in the form of soft gelatin capsule prepared by mixing the active ingredient with water or oil, e.g., peanut oil, liquid paraffin or olive oil.

An aqueous suspension generally comprises one or more suspending agent(s), for example, sodium carboxymethylcellulose, methylcellulose, hydroxypropylmethylcellulose, sodium alginate, polyvinylpyrrolidone, gum tragacanth or gum acacia, or dispersing or wetting agent(s), for example, lecithin, condensation product of alkylene oxide with fatty acid (e.g., polyoxyethylene stearate), condensation product of ethylene oxide with long-chain aliphatic alcohol, e.g., heptadecaethyleneoxycetanol, condensation product of ethylene oxide with partial ester derived from fatty acid and hexitol, e.g., polyoxyethylene sorbitol monooleate, condensation product of ethylene oxide with partial ester derived from fatty acid and hexitol anhydride, e.g., polyethylene sorbitan monooleate, in addition to the active ingredient in the form of finely divided powder. The aqueous suspension may further comprise one or more antiseptic(s) (e.g., ethyl or propyl p-hydroxybenzoate), antioxidant(s) (e.g., ascorbic acid), coloring agent(s), flavoring agent(s), and/or sweetening agent(s) (e.g., sucrose, saccharin or aspartame).

An oily suspension may be prepared by suspending the active ingredient in vegetable oil (e.g., arachis oil, olive oil, sesame oil or coconut oil) or mineral oil (e.g., liquid paraffin). The oily suspension may further comprise a thickener, e.g., beeswax, paraffin wax or cetyl alcohol. Further, the aforementioned sweetening agent or flavoring agent may be added to provide a tasty oral administration composition. The composition may be preserved by addition of an antioxidant such as ascorbic acid.

Dispersible powder or granule adequate for preparing an aqueous suspension by adding water thereto comprises a dispersing or wetting agent, a suspending agent and one or more antiseptic(s), in addition to the active ingredient. Examples of adequate dispersing or wetting agents and suspending agents are described earlier. There may also be comprised of an additional excipient such as a sweetening agent, a flavoring agent and a coloring agent.

Further informations about formulations may be found in Chapter 25.2 in Volume 5 of Comprehensive Medicinal Chemistry (Corwin Hansch; Chairman of Editorial Board), Pergamon Press, 1990.

The amount of the active ingredient mixed with one or more excipient(s) to prepare a unit-dose formulation may vary, of course, depending on the subject in need thereof and the particular route of administration. For example, a formulation for oral administration to human may comprise, in general, 50 mg to 5 g of the active ingredient compound along with an adequate amount of excipient (The content may range from about 5 to about 98% based on the total weight of the composition). In general, a unit-dose formulation will comprise from about 200 mg to about 2 g of the active ingredient. Further informations about administration route and administration regimen can be found in Chapter 25.3 in Volume 5 of Comprehensive Medicinal Chemistry (Corwin Hansch; Chairman of Editorial Board), Pergamon Press, 1990.

An adequate pharmaceutical composition of the present invention is a unit-dose formulation adequate for oral administration, for example, a tablet or capsule comprising 0.1 mg to 1 g, preferably 100 mg to 1 g, of the compound of the present invention. Especially, a tablet or capsule comprising 50 mg to 800 mg of the compound of the present invention is preferable.

Further, the pharmaceutical compositions of the present invention may be a formulation adequate for intravenous, subcutaneous or intramuscular injection, for example, an injection comprising 0.1% w/v to 50% w/v (1 mg/mL to 500 mg/mL) of the compound of the present invention.

To each patient, the compound of the present invention may be administered intravenously, subcutaneously or intramuscularly, for example, at a dose of 0.1 mg/kg to 20 mg/kg per day. The corresponding composition is administered once to four times a day. In another embodiment, the compound of the present invention is administered at a dose of 1 mg/kg to 20 mg/kg per day. A dose for intravenous, subcutaneous or intramuscular administration may be provided by bolus injection. Alternatively, a dose for intravenous administration may be continuous injection over a period of time. Also, a single-day dose for oral administration, which may be approximately equivalent to a single-day dose for parenteral administration, may be administered to each patient. The corresponding composition is administered once to four times a day.

When compared with the linezolid currently marketed by Pfizer, the oxazolidinone derivatives of the present invention exhibit antibacterial activity against several bacteria resistant to pre-existing antibiotics, including Gram-positive bacteria such as *Staphylococcus aureus, Enterococcus faecalis*, etc. and Gram-negative bacteria such as *Haemophilus influenzae, Moraxella catarrhalis*, etc., particularly excellent antibacterial activity against linezolid-resistant *Enterococcus faecalis*, at much lower concentrations.

Mode for the Invention

The examples and experiments will now be described. However, the following examples and experiments are for illustrative purposes only and are not intended to limit the scope of the present invention.

PREPARATION EXAMPLE 1

Preparation of Compound I

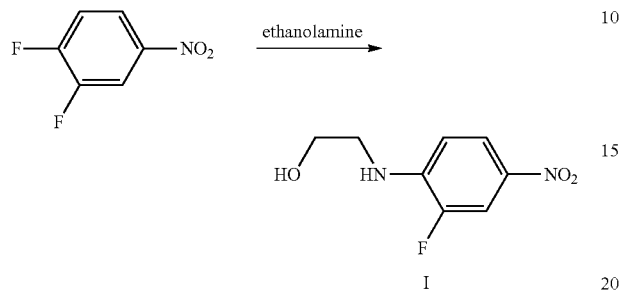

After dissolving 3,4-difluoronitrobenzene (158 g, 0.99 mol) in acetonitrile (800 mL) and adding ethanolamine (117 g, 1.9 mol), the mixture was stirred for 4 hours under reflux. The reaction solution was cooled to room temperature, concentrated under reduced pressure, triturated with diethyl ether, and filtered to obtain yellow Compound I (199 g, 0.99 mol, 100%).

$^1$H NMR (400 MHz, chloroform-d$_1$) δ 7.97 (d, 1H, J=8.8 Hz), 7.87 (dd, 1H, J$_1$=11.6 Hz, J$_2$=2.4 Hz), 6.65 (t, 1H, J=8.8 Hz), 5.10-4.87 (bs, 1H), 3.97-3.83 (m, 2H), 3.43-3.37 (m, 2H).

PREPARATION EXAMPLE 2

Preparation of Compound II

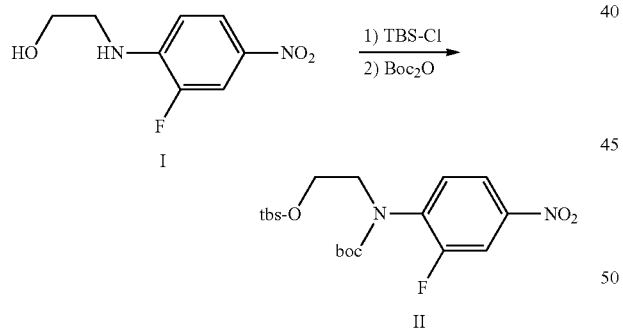

Compound I (100 g, 0.5 mol), t-butyldimethylsilyl chloride (TBS-Cl, 97 g, 0.65 mol) and imidazole (51 g, 0.75 mol) were dissolved in dichloromethane (700 mL) at 0° C. and stirred overnight after slowly heating to room temperature. The reaction solution was concentrated under reduced pressure, dissolved in ethyl acetate and washed with 0.5 N HCl, washed sequentially with saturated aqueous sodium bicarbonate solution and saturated aqueous sodium chloride solution (brine), dried with anhydrous sodium sulfate, and concentrated under reduced pressure to quantitatively obtain a compound with a tbs group attached to alcohol. This compound was dissolved in THF (500 mL) and 1.2 equivalents of Boc$_2$O and 0.1 equivalent of 4-dimethylaminopyridine (DMAP) were added. After stirring for 3 hours at room temperature, ammonia water (30 mL) was added. After stirring further for 20 minutes, the solution was concentrated under reduced pressure. The concentrate was dissolved again in ethyl acetate, sequentially washed with 0.5 N HCl, saturated aqueous sodium bicarbonate solution and saturated aqueous sodium chloride solution (brine), dried with anhydrous sodium sulfate, and concentrated under reduced pressure to quantitatively obtain Compound II.

$^1$H NMR (600 MHz, chloroform-d$_1$) δ 8.06-7.98 (m, 1H), 7.95 (dd, 1H, J$_1$=10.2 Hz, J$_2$=2.4 Hz), 7.57 (t, 1H, J=7.8 Hz), 3.80 (t, 2H, J=5.4 Hz), 3.73 (t, 2H, J=4.8 Hz), 1.42 (s, 9H), 0.81 (s, 9H), 0.01 (s, 6H).

PREPARATION EXAMPLE 3

Preparation of Compound III

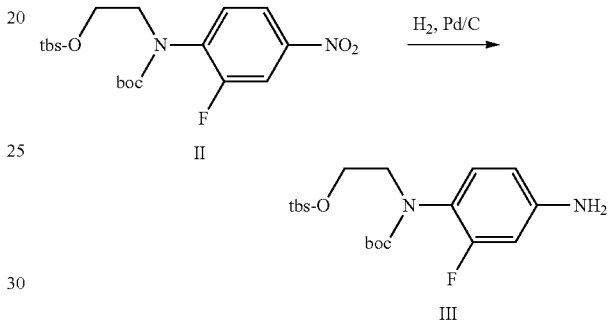

Compound II (92 g, 0.22 mol) was dissolved in methanol (600 mL) and stirred for 4 hours under hydrogen balloon after adding Pd/C (6 g). The reaction mixture was filtered using celite and concentrated under reduced pressure to quantitatively obtain Compound III (86 g) as a colorless oil.

$^1$H NMR (400 MHz, chloroform-d$_1$) δ 6.99 (t, 1H, J=12.0 Hz), 6.44-6.30 (m, 2H), 3.81-3.63 (m, 4H), 3.63-3.52 (m, 2H), 1.50 (s, 3H), 1.35 (s, 6H), 0.86 (s, 9H), 0.03 (s, 6H).

PREPARATION EXAMPLE 4

Preparation of Compound IV

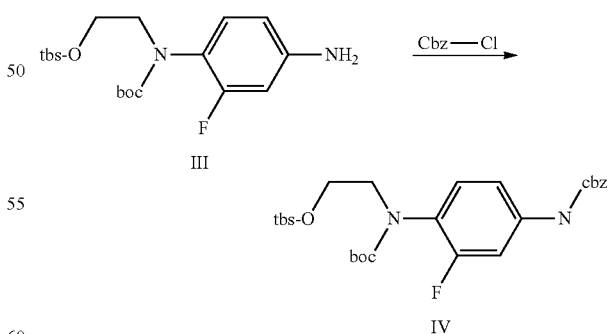

Compound III (86 g, 0.22 mol) was dissolved in dichloromethane (300 mL). After adding aqueous 1 N NaOH solution (300 mL), benzyl chloroformate (Cbz-Cl, 38 mL, 0.27 mol) was slowly added dropwise while stirring. After stirring for 1 hour at room temperature, the organic layer was separated, washed twice with water, dried with anhydrous sodium sulfate, and concentrated under reduced pressure to quantitatively obtain Compound IV (116 g) as a yellow oil.

$^1$H NMR (600 MHz, chloroform-d$_1$) δ 7.44-7.32 (m, 6H), 7.18 (t, 1H, J=8.1 Hz), 6.96 (d, 1H, J=8.4 Hz), 6.84-6.66 (bs, 1H), 5.20 (s, 2H), 3.82-3.63 (m, 2H), 3.63-3.58 (m, 2H), 1.51 (s, 3H), 1.35 (s, 6H), 0.86 (s, 9H), 0.02 (s, 6H).

PREPARATION EXAMPLE 5

Preparation of Compound V

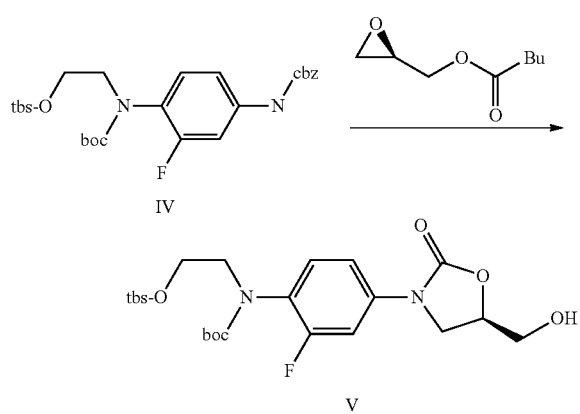

Compound IV (116 g, 0.22 mol) was dissolved in THF (400 mL) and stirred for 20 minutes after slowly adding n-butyllithium (2.5 M solution in n-hexane, 90 mL, 0.23 mol) dropwise at −78° C. After adding (R)-glycidyl butyrate (31.5 mL, 0.23 mol), followed by stirring for 3 hours while slowly heating to room temperature, the solution was adjusted to pH ~6 with aqueous ammonium chloride solution, and concentrated under reduced pressure. The concentrate was dissolved in 80% ethyl acetate/hexane solution, sequentially washed with water and saturated aqueous sodium chloride solution (brine), dried with anhydrous sodium sulfate, and concentrated under reduced pressure. The concentrate was separated by column chromatography using 40% ethyl acetate/hexane solution to obtain Compound V (45 g, 0.093 mol, 42%) as a colorless oil.

$^1$H NMR (600 MHz, CDCl$_3$) δ 7.50-7.48 (m, 1H), 7.30-7.28 (m, 1H), 7.17-7.16 (m, 1H), 4.74-4.70 (m, 1H), 4.03-4.02 (m, 1H), 3.98 (m, 2H), 3.75 (m, 3H), 3.65 (m, 2H), 1.51 (s, 3H), 1.36 (s, 6H), 0.85 (s, 9H), 0.02 (s, 6H).

PREPARATION EXAMPLE 6

Preparation of Compound VI

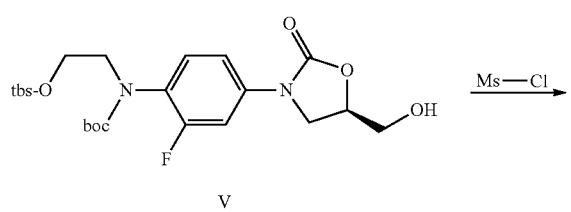

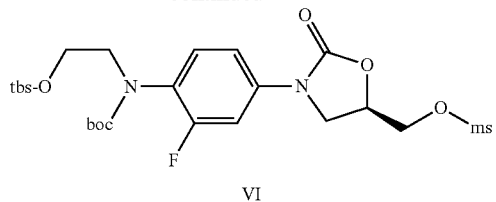

Compound V (45 g, 0.093 mol) was dissolved in dichloromethane (300 mL) and stirred for 20 minutes after sequentially adding triethylamine (26 mL, 0.186 mol) and methanesulfonyl chloride (MsCl, 10.9 mL, 0.14 mol) dropwise at 0° C. After heating to room temperature, followed by stirring for 1 hour, the solution was concentrated under reduced pressure. The concentrate was dissolved in ethyl acetate, sequentially washed with 0.5 N HCl, saturated aqueous sodium bicarbonate solution and saturated aqueous sodium chloride solution (brine), dried with anhydrous sodium sulfate, and concentrated under reduced pressure to obtain Compound VI (50 g, 0.089 mol, 96%) as a yellow oil.

$^1$H NMR (400 MHz, CDCl$_3$) δ 7.46 (dd, 1H, J$_1$=11.6 Hz, J$_2$=2.4 Hz), 7.29 (m, 1H), 7.13 (m, 1H), 4.94-4.88 (m, 1H), 4.50-4.39 (m, 2H), 4.12 (m, 1H), 3.92 (m, 1H), 3.72 (m, 2H), 3.64-3.62 (m, 2H), 3.08 (s, 3H), 1.49 (s, 3H), 1.34 (s, 6H), 0.83 (s, 9H), 0.00 (s, 6H).

PREPARATION EXAMPLE 7

Preparation of Compound VII

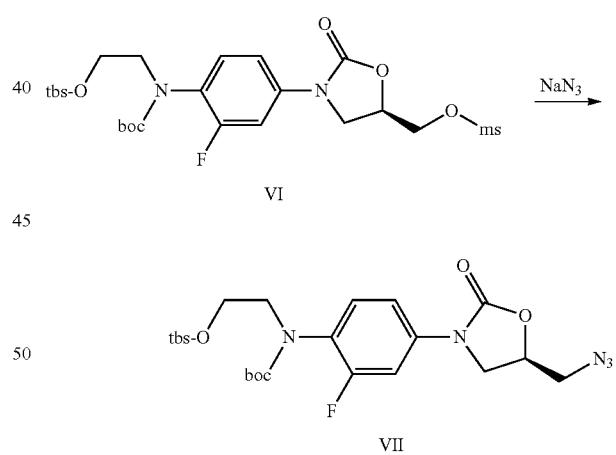

Compound VI (50 g, 0.089 mol) was dissolved in DMF (200 mL) and stirred for 3 hours at 80° C. after adding NaN$_3$ (7.16 g, 0.11 mol). The solution was cooled to room temperature, diluted with ethyl acetate, sequentially washed with water, saturated aqueous sodium bicarbonate solution and saturated aqueous sodium chloride solution (brine), dried with anhydrous sodium sulfate, and concentrated under reduced pressure to quantitatively obtain Compound VII (47 g, 0.089 mol) as a colorless oily solid.

$^1$H NMR (600 MHz, CDCl$_3$) δ 7.48 (dd, J$_1$=8.2 Hz, J$_2$=1.4 Hz) 7.30 (m, 1H), 7.16 (m, 1H), 4.81-4.79 (m, 1H), 4.09-4.08

(m, 1H), 3.86 (m, 1H), 3.74 (m, 2H), 3.62-3.59 (m, 1H), 1.51 (s, 3H), 1.36 (s, 6H), 0.85 (s, 9H), 0.02 (s, 6H).

PREPARATION EXAMPLE 8

Preparation of Compound VIII

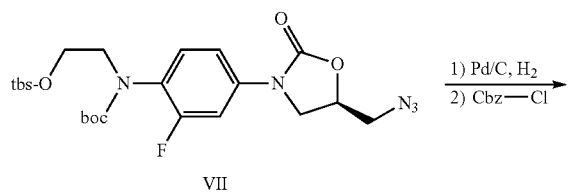

Compound VII (47 g, 0.089 mol) was dissolved in methanol (400 mL) and stirred for 4 hours under hydrogen balloon after adding Pd/C (3.5 g). The solution was filtered with celite and concentrated under reduced pressure. The concentrate was dissolved in dichloromethane (130 mL) and, after adding aqueous 1 N NaOH solution (130 mL), Cbz-Cl (15.5 mL, 0.11 mol) was slowly added dropwise while stirring. After stirring for 2 hours at room temperature, the organic layer was separated, washed with water and saturated aqueous sodium chloride solution (brine), dried with anhydrous sodium sulfate, concentrated under reduced pressure, and separated by column chromatography using 20% ethyl acetate/hexane solution to obtain Compound VIII (50.5 g, 0.082 mol, 92%) as a light yellow oil.

$^1$H NMR (400 MHz, CDCl$_3$) δ 7.46-7.43 (m, 1H), 7.36-7.35 (m, 1H), 7.31 (s, 6H), 7.11 (m, 1H), 5.09 (s, 2H), 4.75 (m, 1H), 4.01 (t, 1H, J=8.4 Hz), 3.76-3.50 (m, 1H), 1.49 (s, 3H), 1.34 (s, 6H), 0.83 (s, 9H), 0.01 (s, 6H).

PREPARATION EXAMPLE 9

Preparation of Compound IX

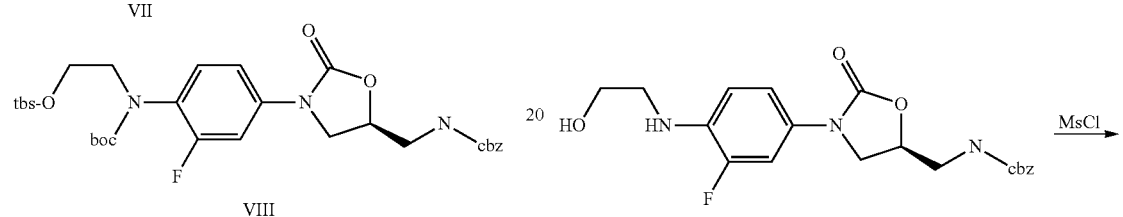

Compound VIII (50.5 g, 0.082 mol) was dissolved in dichloromethane (100 mL), stirred for 3 hours at room temperature after adding 4 N HCl solution in dioxane (130 mL), and concentrated under reduced pressure to quantitatively obtain Compound IX (36 g, 0.082 mol) as a white solid.

$^1$H NMR (400 MHz, DMSO-d$_6$) δ 7.69 (t, 1H, J=6.0 Hz), 7.44-7.40 (m, 1H), 7.32 (s, 6H), 7.09-7.07 (m, 1H), 6.88 (t, 1H, J=9.2 Hz), 5.03 (s, 2H), 4.71-4.68 (m, 1H), 4.08-4.03 (m, 2H), 3.73-3.69 (m, 1H), 3.60-3.57 (m, 3H), 3.39-3.34 (m, 2H), 3.18-3.15 (m, 2H).

PREPARATION EXAMPLE 10

Preparation of Compound XII

Compound IX (36 g, 0.082 mol) was dissolved in dichloromethane (300 mL) and stirred for 10 minutes after slowly adding triethylamine (34.5 mL, 0.245 mol) and methanesulfonyl chloride (MsCl, 9.5 mL, 0.123 mol) sequentially at 0° C. dropwise. The solution was heated to room temperature, stirred for 2 hours, diluted with dichloromethane, sequentially washed with water, saturated aqueous sodium bicarbonate solution and saturated aqueous sodium chloride solution (brine), dried with anhydrous sodium sulfate, and concentrated under reduced pressure. The resultant solid was triturated with diethyl ether solvent and filtered to obtain Compound X (30.5 g, 0.063 mol, 77%) as a white solid.

Compound X (20 g, 0.042 mol) was added to ethanol (100 mL) and stirred for 2 hours at 60° C. after adding hydrazine monohydrate (H$_2$NNH$_2$—H$_2$O, 50 mL). The solution was concentrated under reduced pressure to obtain Compound XI (17.4 g, 0.042 mol) as an oil.

Compound XI (17.4 g, 0.042 mol) was added to acetic acid (200 mL) and refluxed for 8 hours after adding trimethyl orthoformate (100 mL). The solution was distilled under reduced pressure, dissolved in dichloromethane, sequentially washed with saturated aqueous sodium bicarbonate solution and saturated aqueous sodium chloride solution (brine), dried with anhydrous sodium sulfate, and concentrated under reduced pressure. The concentrate was separated by column chromatography using 5% methanol/dichloromethane solution to obtain Compound XII (5.8 g, 0.013 mol, 31%) as a white solid.

$^1$H NMR (600 MHz, CDCl$_3$) δ=8.52 (s, 1H), 7.55-7.53 (m, 1H), 7.30-7.28 (m, 6H), 7.19-7.18 (m, 1H), 7.11-7.08 (m, 1H), 6.86 (s, 1H), 5.27 (t, J=6 Hz, 1H), 5.08 (s, 2H), 4.77 (m, 1H), 4.03-4.00 (m, 1H), 3.97 (t, J=4.8 Hz, 2H), 3.81-3.76 (m, 1H), 3.70 (t, J=5.1 Hz, 2H), 3.65-3.60 (m, 1H), 3.59-3.54 (m, 1H).

PREPARATION EXAMPLE 11

Preparation of Compound XIII

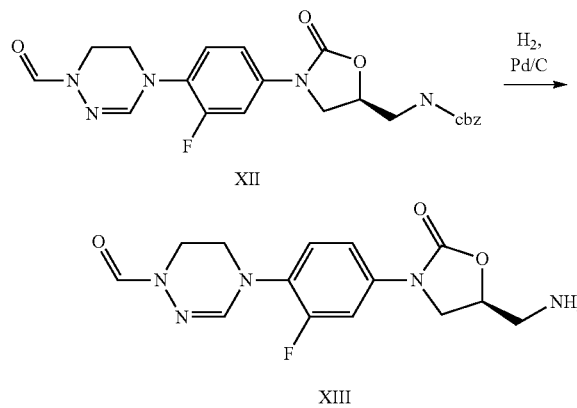

Compound XII (5 g, 0.011 mol) was dissolved in methanol (100 mL) and stirred for 4 hours under hydrogen balloon after adding Pd/C (0.5 g). The solution was filtered with celite and concentrated under reduced pressure to obtain Compound XIII (3.2 g, 0.010 mol, 91%) as a oily solid.

$^1$H NMR (600 MHz, DMSO-d$_6$) δ=8.43 (s, 1H), 7.65-7.63 (m, 1H), 7.40-7.36 (m, 2H), 7.12 (s, 1H), 4.65-4.62 (m, 1H), 4.09-4.06 (m, 1H), 3.89-3.86 (m, 1H), 3.85 (t, J=5.1 Hz, 2H), 3.70 (t, J=4.8 Hz, 2H), 2.88-2.85 (m, 1H), 2.82-2.79 (m, 1H).

PREPARATION EXAMPLE 12

Preparation of Compound XV

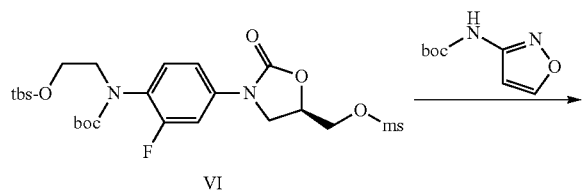

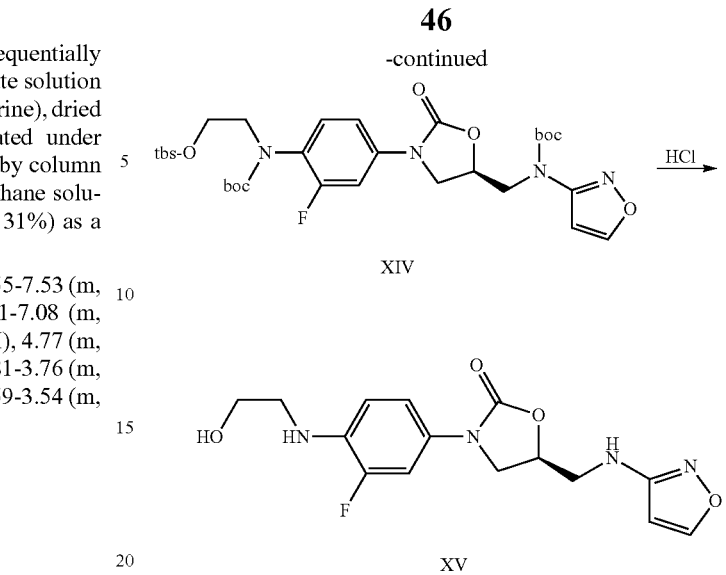

Boc-3-aminoisoxazole (1.22 g, 6.6 mmol) was dissolved in DMF (40 mL) and stirred for 30 minutes after adding 50% NaH (0.32 g, 6.6 mmol). After slowly adding Compound VI (3.6 g, 6.6 mmol) dissolved in DMF (10 mL) dropwise, the solution was stirred at 80° C. for 4 hours. The solution was cooled to room temperature, diluted with ethyl acetate, washed twice with water, dried with anhydrous sulfate, and concentrated under reduced pressure to obtain Compound XIV (4.16 g, 6.4 mmol).

Compound XIV (4.16 g, 6.4 mmol) was dissolved in dichloromethane (20 mL), stirred overnight at room temperature after adding 4 N HCl solution in dioxane (20 mL), concentrated under reduced pressure, and triturated with diethyl ether solvent to obtain Compound XV (2.2 g, 6.2 mmol, 94%) as a white solid.

$^1$H NMR (600 MHz, DMSO-d$_6$) δ 8.39 (d, J=2.2 Hz, 1H), 7.52 (dd, J$_1$=13.8 Hz, J$_2$=2.4 Hz, 1H), 7.18 (dd, J$_1$=8.4 Hz, J$_2$=1.8 Hz, 1H), 7.10 (t, J=9.3 Hz, 1H), 6.00 (d, J=2.2 Hz, 1H), 4.86 (m, 1H), 4.11 (t, J=9 Hz, 1H), 3.80-3.19 (m, 7H).

PREPARATION EXAMPLE 13

Preparation of Compound XIX

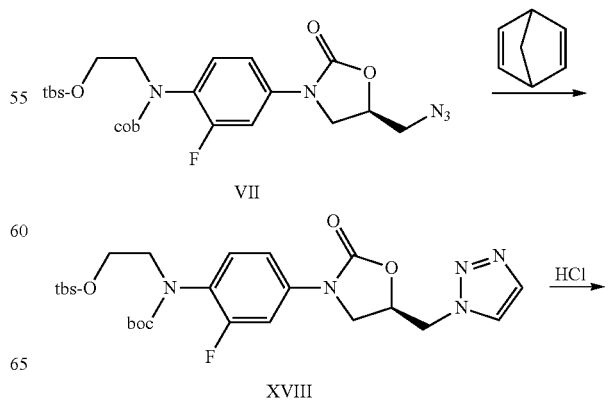

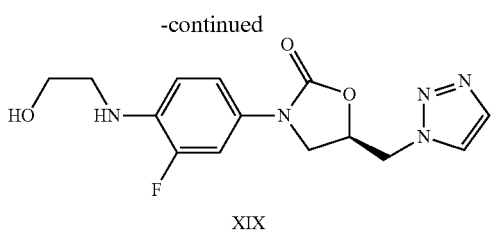

XIX

Compound VII (0.613 g, 1.2 mmol) was dissolved in dioxane (10 mL), stirred for 4 hours under reflux after adding 2,5-norbornadiene (0.6 mL, 6 mmol), and cooled to room temperature. The solution was concentrated under reduced pressure, dissolved in dichloromethane, washed with water, and dried with sodium sulfate to obtain Compound XVIII (triazole, 98%), which was treated with hydrochloric acid as in Preparation Example 9 to obtain Compound XIX (0.35 g, 1.1 mmol, 92%).

$^1$H NMR (600 MHz, DMSO-d$_6$) δ=8.18 (s, 1H), 7.77 (s, 1H), 7.39 (dd, J$_1$=13 Hz, J$_2$=2.4 Hz, 1H), 7.09-7.00 (m, 2H), 5.11 (m, 1H), 4.82 (d, J=4.8 Hz, 2H), 4.18 (t, J=9.0 Hz, 1H), 3.84 (m, 1H), 3.59 (t, J=6.0 Hz, 2H), 3.19 (t, J=6.0 Hz, 2H).

PREPARATION EXAMPLE 14

Preparation of Compound XXVII-b

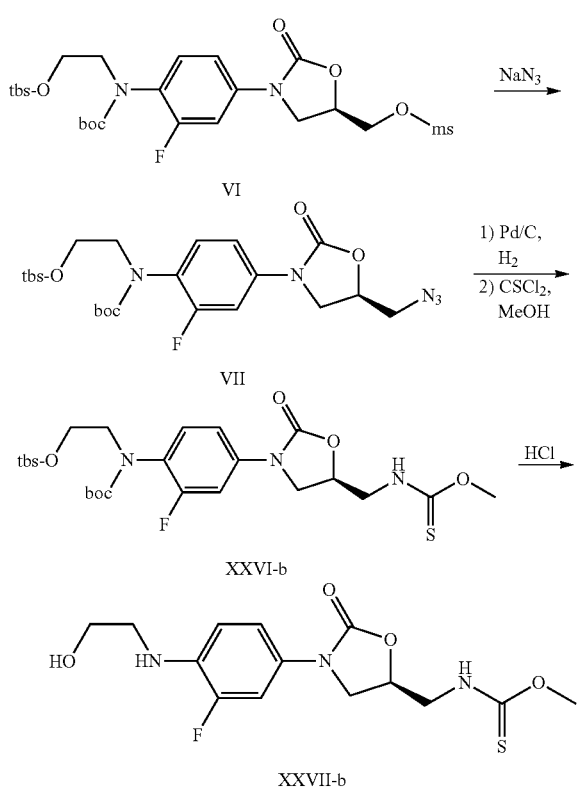

Compound VI (12 g, 21 mmol) was dissolved in DMF (100 mL) and stirred at 80° C. for 3 hours after adding NaN$_3$ (1.65 g, 26 mmol). The solution was cooled to room temperature, diluted with ethyl acetate/hexane (150 mL/30 mL), washed 3 times with distilled water (200 mL), dried with anhydrous sodium sulfate, concentrated under reduced pressure, and separated by column chromatography using 30% ethyl acetate/hexane solution to obtain Compound VII (9.6 g, 19 mmol, 89%). Compound VII (9.6 g, 19 mmol) was dissolved in methanol (120 mL), stirred for 4 hours under hydrogen balloon after adding Pd/C (1 g), and filtered with celite to obtain an amine compound (8.6 g, 95%). The amine compound (8.6 g) was dissolved in dichloromethane (120 mL) and, after adding saturated aqueous NaHCO$_3$ solution (40 mL) and then adding thiophosgene (1.6 mL, 21 mmol) at 0° C., was stirred for 2 hours. The organic layer was dried with sodium sulfate, distilled under reduced pressure, dissolved in methanol (150 mL), stirred overnight under reflux, concentrated under reduced pressure, and separated by column chromatography to obtain Compound XXVI-b (2.6 g, 7.6 mmol), which was treated with hydrochloric acid as in Preparation Example 9 to quantitatively obtain Compound XXVII-b.

$^1$H NMR (600 MHz, CDCl$_3$) δ=7.35 (dd, J$_1$=13 Hz, J$_2$=2.4 Hz, 1H), 6.99-6.89 (m, 2H), 6.70 (t, J=9.2 Hz, 1H), 4.93 (m, 1H), 4.10-3.91 (m, 6H), 3.88-3.78 (m, 3H), 3.32 (t, J=5.2 Hz, 2H).

PREPARATION EXAMPLE 15

Preparation of Compound XXVII-a

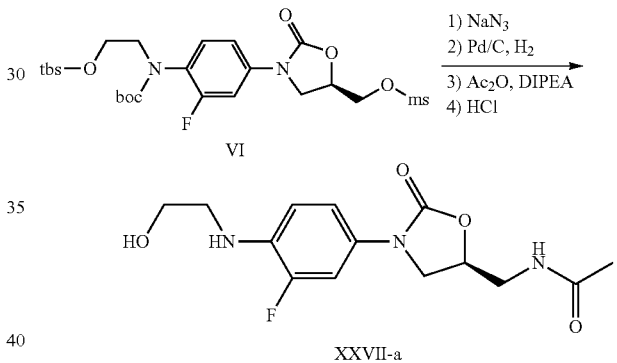

A hydrochloride of Compound XXVII-a (3.4 g, 9.8 mmol, 85%) was obtained from Compound VI as in Preparation Example 14, using Ac$_2$O instead of thiophosgene.

$^1$H NMR (600 MHz, DMSO-d$_6$) δ 7.69 (t, 1H, J=6.0 Hz), 7.46 (dd, 1H, J$_1$=13.8 Hz, J$_2$=2.4 Hz), 7.41-7.26 (m, 5H), 7.18-7.11 (m, 1H), 7.00 (t, 1H, J=9.6 Hz), 6.21-5.73 (m, 2H), 5.03 (s, 2H), 4.74-4.66 (m, 1H), 4.07 (t, 1H, J=9.0 Hz), 3.76-3.70 (m, 1H), 3.60 (t, 2H, J=5.7 Hz), 3.42-3.33 (m, 2H), 3.19 (t, 2H, J=5.7 Hz).

PREPARATION EXAMPLE 16

Preparation of Compound XXVIII-a

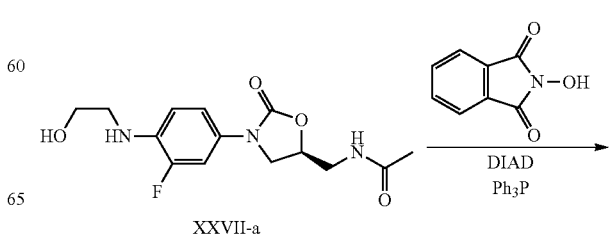

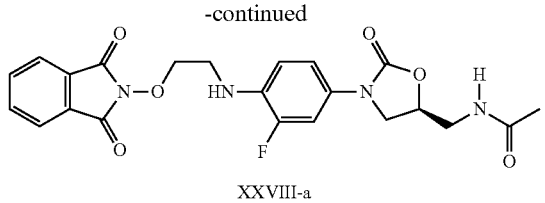

XXVIII-a

A hydrochloride of Compound XXV-a (1.69 g, 4.86 mmol), hydroxyphthalimide (0.83 g, 5.11 mmol), triphenylphosphine (1.34 g, 5.11 mmol) and triethylamine (0.7 mL, 4.87 mmol) were added to THF (20 mL). After slowly adding diisopropyl azodi-carboxylate (DIAD, 1.15 mL, 5.84 mmol) dropwise while stirring, the solution was stirred for 3 hours at room temperature. After filtration, the filtrate was concentrated under reduced pressure and separated by column chromatography to obtain Compound XXVIII-a (1.49 g, 3.26 mmol, 88%).

$^1$H NMR (400 MHz, CDCl$_3$) δ=7.86 (m, 2H), 7.76 (m, 2H), 7.38 (dd, J=8.8, 1.6 Hz, 1H), 7.00 (dd, J=8.8, 1.6 Hz, 1H), 6.69 (t, J=6.0 Hz, 1H), 6.13 (t, J=4.0 Hz), 4.92 (br, s, 1H), 4.75 (m, 1H), 4.42 (t, J=3.6 Hz, 1H), 4.00 (t, J=6 Hz, 1H), 3.70 (m, 2H), 3.60 (m, 1H), 3.50 (br, s, 2H), 2.03 (s, 3H).

LCMS: 457 (M+H$^+$) for C$_{22}$H$_{21}$FN$_4$O$_6$.

PREPARATION EXAMPLE 17

Preparation of Compound XXIII

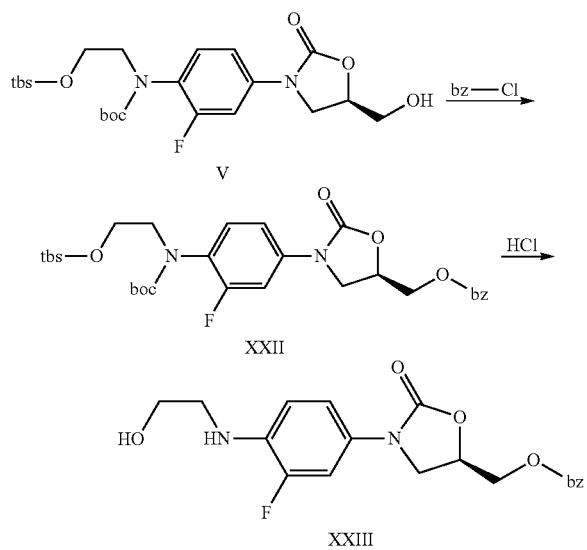

Compound V (26 g, 0.053 mol) was dissolved in dichloromethane (180 mL) and stirred for 10 minutes after slowly adding diisopropylethylamine (DIPEA, 13 mL, 0.079 mol) and benzoyl chloride (Bz-Cl, 7.4 mL, 0.064 mol) sequentially dropwise at 0° C. After heating to room temperature, followed by adding a small amount of DMAP, the solution was stirred for 2 hours. The solution was concentrated under reduced pressure, dissolved in ethyl acetate, sequentially washed with saturated aqueous sodium bicarbonate solution and saturated aqueous sodium chloride solution (brine), dried with anhydrous sodium sulfate, and concentrated under reduced pressure to quantitatively obtain Compound XXII (31 g, 0.053 mol), which was treated with hydrochloric acid as in Preparation Example 9 to quantitatively obtain Compound XXIII $^1$H NMR (600 MHz, DMSO-d$_6$) δ 7.88 (d, J=7.8 Hz, 2H), 7.63 (t, 1H, J=7.2 Hz), 7.46 (t, 2H, J=7.2 Hz), 7.41 (dd, 1H, J$_1$=13.8 Hz, J$_2$=2.4 Hz), 7.11 (d, 1H, J=9.0 Hz), 6.88 (t, 1H, J=9.0 Hz), 5.02 (m, 1H), 4.54-4.45 (m, 2H), 4.16 (t, 1H, J=9.0 Hz), 3.88 (m, 1H), 3.54 (t, 2H, J=6.0 Hz), 3.13 (t, 2H, J=6.0 Hz).

Methods for synthesizing target compounds from the intermediate prepared in Preparation Examples 1 to 17 are exemplified by the following examples.

EXAMPLE 1

Preparation of Compound 1

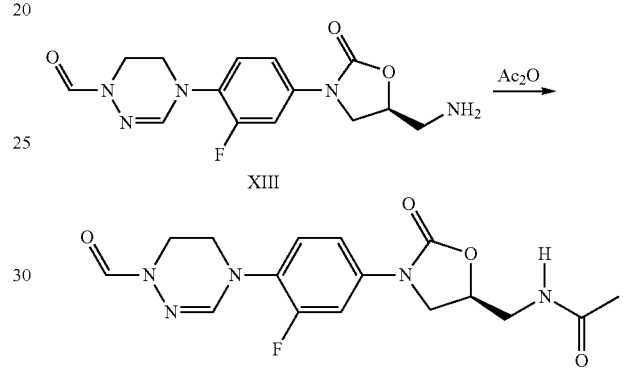

Compound XIII (0.1 g, 0.31 mmol) obtained in Preparation Example 11 was dissolved in dichloromethane (3 mL), stirred for 2 hours at room temperature after sequentially adding DIPEA (0.1 mL, 0.6 mmol) and Ac$_2$O (0.06 mL, 0.6 mmol) dropwise, concentrated under reduced pressure, and separated by column chromatography to obtain Compound 1 (0.098 g, 0.27 mmol, 87%) as a white solid.

$^1$H NMR (400 MHz, chloroform-d$_4$) δ=8.54 (s, 1H), 7.59 (dd, J=13.6, 2.4 Hz, 1H), 7.20 (dd, J=13.6, 2.4 Hz, 1H), 7.13 (t, J=8.8, Hz, 1H), 6.88 (s, 1H), 6.19 (t, J=6.0 Hz, 1H), 4.81 (m, 1H), 4.05 (t, J=8 Hz, 1H), 3.99 (t, J=4.8 Hz, 2H), 3.80 (dd, J=8.8, 6.8 Hz, 1H), 3.73 (t, J=4.8 Hz, 2H), 3.69 (m, 2H), 2.03 (s, 3H).

LCMS: 364 (M+H$^+$) for C$_{16}$H$_{18}$FN$_5$O$_4$.

EXAMPLE 2

Preparation of Compound 2

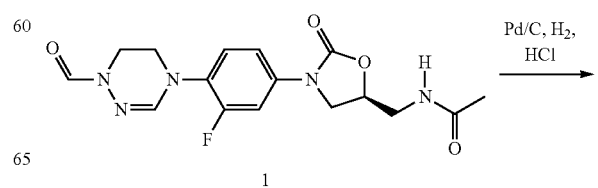

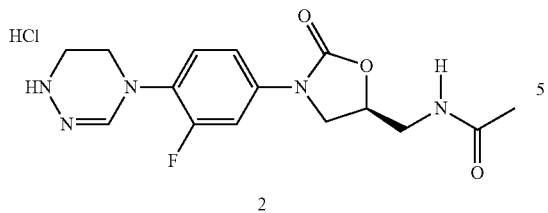

2

Compound 1 (0.7 g, 1.93 mmol), 4 N hydrochloric acid dissolved in 1,4-dioxane (3 mL, 12 mmol) and Pd/C (70 mg) were added to THF (20 mL), and stirred for 2 hours under hydrogen gas. The solution was filtered with celite and concentrated under reduced pressure to obtain Compound 2 (0.72 g, 1.93 mmol, 100%) as a white solid.

$^1$H NMR (400 MHz, DMSO-$d_6$) δ=8.34-8.31 (m, 2H), 7.68 (dd, J=13.6, 2.4 Hz, 1H), 7.56 (t, J=8.8 Hz, 1H), 7.41 (dd, J=13.6, 2.4 Hz, 1H), 4.76 (m, 1H), 4.15 (t, J=8.8 Hz, 1H), 3.78 (m, 3H), 3.46 (m, 2H), 3.35 (t, J=8.4 Hz, 2H), 1.83 (s, 3H).

LCMS: 336 (M+H$^+$) for $C_{15}H_{18}FN_5O_3$.

EXAMPLE 3

Preparation of Compound 3

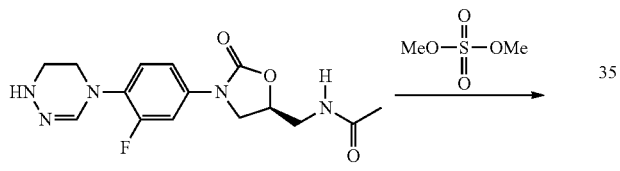

Compound 2 (0.11 g, 0.34 mmol) was dissolved in methanol (3 mL), stirred for 6 hours at room temperature after adding DIPEA (0.17 mL, 1 mmol) and dimethyl sulfate (52 mg, 0.41 mmol), and separated by column chromatography to obtain Compound 3 (29 mg, 0.083 mmol, 24%) as a white solid.

$^1$H NMR (600 MHz, chloroform-$d_1$) δ 7.52 (dd, 1H, $J_1$=13.8 Hz, $J_2$=2.4 Hz), 7.18-7.62 (m, 1H), 7.10 (t, 1H, 8.4 Hz), 6.90 (s, 1H), 6.70 (t, 1H, J=6.0 Hz), 4.82-4.75 (m, 1H), 4.04 (t, 1H, J=9.0 Hz), 3.85 (t, 2H, J=4.8 Hz), 3.82 (t, 1H, 4.8 Hz), 3.74-3.60 (m, 2H), 2.99 (t, 2H, J=4.8 Hz), 2.79 (s, 3H), 2.02 (s, 3H).

LCMS: 350 (M+H$^+$) for $C_{16}H_{20}F_1$—$N_5O_3$.

EXAMPLE 4

Preparation of Compound 4

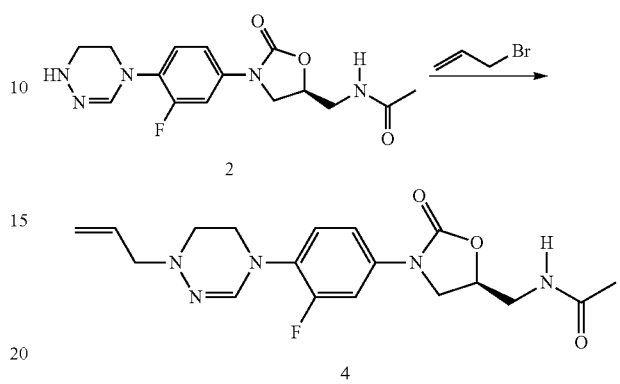

Compound 2 (0.21 g, 0.63 mmol) was dissolved in DMF (3 mL), stirred for 6 hours at room temperature after adding DIPEA (0.17 mL, 1 mmol) and allyl bromide (0.1 g, 0.8 mmol), and separated by column chromatography to obtain Compound 4 (80 mg, 0.21 mmol, 33%) as a white solid.

$^1$H NMR (600 MHz, CDCl$_3$) δ=7.51 (dd, $J_1$=13 Hz, $J_2$=2.4 Hz, 1H), 7.15-7.09 (m, 2H), 6.92 (s, 1H), 6.18 (br, t, 1H), 6.02 (m, 1H), 5.30-5.22 (m, 2H), 4.79 (m, 1H), 4.05 (t, J=9 Hz, 1H), 3.82 (t, J=4.8 Hz, 2H), 3.79-3.58 (m, 6H), 3.00 (t, J=4.8 Hz, 2H), 2.03 (s, 3H).

LCMS: 376 (M+H$^+$) for $C_{18}H_{22}F$—$_1$—$N_5O_3$.

EXAMPLE 5

Preparation of Compound 5

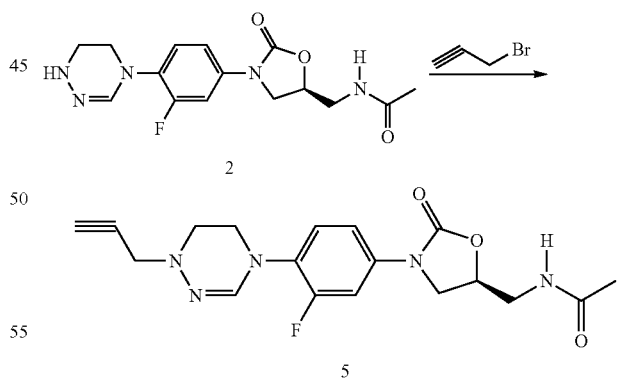

Compound 5 (34 mg, 0.091 mmol, 43%) was obtained from Compound 2 as in Example 4, using propargyl bromide.

$^1$H NMR (600 MHz, CDCl$_3$) δ=7.51 (dd, $J_1$=13 Hz, $J_2$=2.4 Hz, 1H), 7.16-7.11 (m, 2H), 6.95 (s, 1H), 6.00 (br, t, 1H), 4.79 (m, 1H), 4.04 (t, J=9 Hz, 1H), 3.85 (t, J=4.8 Hz, 2H), 3.82 (d, J=2.4 Hz, 2H), 3.79-3.62 (m, 3H), 3.13 (t, J=4.8 Hz, 2H), 2.31 (t, J=2.4 Hz, 1H), 2.03 (s, 3H).

LCMS: 374 (M+H$^+$) for $C_{18}H_{20}F$—$_1$—$N_5O_3$.

EXAMPLE 6

Preparation of Compound 6

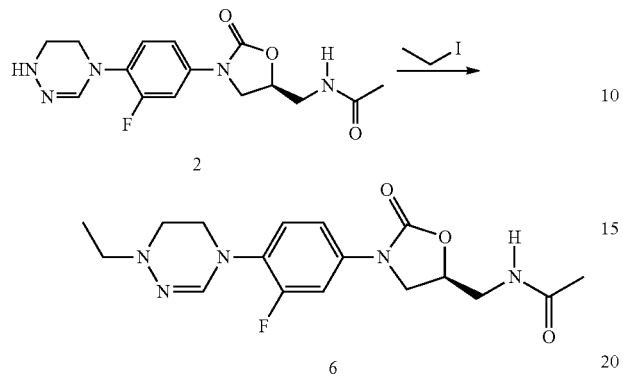

Compound 2 (30 mg, 0.08 mmol), DIPEA (66 uL, 0.40 mmol) and ethyl iodide (20 uL, 0.24 mmol) were sequentially added to dichloromethane (2 mL) at 0° C. and stirred for 8 hours under reflux. The solution was concentrated under reduced pressure and separated by column chromatography to obtain Compound 6 (5 mg, 0.01 mmol, 13%) as a yellow foam.

$^1$H NMR (400 MHz, chloroform-$d_4$) δ=7.57 (dd, J=15 Hz, 1H), 7.18 (s, 2H), 7.08 (s, 1H), 6.31 (t, J=6.0 Hz, 1H), 4.83 (m, 1H), 4.07 (t, J=8.0 Hz, 1H), 3.90 (t, J=4.2 Hz, 2H), 3.83 (dd, J=8.0, 7.2 Hz, 1H), 3.74-3.65 (m, 2H), 3.12 (t, J=5.4 Hz, 3H), 3.05 (q, J=6.6 Hz, 2H), 2.06 (s, 3H), 1.31 (t, J=6.6 Hz, 3H).

LCMS: 364 (M+H$^+$) for $C_{17}H_{22}FN_5O_3$.

EXAMPLE 7

Preparation of Compound 7

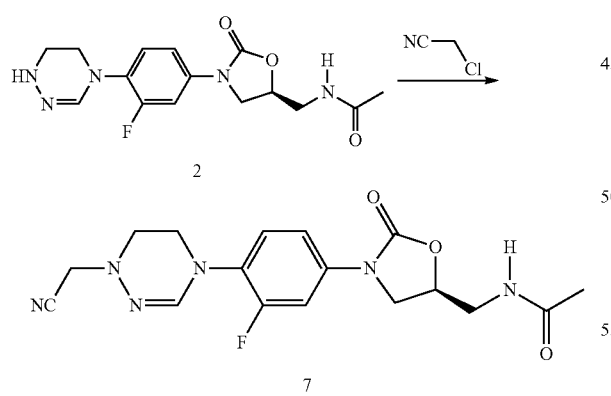

Compound 2 (0.1 g, 0.3 mmol) was dissolved in DMF (3 mL), heated for 6 hours at 80° C. after adding 1 equivalent of $K_2CO_3$, 2 equivalents of chloroacetonitrile and a catalytic amount of KI, and separated by column chromatography to obtain Compound 7 (107 mg, 0.287 mmol, 96%) as a white solid.

$^1$H NMR (600 MHz, chloroform-$d_1$) δ 7.40 (dd, 1H, $J_1$=13.2 Hz, $J_2$=2.4 Hz), 7.01 (dd, 1H, $J_1$=8.4 Hz, $J_2$=1.2 Hz), 6.69 (t, 1H, J=9.3 Hz), 6.14 (d, 1H, J=5.4 Hz), 4.78-4.72 (m 1H), 4.40 (t, 2H, J=5.4 Hz), 4.00 (t, 1H, J=9.0 Hz), 3.76-3.66 (m, 2H), 3.61 (t, 1H, J=6.0 Hz), 3.55 (t, 2H, J=5.4 Hz), 3.03 (s, 3H), 2.03 (s, 3H).

LCMS: 374 (M+H$^+$) for $C_{17}H_{19}FN_6O_3$.

EXAMPLE 8

Preparation of Compound 8

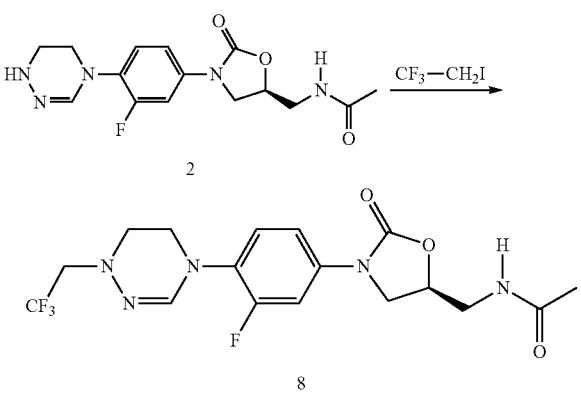

Compound 2 (0.1 g, 0.3 mmol) was dissolved in DMF (3 mL), for 6 hours at 200° C. after adding 1 equivalent of $K_2CO_3$ and 2 equivalents of 1,1,1-trifluoro-2-iodoethane, and separated by column chromatography to obtain Compound 8 (11 mg, 0.026 mmol, 9%) as a white solid.

$^1$H NMR (600 MHz, chloroform-$d_1$) δ 7.52 (dd, 1H, $J_1$=13.8 Hz, $J_2$=2.4 Hz), 7.18-7.07 (m, 2H), 6.86 (s, 1H), 6.32-6.24 (m, 1H), 4.90-4.76 (m, 1H), 4.04 (t, J=8.7 Hz), 3.84 (t, 2H, J=4.5 Hz), 3.81-3.76 (m, 1H), 3.62-3.52 (m, 2H), 3.24 (t, 4.5 Hz), 2.02 (s, 3H).

LCMS: 418 (M+H$^+$) for $C_{17}H_{19}F_4N_5O_3$.

EXAMPLE 9

Preparation of Compound 9

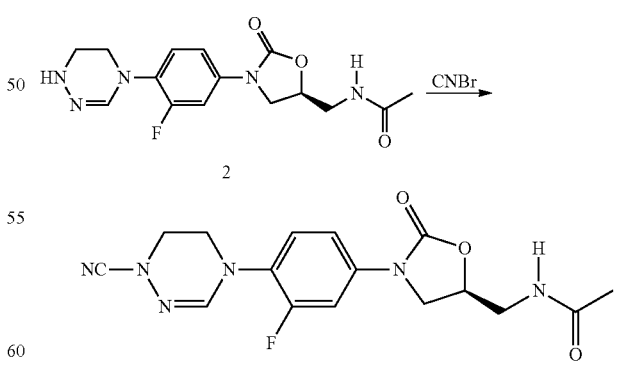

Compound 2 (150 mg, 0.40 mmol), DIPEA (200 uL, 1.20 mmol) and cyanogen bromide (63 mg, 0.60 mmol) were sequentially added to dichloromethane (2 mL) at 0° C. and stirred for 0.5 hour. The solution was concentrated under reduced pressure and separated by column chromatography to obtain Compound 9 (25 mg, 0.07 mmol, 17%) as a white solid.

¹H NMR (400 MHz, chloroform-d₄) δ=7.60 (dd, J=13.2, 2.4 Hz, 1H), 7.20 (dd, J=13.2, 2.4 Hz, 1H), 7.13 (t, J=8.8, Hz, 1H), 6.89 (s, 1H), 4.80 (m, 1H), 4.05 (t, J=9.2 Hz, 1H), 3.85-3.61 (m, 2H), 2.03 (s, 3H).

LCMS: 361 (M+H⁺) for $C_{16}H_{17}FN_6O_3$.

EXAMPLE 10

Preparation of Compound 10

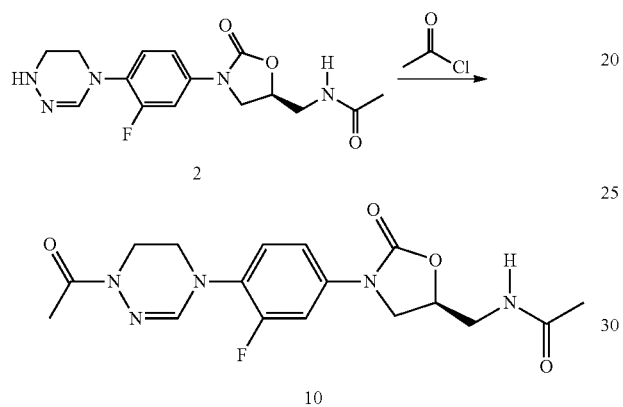

Compound 2 (5 mg, 0.013 mmol), DIPEA (4 uL, 0.026 mmol) and acetyl chloride (1.5 uL, 0.02 mmol) were sequentially added to dichloromethane (2 mL) at 0° C. and stirred for 1.5 hours. After adding dichloromethane (30 mL), the solution was washed with saturated aqueous sodium bicarbonate solution (15 mL), dried with magnesium sulfate, concentrated under reduced pressure, and separated by column chromatography to obtain Compound 10 (2 mg, 0.004 mmol, 30%) as a white solid.

¹H NMR (600 MHz, chloroform-d₄) δ=7.57 (dd, J=13.2, 2.4 Hz, 1H), 7.20 (dd, J=9.6, 2.4 Hz, 1H), 7.13 (t, J=9.6, Hz, 1H), 6.85 (s, 1H), 6.03 (t, J=6.0 Hz, 1H), 4.80 (m, 1H), 4.06 (m, 2H), 3.79 (dd, J=9.0, 6.6 Hz, 2H), 3.71 (m, 2H), 3.62 (m, 1H) 2.03 (s, 3H).

LCMS: 378 (M+H⁺) for $C_{17}H_{20}FN_5O_4$.

EXAMPLE 11

Preparation of Compound 11

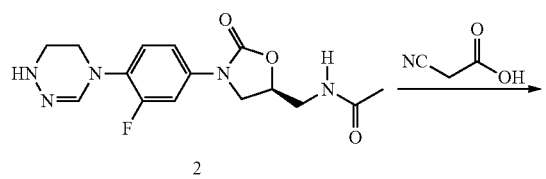

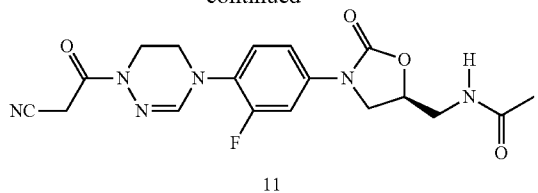

Compound 2 (30 mg, 0.08 mmol), (1H-benzotriazol-1-yloxy)tripyrrolidinophosphonium hexafluorophosphate (PyBOP, 105 mg, 0.20 mmol), cyanoacetic acid (14 mg, 0.16 mmol) and DIPEA (40 uL, 0.24 mmol) were sequentially added to DMF (2 mL) at 0° C. and stirred for 1.5 hours at room temperature. After adding dichloromethane (30 mL), the solution was washed 3 times with saturated aqueous sodium bicarbonate solution, dried with magnesium sulfate, concentrated under reduced pressure, and separated by column chromatography to obtain Compound 11 (5 mg, 0.01 mmol, 13%) as a white solid.

¹H NMR (400 MHz, chloroform-d₄) δ=7.61 (dd, J=13.2, 2.8 Hz, 1H), 7.25 (dd, J=13.2, 2.8 Hz, 1H), 7.13 (t, J=8.8, Hz, 1H), 6.85 (s, 1H), 6.19 (t, J=6.0 Hz, 1H), 4.81 (m, 1H), 4.07 (m, 2H), 3.85 (m, 3H), 3.75 (t, J=6.0 Hz, 2H), 3.68 (m, 2H), 2.03 (s, 3H).

LCMS: 403 (M+H⁺) for $C_{18}H_{19}FN_6O_4$.

EXAMPLE 12

Preparation of Compound 12

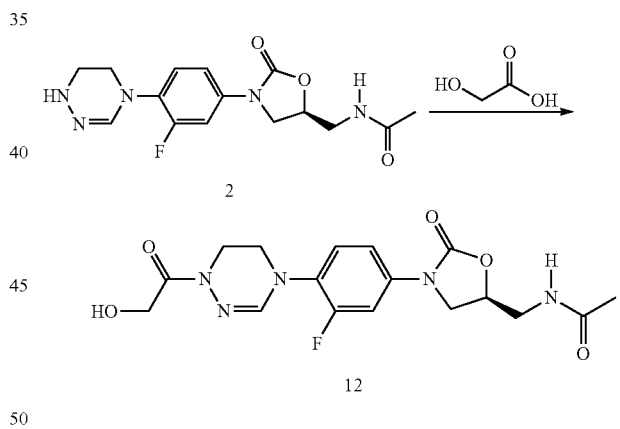

Compound 2 (200 mg, 0.54 mmol), PyBOP (700 mg, 1.34 mmol), glycolic acid (82 mg, 1.07 mmol) and DIPEA (266 uL, 1.61 mmol) were sequentially added to DMF (2 mL) at 0° C. and stirred for 2 hours at room temperature. After adding dichloromethane (100 mL), the solution was washed 3 times with distilled water, dried with magnesium sulfate, concentrated under reduced pressure, and separated by column chromatography to obtain Compound 12 (83 mg, 0.21 mmol, 39%) as a white solid.

¹H NMR (400 MHz, DMSO-d₆) δ=8.25 (t, J=6 Hz, 1H), 7.62 (dd, J=8.8, 2.4 Hz, 1H), 7.37 (t, J=8.8 Hz, 1H), 7.32 (dd, J=8.8, 2.4 Hz, 1H), 7.07 (t, J=2.0 Hz, 1H), 4.74 (m, 1H), 4.53 (t, J=6.0 Hz, 1H), 4.32 (d, J=6 Hz, 2H), 4.12 (t, J=8.8 Hz, 1H), 3.89 (t, J=4.6 Hz, 2H), 3.75-3.69 (m, 3H), 3.40 (m, 2H), 1.83 (s, 3H).

LCMS: 394 (M+H⁺) for $C_{17}H_{20}FN_5O_5$.

EXAMPLE 13

Preparation of Compound 13

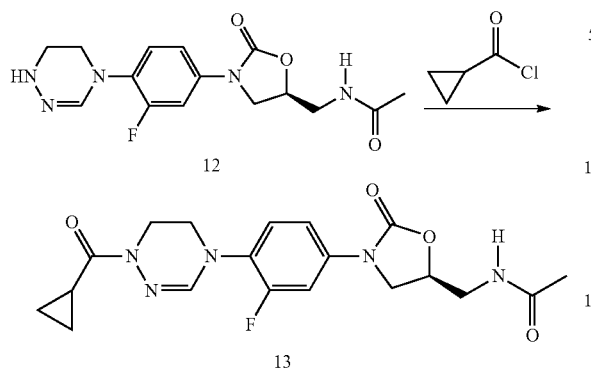

Compound 2 (35 mg, 0.09 mmol), DIPEA (45 uL, 0.28 mmol) and cyclo-propanecarbonyl chloride (13 uL, 0.14 mmol) were sequentially added to dichloromethane (3 mL) at 0° C. and stirred for 1 hour at room temperature. The solution was concentrated under reduced pressure and separated by column chromatography to obtain Compound 13 (13 mg, 0.03 mmol, 33%) as a white solid.

$^1$H NMR (600 MHz, DMSO-d$_6$) δ=8.25 (t, J=6 Hz, 1H), 7.6 (d, J=13.8 Hz, 1H), 7.39 (t, J=9.0 Hz, 1H), 7.32 (d, J=13.8 Hz, 1H), 7.10 (m, 1H), 4.75 (m, 1H), 4.12 (t, J=9.0 Hz, 1H), 3.90 (s, 2H), 3.74 (t, J=6.6 Hz, 1H), 3.70 (s, 2H), 3.42 (t, J=5.4 Hz, 2H), 2.69 (t, J=6.0 Hz, 1H), 1.83 (s, 3H), 0.85 (d, J=6.0 Hz, 3H).

LCMS: 404 (M+H$^+$) for C$_{19}$H$_{22}$FN$_5$O$_4$.

EXAMPLE 14

Preparation of Compound 14

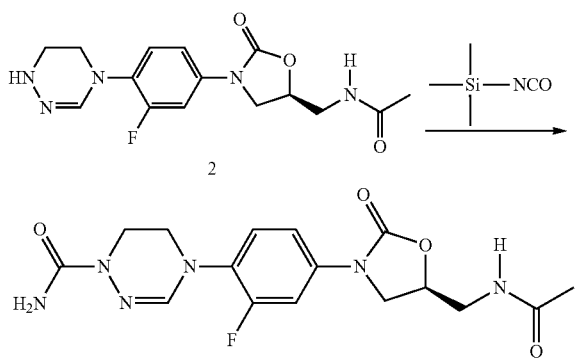

Compound 2 (30 mg, 0.08 mmol), triethylamine (23 uL, 0.16 mmol) and trimethylsilyl isocyanate (63 uL, 0.40 mmol) were sequentially added to dichloromethane (3 mL) at 0° C. and stirred for 2 hours at room temperature. After adding dichloromethane (30 mL), the solution was washed twice with saturated aqueous sodium bicarbonate solution, dried with magnesium sulfate, concentrated under reduced pressure, and separated by column chromatography to obtain Compound 14 (8 mg, 0.02 mmol, 26%) as a white solid.

$^1$H NMR (400 MHz, DMSO-d$_6$) δ=8.26 (t, J=6.0 Hz, 1H), 7.60 (dd, J=15.0, 2.4 Hz, 1H), 7.37-7.30 (m, 2H), 6.96 (d, J=2.0 Hz, 1H), 6.32 (s, 2H), 4.74 (m, 1H), 4.12 (t, J=8.8 Hz, 1H), 3.78-3.67 (m, 4H), 3.40-3.28 (m, 3H), 1.83 (s, 3H).

LCMS: 379 (M+H$^+$) for C$_{16}$H$_{23}$FN$_6$O$_4$.

EXAMPLE 15

Preparation of Compound 15

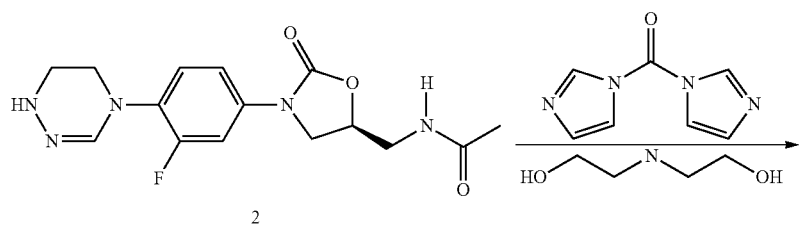

Compound 15 (25 mg, 0.059 mmol, 42%) was obtained from Compound 2 as in Example 6, using carbonyldiimidazole (437 mg, 2.7 mmol) and ethanolamine.

$^1$H NMR (600 MHz, chloroform-d$_1$) δ 7.69 (s, 1H), 7.54 (dd, 1H, J$_1$=13.2 Hz, J$_2$=2.4 Hz), 7.16 (dd, 1H, J$_1$=9.0 Hz, J$_2$=1.8 Hz), 7.10-7.08 (m, 1H), 6.87 (t, 1H, J=6.0 Hz), 6.78 (s, 1H), 6.72 (t, 1H, J=6.0 Hz), 4.83-7.49 (m, 1H), 4.04 (t, 1H, J=9.0 Hz), 3.95 (t, 2H, J=4.8 Hz), 3.84-3.78 (m, 1H), 3.76 (t, 2H, J=5.4 Hz), 3.72 (t, 2H, J=4.8 Hz), 3.67 (dd, 2H, J$_1$=6.0 Hz, J$_2$=4.8 Hz), 2.03 (s, 3H).

LCMS: 423 (M+H$^+$) for C$_{18}$H$_{23}$FN$_6$O$_5$.

EXAMPLE 16

Preparation of Compound 16

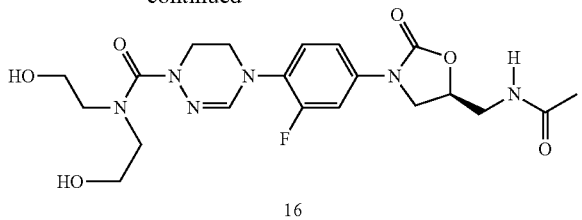

16

Compound 16 (15 mg, 0.032 mmol, 25%) was obtained from Compound 2 as in Example 15, using carbonyldiimidazole and diethanolamine.

$^1$H NMR (600 MHz, DMSO-d$_6$) δ 7.70-7.62 (m, 1H), 7.37-7.30 (m, 2H), 7.1 (s, 1H), 4.81-4.76 (m, 1H), 4.45-4.40 (m, 2H), 4.14 (t, 1H, J=9.0 Hz), 4.01-3.94 (m, 2H), 3.82-3.78 (m, 4H), 3.55 (d, 2H, J=4.8 Hz), 3.48-3.42 (m, 1H), 3.42-3.38 (m, 2H), 3.20-3.16 (m, 2H), 1.94 (s, 3H), 1.29 (t, 2H, J=7.2 Hz).

LCMS: 467 (M+H$^+$) for C$_{20}$H$_{27}$FN$_6$O$_6$.

EXAMPLE 17

Preparation of Compound 17

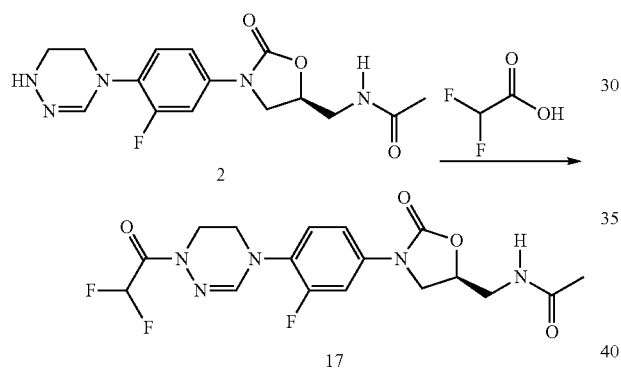

Compound 17 (31 mg, 0.075 mmol, 88%) was obtained from Compound 2 as in Example 11, using difluoroacetic acid.

$^1$H NMR (600 MHz, chloroform-d$_1$) δ 7.61 (dd, 1H, J$_1$=13.2 Hz, J$_2$=3.0 Hz), 7.22 (dd, 1H, J$_1$=9.0 Hz, J$_2$=2.4 Hz), 7.14 (t, 1H, J=9.0 Hz), 6.90 (s, 1H), 6.77 (t, 1H, J=53.4 Hz), 6.04 (t, 1H, J=6.3 Hz), 4.83-4.79 (m, 1H), 4.08 (t, 2H, J=4.8 Hz), 4.05 (t, 1H, J=9.0 Hz), 3.88-3.80 (m, 1H), 3.78 (t, 2H, J=4.8 Hz), 3.75-3.69 (m, 1H), 3.69-3.60 (m, 1H), 2.03 (s, 3H).

LCMS: 414 (M+H$^+$) for C$_{17}$H$_{18}$F$_3$N$_5$O$_4$.

EXAMPLE 18

Preparation of Compound 18

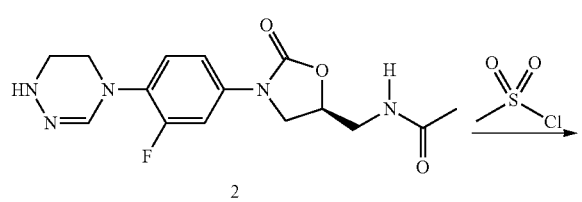

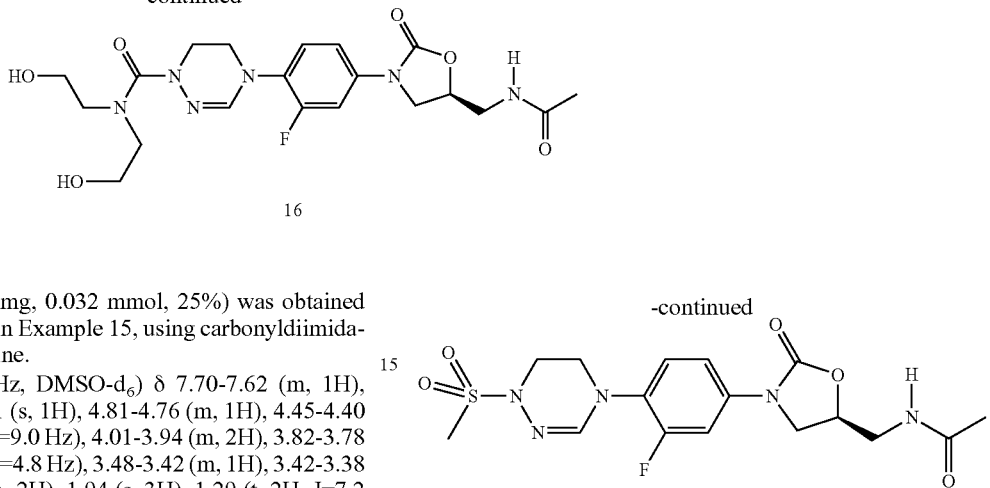

18

Compound 2 (35 mg, 0.09 mmol), DIPEA (45 uL, 0.28 mmol) and methanesulfonyl chloride (11 uL, 0.14 mmol) were sequentially added to dichloromethane (3 mL) at 0° C. and stirred for 1 hour at room temperature. The solution was concentrated under reduced pressure and separated by column chromatography to obtain Compound 18 (13 mg, 0.03 mmol, 33%) as a white solid.

$^1$H NMR (600 MHz, DMSO-d$_6$) δ=8.26 (t, J=5.4 Hz, 2H), 7.61 (d, J=13.8 Hz, 1H), 7.43 (t, J=9.6 Hz, 1H), 7.33 (d, J=9.6 Hz, 1H), 7.21 (s, 1H), 4.75 (m, 1H), 4.13 (t, J=8.4 Hz, 1H), 3.84 (s, 1H), 3.74 (t, J=8.4 Hz, 1H), 3.56 (s, 2H), 3.41 (t, J=5.4 Hz, 2H), 2.98 (s, 3H), 1.83 (s, 3H).

LCMS: 414 (M+H$^+$) for C$_{16}$H$_{20}$FN$_5$O$_5$S.

EXAMPLE 19

Preparation of Compound 19

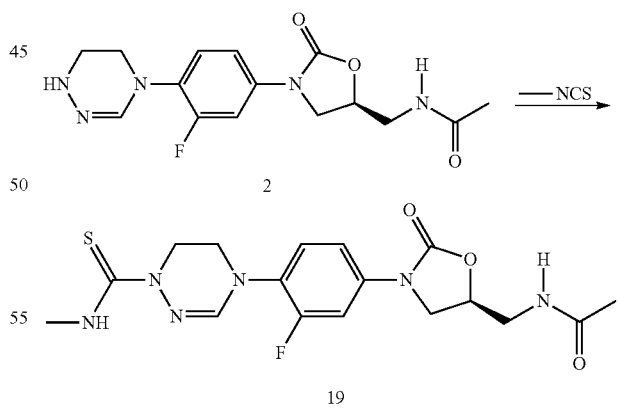

Compound 2 (30 mg, 0.08 mmol), DIPEA (66 uL, 0.40 mmol) and methyl isothiocyanide (6 uL, 0.24 mmol) were sequentially added to dichloromethane (2 mL) at 0° C. and stirred for 12 hours. The solution was concentrated under reduced pressure and separated by column chromatography to obtain Compound 19 (17 mg, 0.03 mmol, 38%) as a white solid.

¹H NMR (600 MHz, chloroform-d₄) δ=7.78 (s, 1H), 7.58 (dd, J=13.2, 2.4 Hz, 1H), 7.21 (dd, J=13.2, 2.4 Hz, 1H), 7.13 (t, J=8.4, Hz, 1H), 6.86 (s, 1H), 5.96 (t, J=6.0 Hz, 1H), 4.80 (m, 1H), 4.59 (t, J=5.4 Hz, 2H), 4.05 (t, J=7.5 Hz, 1H), 3.81-3.77 (m, 3H), 3.71 (m, 1H), 3.65 (m, 1H), 3.20 (d, J=4.8 Hz, 1H), 2.03 (s, 3H).

LCMS: 409 (M+H⁺) for $C_{17}H_{21}FN_6O_3S$.

EXAMPLE 20

Preparation of Compound 20

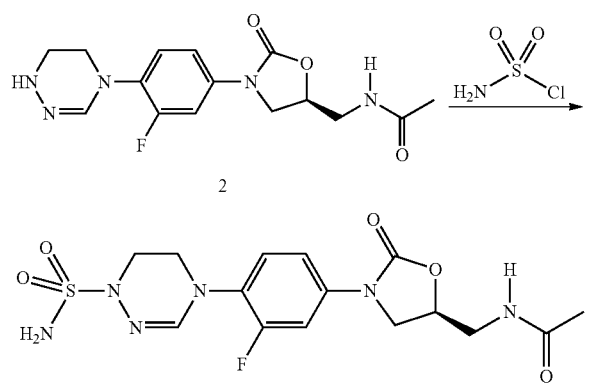

Compound 2 (50 mg, 0.13 mmol), triethylamine (55 uL, 0.39 mmol) and amido-sulfonyl chloride (145 uL, 0.26 mmol) were sequentially added to dichloromethane (3 mL) at 0° C. and stirred for 12 hours at room temperature. After adding dichloromethane (30 mL), the solution was washed twice with saturated aqueous sodium bicarbonate solution, dried with magnesium sulfate, concentrated under reduced pressure, and separated by column chromatography to obtain Compound 20 (5 mg, 0.01 mmol, 10%) as a white solid.

¹H NMR (400 MHz, DMSO-d₆) δ=8.26 (t, J=4.8 Hz, 1H) 7.60 (dd, J=13.2, 2.4 Hz, 1H), 7.42 (t, J=8.8 Hz, 1H), 7.32 (dd, J=13.2, 2.4 Hz, 1H), 7.12 (s, 1H), 7.05 (s, 2H), 4.74 (m, 1H), 4.12 (t, J=9.2 Hz, 1H), 3.81 (t, J=5.2 Hz, 2H), 3.73 (dd, J=9.2, 6.4 Hz, 1H), 3.50-3.38 (m, 4H), 1.83 (s, 3H).

LCMS: 414 (M+H⁺) for $C_{15}H_{19}FN_6O_5S$.

EXAMPLE 21

Preparation of Compound 21

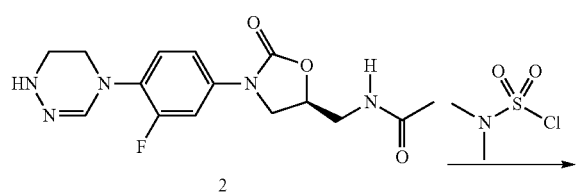

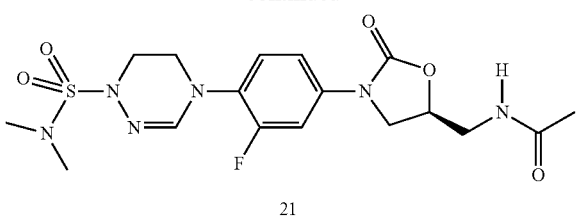

Compound 2 (50 mg, 0.13 mmol), triethylamine (36 uL, 0.26 mmol) and dimethylaminosulfonyl chloride (16 uL, 0.15 mmol) sequentially added to DMF (1 mL) at 0° C. and stirred for 12 hours at room temperature. After adding dichloromethane (30 mL), the solution was washed twice with saturated aqueous sodium bicarbonate solution (10 mL), dried with magnesium sulfate, concentrated under reduced pressure, and separated by column chromatography to obtain Compound 21 (6 mg, 0.01 mmol, 10%) as a white solid.

¹H NMR (400 MHz, DMSO-d₆) δ=7.62 (dd, J=13.2, 2.4 Hz, 1H), 7.19 (dd, J=13.2, 2.0 Hz, 1H), 7.12 (t, J=8.8 Hz, 1H), 6.94 (s, 1H), 6.00 (t, J=6.0 Hz, 1H), 4.80 (m, 1H), 4.05 (t, J=8.8 Hz, 1H), 3.85 (t, J=4.4 Hz, 2H), 3.79 (dd, J=8.8, 6.8 Hz, 1H), 3.71-3.60 (m, 4H), 3.03 (s, 6H), 2.03 (s, 3H).

LCMS: 443 (M+H⁺) for $C_{17}H_{23}FN_6O_5$.

EXAMPLE 22

Preparation of Compound 22

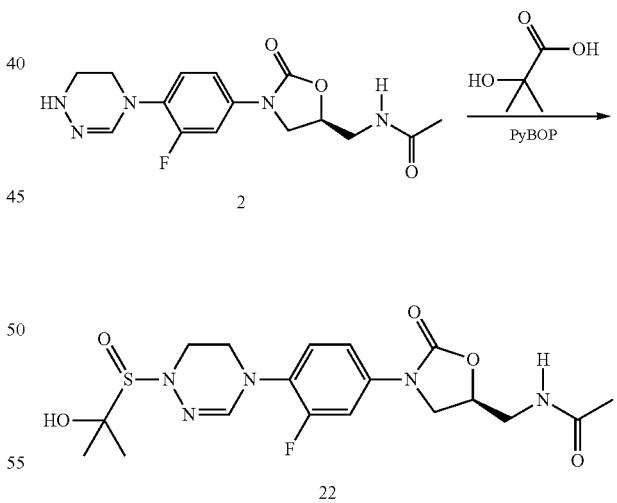

Compound 22 (36 mg, 0.085 mmol, 78%) was obtained from Compound 2 as in Example 11.

¹H NMR (400 MHz, DMSO-d₆) δ=8.26 (t, J=6.0 Hz, 1H), 7.50 (d, J=13.8 Hz, 1H), 7.37 (t, J=9.0 Hz, 1H), 7.24 (d, J=9.0 Hz, 1H), 5.86 (s, 1H), 5.61 (m, 1H), 4.72 (m, 1H), 4.11 (m, 1H), 3.72 (m, 1H), 3.41-3.35 (m, 2H), 3.08 (m, 2H), 2.86 (m, 2H), 1.83 (s, 3H), 1.31 (s, 3H), 1.24 (s, 3H).

LCMS: 422 (M+H⁺) for $C_{19}H_{24}FN_5O_5$.

EXAMPLE 23

Preparation of Compound 23

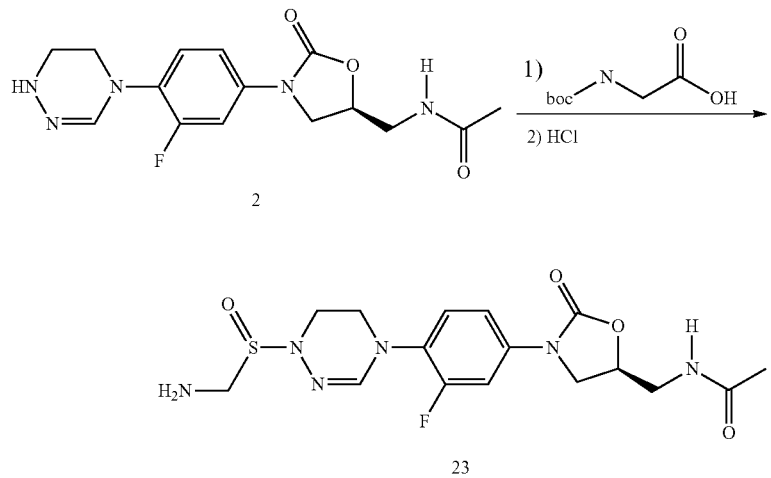

Compound 2 (30 mg, 0.08 mmol), PyBOP (105 mg, 0.20 mmol), Boc-Gly-OH (28 mg, 0.16 mmol) and DIPEA (40 uL, 0.24 mmol) were sequentially added to DMF (2 mL) 0° C. and stirred for 1.5 hours at room temperature. After adding dichloromethane (30 mL), the solution was washed 3 times with distilled water (10 mL), dried with magnesium sulfate, concentrated under reduced pressure, separated by column chromatography, and stirred for 0.5 hour after adding 4 N hydrochloric acid dissolved in 1,4-dioxane (3 mL). The product was concentrated under reduced pressure to obtain Compound 23 (10 mg, 0.02 mmol, 29%).

$^1$H NMR (400 MHz, DMSO-d$_6$) δ=8.29 (t, J=6 Hz, 1H), 8.10 (s, 3H), 7.62 (dd, J=15.0, 2.4 Hz, 1H), 7.40 (t, J=8.8 Hz, 1H), 7.34 (dd, J=15.0, 2.4 Hz, 1H), 7.20 (s, 1H), 4.74 (m, 1H), 4.13 (t, J=8.8 Hz, 1H), 3.99-3.94 (m, 3H), 3.74 (t, J=4.0 Hz, 2H), 3.42 (t, J=4.8 Hz, 2H), 1.83 (s, 3H).

LCMS: 393 (M+H$^+$) for C$_{17}$H$_{21}$FN$_6$O$_4$.

EXAMPLE 24

Preparation of Compound 24

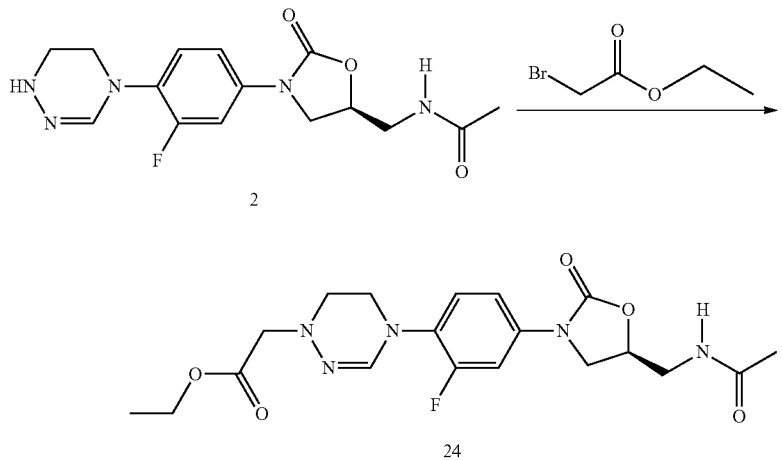

Compound 24 (200 mg, 0.48 mmol, 34%) was obtained from Compound 2 as in Example 7, using ethyl bromoacetate.

$^1$H NMR (600 MHz, chloroform-d$_1$) δ 7.50 (dd, 1H, J$_1$=13.8 Hz, J$_2$=2.4 Hz), 7.13 (dd, 1H, J$_1$=9.0 Hz, J$_2$=2.4 Hz), 7.10 (t, 1H, J=8.4 Hz), 6.89 (s, 1H), 6.70 (t, 1H, J=6.0 Hz), 4.82-4.79 (m, 1H), 4.25-4.21 (m, 2H), 4.04 (t, 1H, J=9.0 Hz), 3.84 (t, 2H, J=4.2 Hz), 3.82-3.80 (m, 1H), 3.77 (s, 2H), 3.66 (t, 2H, J=4.2 Hz), 3.24 (t, 2H, J=4.2 Hz), 2.02 (s, 3H).

LCMS: 422 (M+H$^+$) for C$_{19}$H$_{24}$FN$_5$O$_5$.

EXAMPLE 25

Preparation of Compound 25

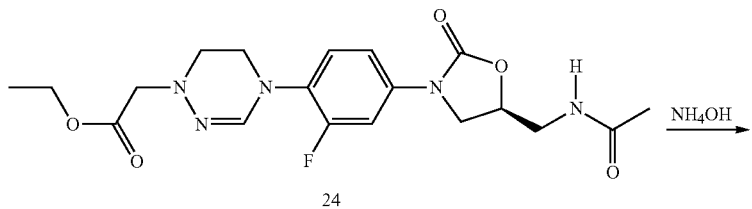

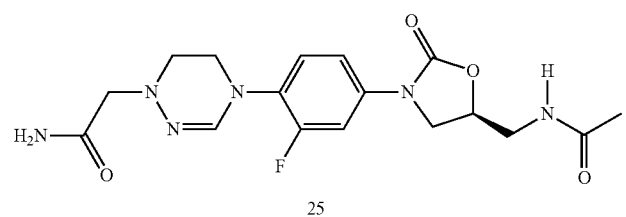

Compound 24 (100 mg, 0.24 mmol) was dissolved in methanol (2 mL), stirred overnight at 100° C. in a sealed tube after adding ammonia water (0.5 mL), concentrated under reduced pressure, and separated by column chromatography to obtain Compound 25 (20 mg, 0.051 mmol, 21%).

$^1$H NMR (400 MHz, DMSO-$d_6$) δ 8.25 (t, 1H, J=5.6 Hz), 7.56 (d, 1H, 14.0 Hz), 7.83-7.26 (m, 2H), 7.21-7.08 (m, 2H), 6.91 (s, 1H), 4.75-4.71 (m, 1H), 4.11 (t, 1H, J=9.0 Hz), 3.82-3.69 (m, 3H), 3.50-3.40 (m, 2H), 3.31 (s, 2H), 3.03 (t, 2H, J=4.4 Hz), 1.83 (s, 3H).

LCMS: 393 (M+H$^+$) for $C_{17}H_{21}FN_6O_4$.

EXAMPLE 26

Preparation of Compound 26

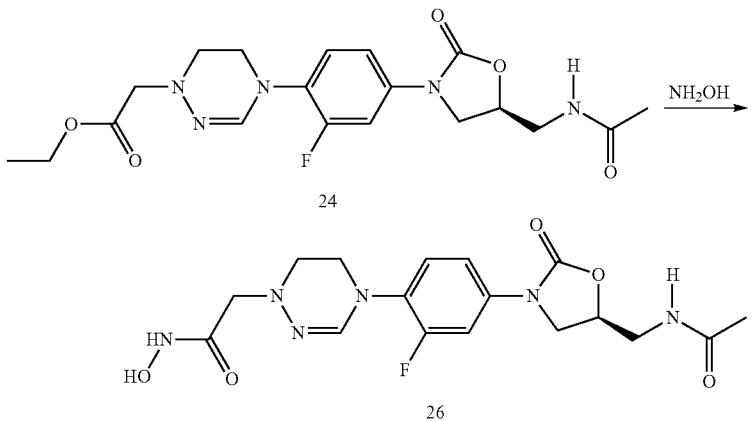

Compound 24 (100 mg, 0.24 mmol) was dissolved in methanol (20 mL), stirred overnight at room temperature after adding hydroxylamine solution (obtained by adding 2.4 g of KOH to 2.4 g of NH$_2$OH—HCl and then filtering) dissolved in methanol (20 mL), concentrated under reduced pressure, and separated by column chromatography to obtain Compound 26 (22 mg, 0.054 mmol, 23%).

$^1$H NMR (600 MHz, DMSO-$d_6$) δ 8.30-8.20 (m, 1H), 7.35-7.25 (m, 1H), 7.10-7.00 (m, 1H), 6.87 (s, 1H), 5.33-5.28 (m, 1H), 4.71-7.64 (m, 1H), 4.11 (t, 2H, J=9.0 Hz), 4.04 (t, 2H, J=8.4 Hz), 3.17 (s, 2H), 2.91 (t, 2H, J=6.6 Hz), 1.83 (s, 1H).

LCMS: 409 (M+H$^+$) for $C_{17}H_{21}FN_6O_5$.

EXAMPLE 27

Preparation of Compound 27

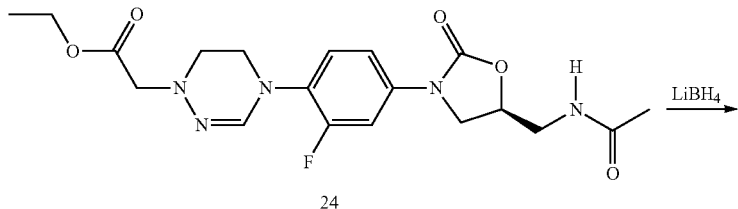

24

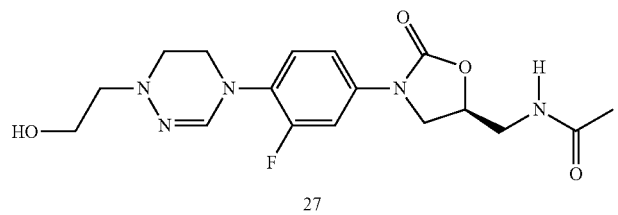

27

Compound 24 (110 mg, 0.26 mmol) was dissolved in THF (10 mL) and stirred for 3 hours at room temperature after adding 2M LiBH$_4$ solution (0.2 mL, 0.4 mmol). After adding a small amount of water, the solution was separated by column chromatography to obtain Compound 27 (24 mg, 0.063 mmol, 29%) as a light yellow solid.

$^1$H NMR (600 MHz, chloroform-d$_1$) δ 7.54 (dd, 1H, J$_1$=13.8 Hz, J$_2$=2.4 Hz), 7.16 (dd, 1H, J$_1$=9.0 Hz, J$_2$=2.4 Hz), 7.12 (t, 1H, J=8.4 Hz), 6.90 (s, 1H), 5.98 (t, 1H, J=6.0 Hz), 4.87 (m, 1H), 4.05 (t, 1H, J=9.0 Hz), 3.97 (m, 2H), 3.85 (t, 2H, J=4.2 Hz), 3.82-3.6 (m, 3H), 3.07 (t, 2H, J=4.2 Hz), 3.00 (m, 2H), 2.04 (s, 3H).

LCMS: 380 (M+H$^+$) for C$_{17}$H$_{22}$FN$_5$O$_4$.

EXAMPLE 28

Preparation of Compound 28

Compound XXVIII-a (0.22 g, 0.49 mmol) and hydrazine (monohydrate, 1 mL) were dissolved in methanol (10 mL), stirred for 2 hours under reflux, concentrated under reduced pressure, and stirred for 4 hours under reflux after adding trimethyl orthoformate (5 mL) and acetic acid (5 mL). The solution was concentrated under reduced pressure and separated by column chromatography to obtain Compound 28 (32 mg, 0.10 mmol, 20%) as a white solid.

$^1$H NMR (400 MHz, DMSO-d$_6$) δ=8.25 (t, J=6 Hz, 1H), 7.60 (dd, J=14.0, 2.4 Hz, 1H), 7.46 (s, 1H), 7.38 (t, J=8.8 Hz, 1H), 7.31 (dd, J=9.2, 2.0 Hz, 1H), 4.74 (m, 1H), 4.12 (t, J=9.2 Hz, 1H), 4.04 (t, J=3.6 Hz, 2H), 3.75-3.67 (m, 3H), 3.41 (t, J=5.6 Hz, 2H), 1.83 (s, 3H).

LCMS: 337 (M+H$^+$) for C$_{15}$H$_{17}$FN$_4$O$_4$.

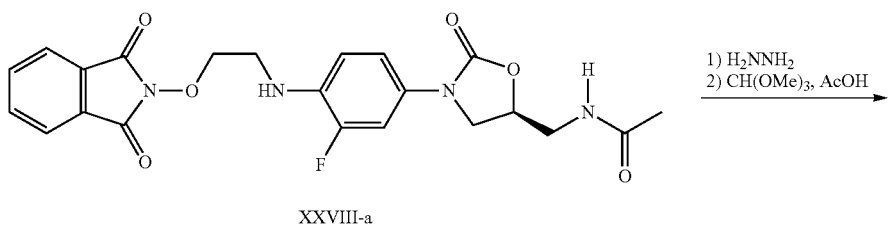

XXVIII-a

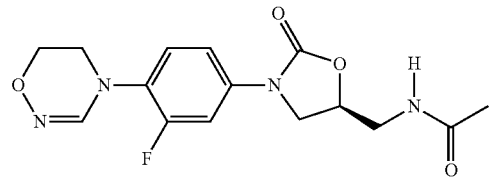

28

EXAMPLE 29

Preparation of Compound 29

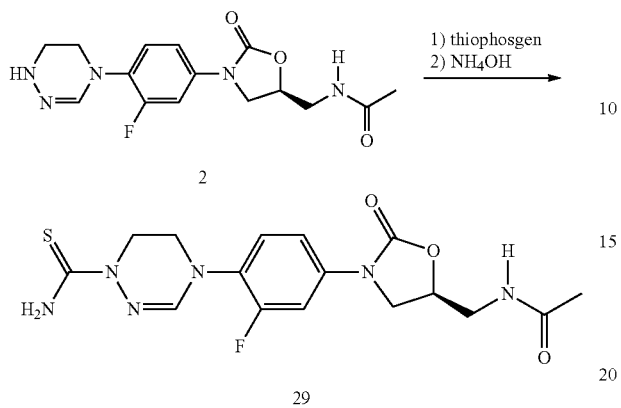

Compound 2 (100 mg, 0.27 mmol) was dissolved in chloroform (3 mL) and stirred for 30 minutes after adding saturated aqueous NaHCO$_3$ solution (3 mL) and then adding thiophosgene (0.021 mL) at 0° C. The organic layer was separated and ammonia water (1 mL) was added. The solution was diluted with THF (10 mL) and distilled under reduced pressure to remove the quantity of the solvent in half. After further adding ammonia water (2 mL), the solution was stirred overnight at room temperature. The solution was distilled under reduced pressure and triturated with ethyl ether to obtain Compound 29 (80 mg, 0.20 mmol, 74%) as a white solid.

$^1$H NMR (600 MHz, DMSO-d$_6$) δ 8.27 (t, 1H, J=4.8 Hz), 7.98 (s, 1H), 7.62 (dd, 1H, J$_1$=13.8 Hz, J$_2$=2.4 Hz), 7.59-7.46 (m, 1H), 7.42 (t, 1H, J=9.0 Hz), 7.34 (d, 1H, J=9.0 Hz), 7.16 (s, 1H), 7.51-6.89 (bs, 2H), 4.79-4.69 (m, 1H), 4.37 (t, 2H, J=4.2 Hz), 4.13 (t, 1H, J=9.6 Hz), 3.79-3.70 (m, 3H), 3.42 (t, 2H, J=4.8 Hz), 3.38-3.29 (m, 1H), 1.83 (s, 3H).

LCMS: 395 (M+H$^+$) for C$_{16}$H$_{19}$FN$_6$O$_3$S.

EXAMPLE 30

Preparation of Compound 30

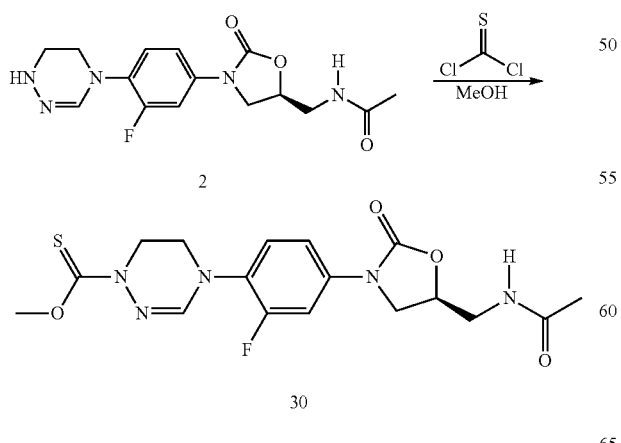

Compound 2 (100 mg, 0.27 mmol) was dissolved in chloroform (3 mL), stirred for 30 minutes after adding saturated aqueous NaHCO$_3$ solution (3 mL) and then adding thiophosgene (0.021 mL) at 0° C. The organic layer was separated, distilled under reduced pressure, and stirred overnight at room temperature after adding methanol (5 mL). The solution was distilled under reduced pressure and separated by column chromatography to obtain Compound 30 (31 mg, 0.20 mmol, 74%) as a white solid.

$^1$H NMR (600 MHz, DMSO-d$_6$) δ 7.60 (dd, 1H, J$_1$=13.2 Hz, J$_2$=1.2 Hz), 7.25-7.18 (m, 1H), 7.16 (t, 1H, J=8.4 Hz), 6.96 (s, 1H), 6.51 (bs, 1H), 4.86-4.79 (m, 1H), 4.64-4.54 (m, 2H), 4.19 (s, 3H), 4.06 (t, 1H, J=9.0 Hz), 3.88-3.76 (m, 3H), 3.74-3.66 (m, 2H), 2.03 (s, 3H).

LCMS: 410 (M+H$^+$) for C$_{17}$H$_{20}$FN$_5$O$_4$S.

EXAMPLE 31

Preparation of Compound 31

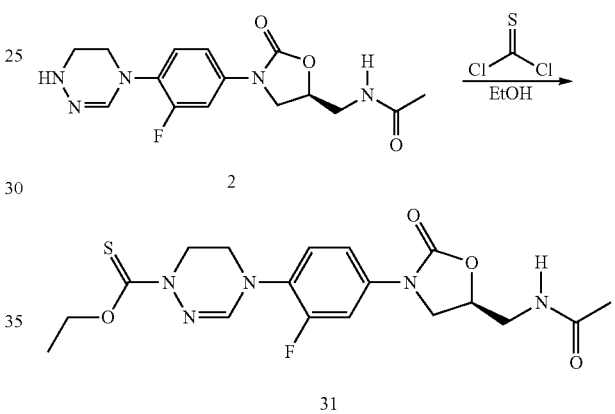

Compound 31 (26 mg, 0.061 mmol, 32%) was obtained from Compound 2 as in Example 30, using ethanol instead of methanol.

$^1$H NMR (600 MHz, DMSO-d$_6$) δ 7.60 (d, J=12.0 Hz), 7.24-7.18 (m, 1H), 7.15 (t, 1H, J=8.4 Hz), 6.97 (s, 1H), 6.32 (bs, 1H), 4.88-4.76 (m, 1H), 4.75-4.64 (m, 2H), 4.64-4.53 (m, 2H), 4.06 (t, 1H, J=8.4 Hz), 3.88-3.77 (m, 3H), 3.74-3.60 (m, 2H), 2.03 (s, 3H), 1.46 (t, 3H, J=6.6 Hz).

LCMS: 424 (M+H$^+$) for C$_{18}$H$_{22}$FN$_5$O$_4$S.

EXAMPLE 32

Preparation of Compound 32

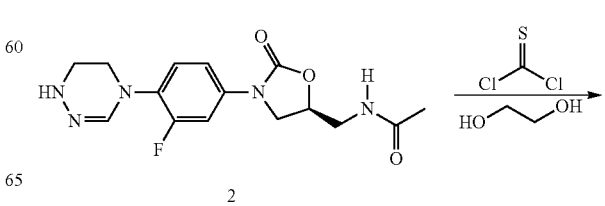

-continued

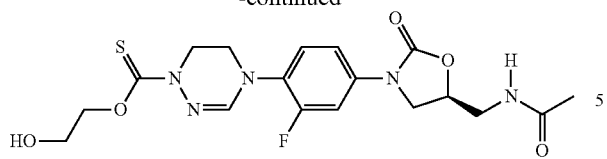

Compound 32 (23 mg, 0.052 mmol, 22%) was obtained from Compound 2 as in Example 30, using ethylene glycol instead of methanol.

$^1$H NMR (600 MHz, chloroform-$d_1$) δ 7.62 (dd, 1H, $J_1$=12.6 Hz, $J_2$=1.8 Hz), 7.23-7.19 (m, 1H), 7.18 (t, 1H, 9.0 Hz), 7.06 (s, 1H), 6.42 (t, 1H, J=6.6 Hz), 4.96-4.86 (bs, 1H), 4.86-4.77 (m, 1H), 4.65 (t, 2H, J=3.6 Hz), 4.59 (t, 2H, J=4.8 Hz), 4.07 (t, 1H, 9.0 Hz), 3.98-3.89 (m, 2H), 3.88-3.79 (m, 3H), 3.72-3.65 (m, 2H), 2.03 (s, 3H).

LCMS: 440 (M+H$^+$) for $C_{18}H_{22}FN_5O_5S$.

EXAMPLE 33

Preparation of Compound 33

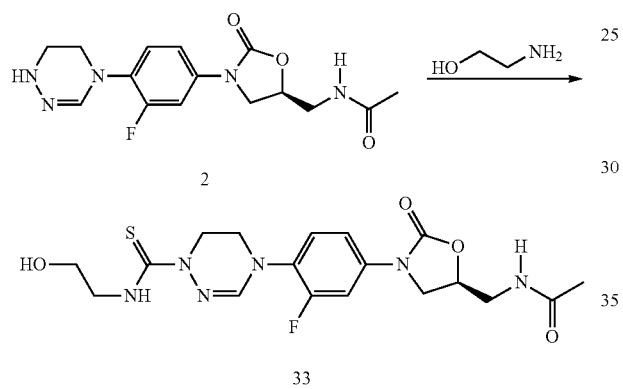

Compound 33 (16 mg, 0.036 mmol, 35%) was obtained from Compound 2 as in Example 30, using aminoethanol instead of methanol.

$^1$H NMR (600 MHz, DMSO-$d_6$) δ 8.28 (t, 1H, J=5.4 Hz), 7.67-7.58 (m, 1H), 7.43 (t, 1H, J=9.0 Hz), 7.38-7.31 (m, 1H), 7.20 (s, 1H), 4.08 (t, 1H, J=5.4 Hz), 4.78-4.70 (m, 1H), 4.39 (t, 2H, J=4.8 Hz), 4.13 (t, 1H, J=9.0 Hz), 3.81-3.75 (m, 2H), 3.58 (t, 2H, J=4.2 Hz), 3.53 (t, 2H, J=5.7 Hz), 3.42 (t, 2H, J=5.4 Hz), 1.83 (s, 3H).

LCMS: 439 (M+H$^+$) for $C_{18}H_{23}FN_6O_4S$.

EXAMPLE 34

Preparation of Compound 34

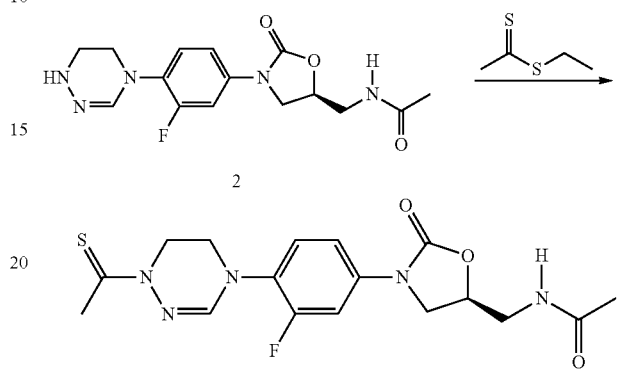

Compound 2 (50 mg, 0.13 mmol) was dissolved in ethanol (5 mL) and stirred overnight at room temperature after adding DIPEA (0.03 mL, 0.2 mmol), NaF (7 mg, 0.17 mmol) and ethyl dithioacetate (0.019 mL, 0.16 mmol). The solution was distilled under reduced pressure and separated by column chromatography to obtain Compound 34 (10 mg, 0.025 mmol, 19%) as a white solid.

$^1$H NMR (600 MHz, CDCl$_3$) δ=7.62 (dd, $J_1$=13.8 Hz, $J_2$=2.4 Hz, 1H), 7.25-7.21 (m, 2H), 7.16 (t, J=8.4 Hz, 1H), 6.94 (s, 1H), 5.93 (br, t, 1H), 4.81 (m, 1H), 4.73 (t, J=5.2 Hz, 2H), 4.06 (t, J=8.8 Hz, 1H), 3.83-3.62 (m, 5H), 2.81 (s, 3H), 2.03 (s, 3H).

LCMS: 394 (M+H$^+$) for $C_{17}H_{20}FN_5O_3S$.

EXAMPLE 35

Preparation of Compound 35

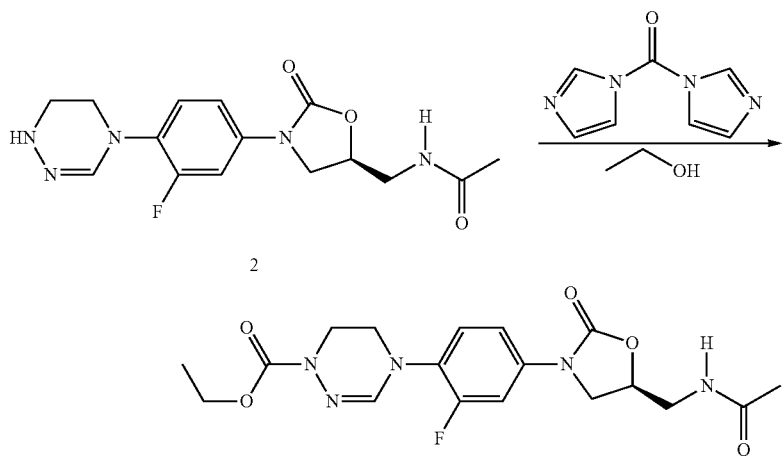

Compound 35 (35 mg, 0.086 mmol, 65%) was obtained from Compound 2 as in Example 6, using carbonyldiimidazole and ethanol.

$^1$H NMR (600 MHz, CDCl$_3$) δ=7.58-7.56 (m, 1H), 7.19-7.18 (m, 1H), 7.13-7.10 (m, 1H), 6.92 (s, 1H), 6.21 (m, 1H), 4.80 (m, 1H), 4.33-4.32 (m, 2H), 4.06-4.03 (m, 1H), 3.99 (m, 2H), 3.81-3.77 (m, 3H), 3.71-3.66 (m, 2H), 2.03 (s, 3H), 1.38 (t, J=6.3 Hz, 3H).

LCMS: 407 (M+H$^+$) for C$_{18}$H$_{22}$FN$_5$O$_5$.

EXAMPLE 36

Preparation of Compound 36

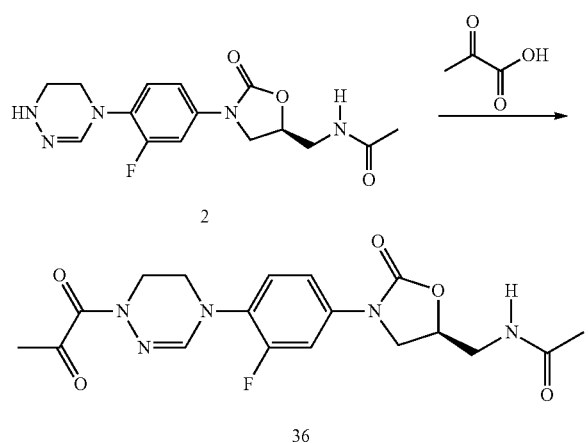

Compound 36 (14 mg, 0.034 mmol, 74%) was obtained from Compound 2 as in Example 11, using pyruvic acid.

$^1$H NMR (600 MHz, DMSO-d$_6$) δ 8.27 (t, J=6.0 Hz, 1H) 7.61 (dd, J$_1$=13.2 Hz, J$_2$=3.0 Hz, 1H), 7.40 (t, J=9.0 Hz, 1H), 7.33 (dd, J$_1$=9.0 Hz, J$_2$=2.4 Hz, 1H), 7.18 (s, 1H), 4.74 (m, 1H), 4.13 (t, J=9 Hz, 1H), 3.90 (t, J=4.8 Hz, 2H), 3.77-3.72 (m, 3H), 3.42-3.30 (m, 2H), 2.33 (s, 3H), 1.83 (s, 3H).

LCMS: 406 (M+H$^+$) for C$_{18}$H$_{20}$FN$_5$O$_5$.

EXAMPLE 37

Preparation of Compound 37

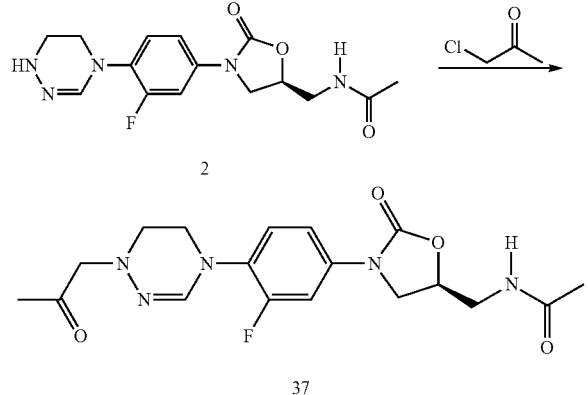

Compound 37 (13 mg, 0.033 mmol, 65%) was obtained from Compound 2 as in Example 4, using chloroacetone.

$^1$H NMR (600 MHz, CDCl$_3$) δ=7.52 (dd, J$_1$=13.8 Hz, J$_2$=2.4 Hz, 1H), 7.15 (dd, J$_1$=8.4 Hz, J$_2$=2.4 Hz, 1H), 7.11 (t, J=8.4 Hz, 1H), 6.89 (s, 1H), 6.09 (br, t, 1H), 4.79 (m, 1H), 4.04 (t, J=9 Hz, 1H), 3.85 (t, J=4.8 Hz, 2H), 3.79-3.62 (m, 5H), 3.12 (t, J=4.8 Hz, 2H), 2.26 (s, 3H), 2.03 (s, 3H).

LCMS: 392 (M+H$^+$) for C$_{18}$H$_{22}$FN$_5$O$_4$.

EXAMPLE 38

Preparation of Compound 38

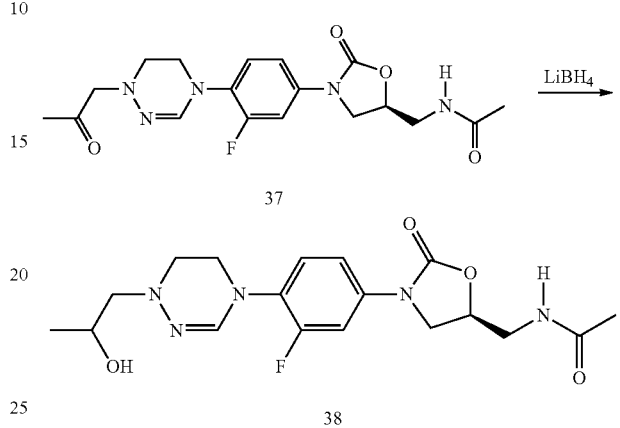

Compound 37 (7 mg, 0.018 mmol) was dissolved in dichloromethane (2 mL) and stirred for 2 hours at room temperature after adding 2M LiBH$_4$ solution. After adding a small amount of water, the solution was separated by column chromatography to obtain Compound 38 (3.6 mg, 0.009 mmol, 50%) as a white solid.

$^1$H NMR (600 MHz, CDCl$_3$) δ=7.54 (dd, J$_1$=13.8 Hz, J$_2$=2.4 Hz, 1H), 7.15 (dd, J$_1$=8.4 Hz, J$_2$=2.4 Hz, 1H), 7.11 (t, J=8.4 Hz, 1H), 6.89 (s, 1H), 6.09 (br, t, 1H), 4.79 (m, 1H), 4.04 (t, J=9 Hz, 1H), 3.85 (t, J=4.8 Hz, 2H), 3.79-3.62 (m, 5H), 3.12 (t, J=4.8 Hz, 2H), 2.26 (s, 3H), 2.03 (s, 3H).

LCMS: 394 (M+H$^+$) for C$_{18}$H$_{24}$FN$_5$O$_4$.

EXAMPLE 39

Preparation of Compound 39

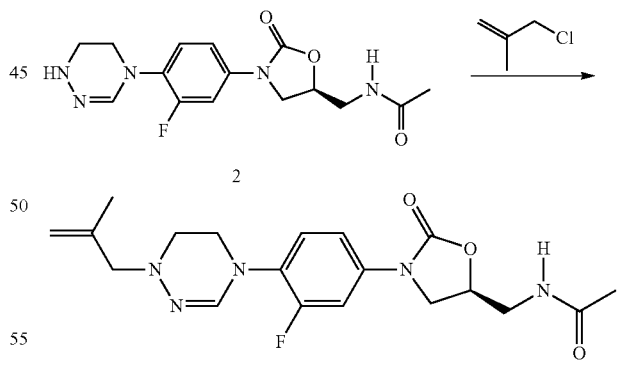

Compound 39 (15 mg, 0.039 mmol, 74%) was obtained from Compound 2 as in Example 4, using 3-chloro-2-methylpropene.

$^1$H NMR (600 MHz, CDCl$_3$) δ=7.51 (dd, J$_1$=13 Hz, J$_2$=2.4 Hz, 1H), 7.15-7.09 (m, 2H), 6.91 (s, 1H), 6.06 (br, t, 1H), 4.97 (s, 1H), 4.93 (s, 1H), 4.79 (m, 1H), 4.04 (t, J=9 Hz, 1H), 3.81 (t, J=4.8 Hz, 2H), 3.78-3.61 (m, 3H), 3.48 (s, 2H), 2.94 (t, J=4.8 Hz, 2H), 2.03 (s, 3H), 1.83 (s, 3H).

LCMS: 390 (M+H$^+$) for C$_{19}$H$_{24}$FN$_5$O$_3$.

EXAMPLE 40

Preparation of Compound 40

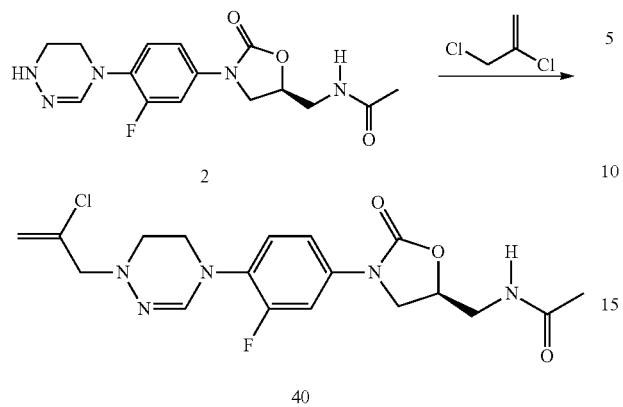

Compound 40 (11 mg, 0.027 mmol, 34%) was obtained from Compound 2 as in Example 4, using 2,3-dichloro-1-propene.

$^1$H NMR (600 MHz, CDCl$_3$) δ=7.52 (dd, J$_1$=13 Hz, J$_2$=2.4 Hz, 1H), 7.15-7.09 (m, 2H), 6.91 (s, 1H), 6.23 (br, t, 1H), 5.49 (s, 1H), 5.42 (s, 1H), 4.79 (m, 1H), 4.04 (t, J=9 Hz, 1H), 3.85 (t, J=4.8 Hz, 2H), 3.79-3.62 (m, 5H), 3.08 (t, J=4.8 Hz, 2H), 2.03 (s, 3H).

LCMS: 410 (M+H$^+$) for C$_{18}$H$_{21}$ClFN$_5$O$_3$.

EXAMPLE 41

Preparation of Compound 41

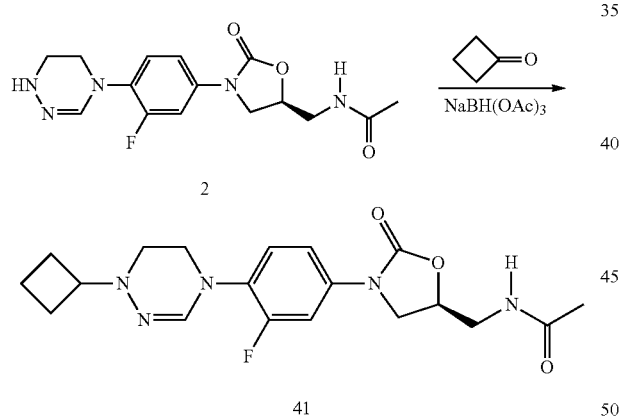

Compound 2 (228 mg, 0.68 mmol), cyclobutanone (0.076 mL, 1.02 mmol) and NaBH(OAc)$_3$ (187 mg, 0.88 mmol) were dissolved in dichloromethane (20 mL) and stirred for 2 hours at room temperature after adding acetic acid (1 mL). The solution was diluted with dichloromethane, sequentially washed with saturated aqueous sodium bicarbonate solution and saturated aqueous sodium chloride solution (brine), dried with anhydrous sodium sulfate, and concentrated under reduced pressure to obtain Compound 41 (200 mg, 0.51 mmol, 75%) as a white solid.

$^1$H NMR (600 MHz, CDCl$_3$) δ=7.51 (dd, J$_1$=13 Hz, J$_2$=2.4 Hz, 1H), 7.15-7.09 (m, 2H), 6.95 (s, 1H), 6.09 (br, t, 1H), 4.79 (m, 1H), 4.03 (t, J=9 Hz, 1H), 3.82 (t, J=4.8 Hz, 2H), 3.78-3.61 (m, 3H), 3.41 (m, 1H), 2.91 (t, J=4.8 Hz, 2H), 2.21-2.11 (m, 4H), 2.03 (s, 3H), 1.81-1.72 (m, 2H).

LCMS: 390 (M+H$^+$) for C$_{19}$H$_{24}$FN$_5$O$_3$.

EXAMPLE 42

Preparation of Compound 42

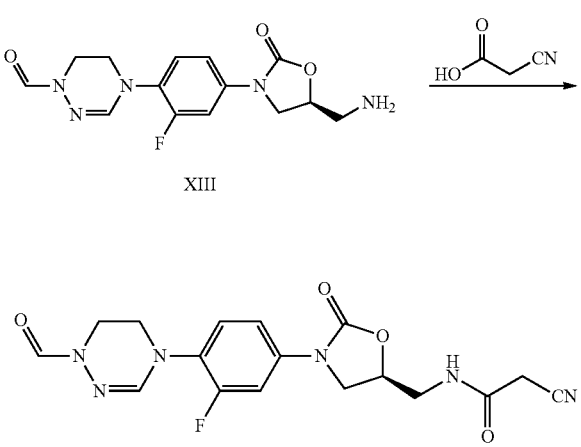

Compound 42 (15 mg, 0.039 mmol, 79%) was obtained from Compound XIII as in Example 11.

$^1$H NMR (400 MHz, DMSO-d$_6$) δ=8.64 (t, J=5.6 Hz, 1H), 8.42 (s, 1H), 7.61 (dd, J$_1$=14 Hz, J$_2$=2.0 Hz, 1H), 7.38 (t, J=8.8 Hz, 1H), 7.33 (dd, J$_1$=8.8 Hz, J$_2$=2.0 Hz, 1H), 7.12 (s, 1H), 4.78 (m, 1H), 4.14 (t, J=9.2 Hz, 1H), 3.84 (t, J=4.8 Hz, 2Hz, 3.75-3.47 (m, 7H).

LCMS: 389 (M+H$^+$) for C$_{17}$H$_{17}$FN$_6$O$_4$.

EXAMPLE 43

Preparation of Compound 43

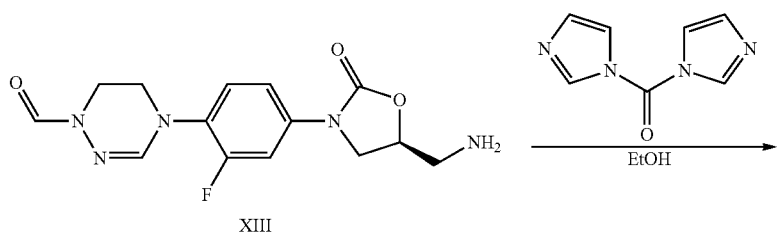

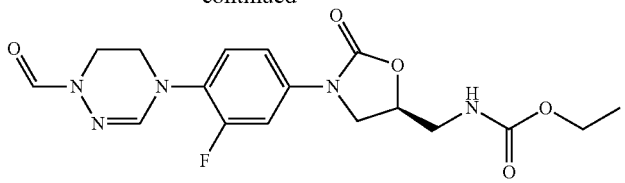

43

Compound XIII (190 mg, 0.6 mmol) and carbonyldiimidazole (143 mg, 0.9 mmol) were dissolved in dichloromethane (5 mL) and stirred for 6 hours at room temperature after adding triethylamine (0.25 mL, 1.8 mmol). After ⅓ of the solution was distilled off under reduced pressure, dissolved in dichloromethane (5 mL) and ethanol (10 mL), and stirred for 36 hours at room temperature. The solution was washed with distilled water, dried with magnesium sulfate, concentrated under reduced pressure, and separated by column chromatography to obtain Compound 43 (23 mg, 0.058 mmol, 29%).

$^1$H NMR (600 MHz, DMSO-$d_6$) δ=8.38 (s, 1H), 7.56 (dd, $J_1$=14 Hz, $J_2$=2.0 Hz, 1H), 7.45 (br, t, 1H), 7.35-7.28 (m, 2H), 7.01 (s, 1H), 4.69 (m, 1H), 4.10 (t, J=9.2 Hz, 1H), 3.95 (q, J=6.6 Hz, 2H), 3.80-3.3 (m, 7H), 1.09 (t, J=6.6 Hz, 3H).

LCMS: 394 (M+H$^+$) for $C_{17}H_{20}FN_5O_5$.

EXAMPLE 44

Preparation of Compound 44

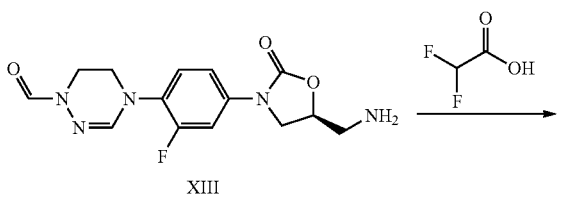

Compound XIII (190 mg, 0.6 mmol) and carbonyldiimidazole (143 mg, 0.9 mmol) were dissolved in dichloromethane (5 mL) and stirred for 6 hours at room temperature after adding triethylamine (0.25 mL, 1.8 mmol). After ⅓ of the solution was distilled off under reduced pressure, dissolved in THF (5 mL) and ethylamine (50 mg), stirred for 36 hours at room temperature, and refluxed for 2 hours. The solution was washed with distilled water, dried with magnesium sulfate, concentrated under reduced pressure, and separated by column chromatography to obtain Compound 44 (35 mg, 0.089 mmol, 45%).

$^1$H NMR (600 MHz, CDCl$_3$) δ=8.53 (s, 1H), 7.59 (d, J=13 Hz, 1H), 7.19 (d, J=9 Hz, 1H), 7.13 (d, J=9 Hz, 1H), 6.88 (s, 1H), 5.75 (br, s, 1H), 5.28 (br, s, 1H), 4.81 (m, 1H), 4.04 (t, J=8.2 Hz, 1H), 3.98-3.15 (m, 9H), 1.08 (t, J=6.6 Hz, 3H).

LCMS: 393 (M+H$^+$) for $C_{17}H_{21}FN_6O_4$.

EXAMPLE 45

Preparation of Compound 45

Compound 45 (840 mg, 2.1 mmol, 95%) was obtained from Compound XIII as in Example 11, using difluoroacetic acid.

¹H NMR (400 MHz, DMSO-d₆) δ=9.18 (t, J=5.6 Hz, 1H), 8.42 (s, 1H), 7.61 (dd, J₁=14 Hz, J₂=2.0 Hz, 1H), 7.38 (t, J=8.8 Hz, 1H), 7.32 (dd, J₁=8.8 Hz, J₂2.0 Hz, 1H), 7.12 (s, 1H), 6.26 (t, J=53 Hz, 1H) 4.82 (m, 1H), 4.16 (t, J=8.8 Hz, 1H), 3.84 (t, J=4.8 Hz, 2H), 3.80-3.53 (m, 5H).

LCMS: 400 (M+H⁺) for $C_{16}H_{16}F_3N_5O_4$.

EXAMPLE 46

Preparation of Compound 46

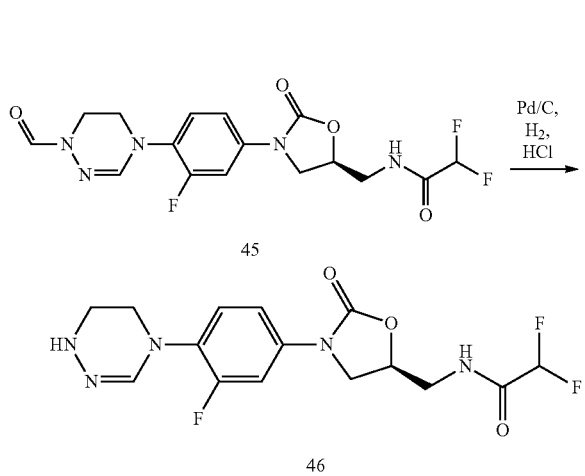

Compound 46 (750 mg, 1.8 mmol, 84%) was obtained from Compound 45 as in Example 2.

¹H NMR (600 MHz, DMSO-d₆) δ9.17-9.30 (m, 1H), 8.43-8.28 (m, 1H), 7.67 9dd, 1H, J₁=13.8 Hz, J₂=2.4 Hz), 7.61 (t, 1H, J=9.0 Hz), 7.44-7.36 (m, 1H), 6.27 (9t, 1H, J=53.4 Hz), 4.85-4.80 (m, 1H), 4.19 (t, 1H, J=9.0 Hz), 3.81-3.75 (m, 2H), 3.38-3.32 (m, 2H).

LCMS: 372 (M+H⁺) for $C_{15}H_{16}F_3N_5O_3$.

EXAMPLE 47

Preparation of Compound 47

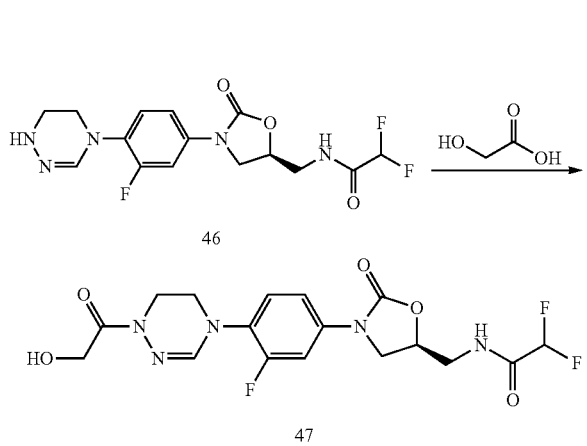

Compound 47 (16 mg, 0.037 mmol, 25%) was obtained from Compound 46 as in Example 12.

¹H NMR (600 MHz, chloroform-d₁) δ 7.57 (dd, 1H, J₁=13.8 Hz, J₂=2.4 Hz), 7.21 (dd, 1H, J₁=9.0 Hz, J₂=2.4 Hz), 7.13 (t, 1H, J=9.0 Hz), 6.96-6.90 (m, 1H), 6.86 (s, 1H), 5.94 (t, 1H, J=54.0 Hz), 4.88-4.83 (m, 1H), 4.12 (t, 1H, J=9.0 Hz), 4.06 (t, 2H, J=5.4 Hz), 3.90-3.81 (m, 1H), 3.80-3.74 (m, 3H), 3.74-3.66 (m, 1H), 3.64 (s, 2H).

LCMS: 430 (M+H⁺) for $C_{17}H_{28}F_3N_5O_5$.

EXAMPLE 48

Preparation of Compound 48

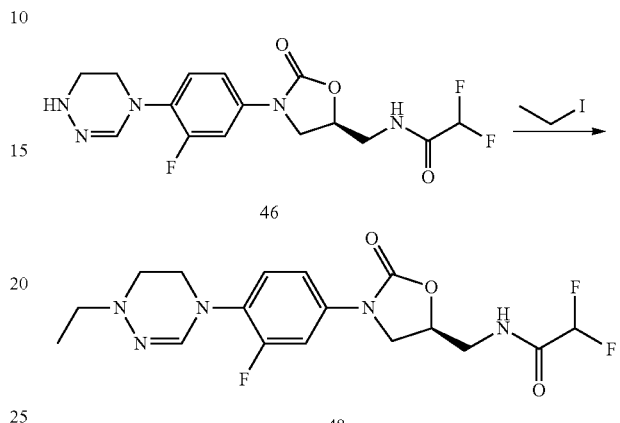

Compound 48 (16 mg, 0.04 mmol, 61%) was obtained from Compound 46 as in Example 6.

¹H NMR (600 MHz, chloroform-d₁) δ 7.48 (dd, 1H, J₁=13.2 Hz, J₂=2.4 Hz), 7.23 (t, 1H, J=5.4 Hz), 7.16-7.08 (m, 2H), 6.94 (s, 1H), 5.94 (t, 1H, J=54.0 Hz), 4.86-4.82 (m, 1H), 4.10 (t, 1H, J=9.0 Hz), 3.88-3.84 (m, 1H), 3.83 (t, 2H, J=4.8 Hz), 3.78-3.73 (m, 1H), 3.73-3.64 (m, 1H), 3.02 (t, 2H, J=4.8 Hz), 3.00-2.94 (m, 3H), 1.23 (t, 2H, 7.2 Hz).

LCMS: 400 (M+H⁺) for $C_{17}H_{20}F_3N_5O_3$.

EXAMPLE 49

Preparation of Compound 49

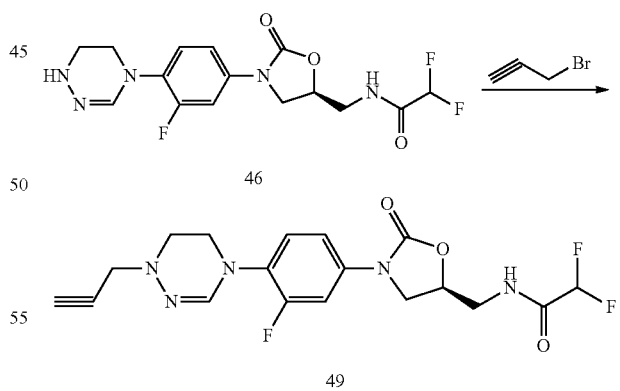

Compound 49 (15 mg, 0.037 mmol, 57%) was obtained from Compound 46 as in Example 5.

¹H NMR (600 MHz, CDCl₃) δ 7.51 (dd, J₁=13.8 Hz, J₂=2.4 Hz, 1H), 7.16-7.11 (m, 2H), 6.96 (s, 1H), 6.89 (br, t, 1H), 5.94 (t, J=54.0 Hz, 1H), 4.84 (m, 1H), 4.11 (t, J=9.0 Hz, 1H), 3.89-3.64 (m, 7H), 3.13 (t, J=4.8 Hz, 2H), 2.31 (t, J=2.4 Hz).

LCMS: 410 (M+H⁺) for $C_{18}H_{18}F_3N_5O_3$.

EXAMPLE 50

Preparation of Compound 50

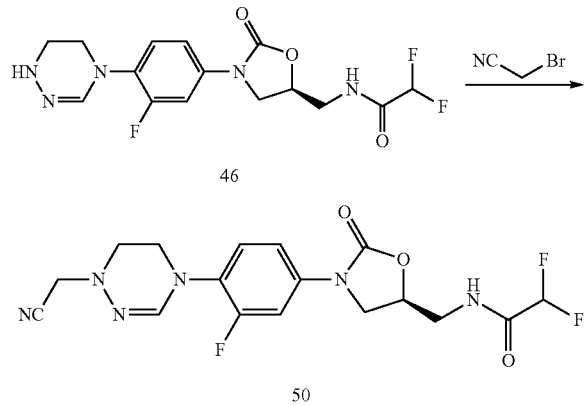

Compound 50 (15 mg, 0.037 mmol, 68%) was obtained from Compound 46 as in Example 7.

$^1$H NMR (600 MHz, CDCl$_3$) δ 7.53 (dd, J$_1$=13.8 Hz, J$_2$=2.4 Hz, 1H), 7.17-7.13 (m, 2H), 7.01 (br, t, 1H), 6.96 (s, 1H), 5.94 (t, J=54.0 Hz, 1H), 4.85 (m, 1H), 4.11 (t, J=9.0 Hz, 1H), 3.98 (s, 2H) 3.89-3.66 (m, 5H), 3.15 (t, J=4.8 Hz, 2H).

LCMS: 411 (M+H$^+$) for C$_{17}$H$_{17}$F—$_3$—N$_6$O$_3$.

EXAMPLE 51

Preparation of Compound 51

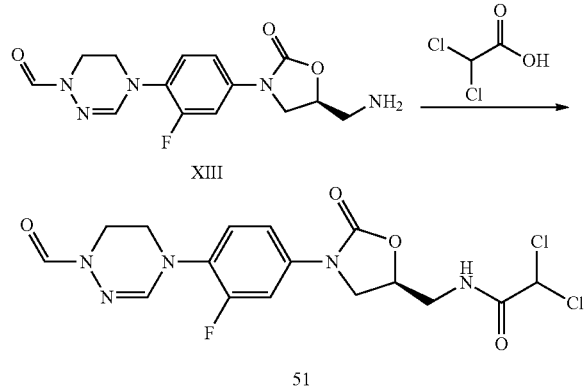

Compound 51 (155 mg, 0.36 mmol, 86%) was obtained from Compound XIII as in Example 11, using dichloroacetic acid.

$^1$H NMR (400 MHz, DMSO-d$_6$) δ=8.99 (t, J=6.0 Hz, 1H), 8.42 (s, 1H), 7.61 (d, J=12 Hz, 1H), 7.38 (t, J=9.0 Hz, 1H), 7.31 (d, J=9Hz, 1H), 7.12 (s, 1H), 6.49 (s, 1H), 4.81 (m, 1H), 4.16 (t, J=8.8 Hz, 1H), 3.84 (t, J=4.8 Hz, 2H), 3.74-3.66 (m, 3H), 3.55 (t, J=5.2 Hz, 2H).

LCMS: 432 (M+H$^+$) for C$_{16}$H$_{16}$Cl—$_2$—FN$_5$O$_4$.

EXAMPLE 52

Preparation of Compound 52

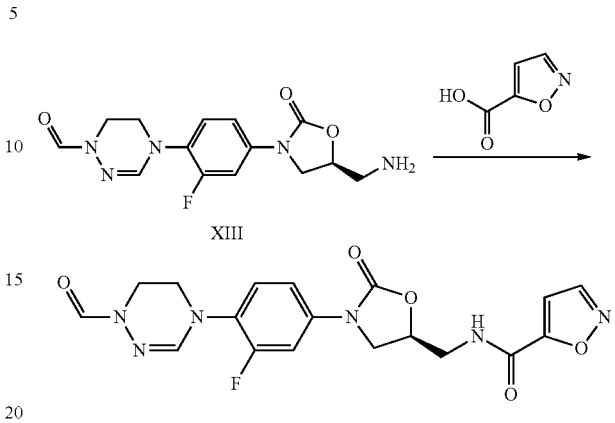

Compound 52 (250 mg, 0.6 mmol, 92%) was obtained from Compound XIII as in Example 11, using isoxazole acid.

$^1$H NMR (400 MHz, DMSO-d$_6$) δ=9.32 (t, J=5.6 Hz, 1H), 8.75 (d, J=1.2 Hz, 1H) 8.42 (s, 1H), 7.60 (dd, J$_1$=14 Hz, J$_2$=2.0 Hz, 1H), 7.38 (t, J=8.8 Hz), 7.33 (dd, J$_1$=8.8 Hz, J$_2$=2.0 Hz, 1H), 7.11 (d, J=1.2 Hz, 1H), 4.88 (m, 1H), 4.18 (t, J=9.2 Hz, 1H), 3.88-3.82 (m, 3H), 3.69 (t, J=5.2 Hz, 2H), 3.64 (t, J=5.6 Hz, 2H).

LCMS: 417 (M+H$^+$) for C$_{18}$H$_{17}$—FN$_6$O$_5$.

EXAMPLE 53

Preparation of Compound 53

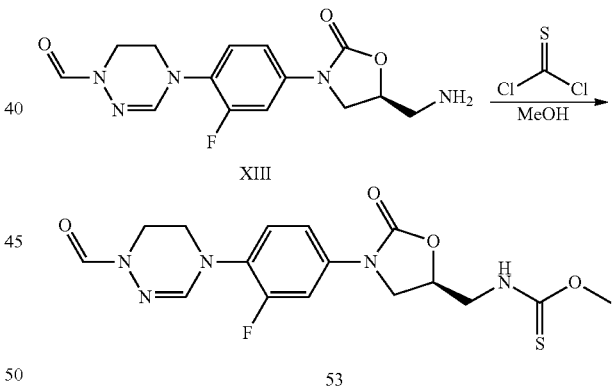

Compound XIII (4.5 g, 14 mmol) was dissolved in dichloromethane (75 mL) and stirred for 1 hour after adding saturated aqueous NaHCO$_3$ solution (75 mL) and thio-phosgene (1.1 mL, 14 mmol) at 0° C. The organic layer was dried with sodium sulfate, distilled under reduced pressure, dissolved in methanol (120 mL), stirred overnight under reflux, concentrated under reduced pressure, and separated by column chromatography to obtain Compound 53 (3.18 g, 8.05 mmol, 58%) as a white solid.

$^1$H NMR (600 MHz, CDCl$_3$) δ=8.55 (s, 1H), 7.58 (dd, J$_1$=13 Hz, J$_2$=2.4 Hz, 1H), 7.21 (dd, J$_1$=9.0 Hz, J$_2$=2.7 Hz, 1H), 7.13 (t, J=8.4 Hz, 1H), 6.89 (s, 1H), 6.71 (t, J=6.3 Hz, 1H), 4.93 (m, 1H), 4.13-4.08 (m, 2H), 4.05 (m, 1H), 4.01 (s, 3H), 3.99 (t, J=5.0 Hz, 2H), 3.90 (m, 1H), 3.74 (t, J=5.0 Hz, 2H).

LCMS: 396 (M+H$^+$) for C$_{16}$H$_{18}$FN$_5$O$_4$S.

EXAMPLE 54

Preparation of Compound 54

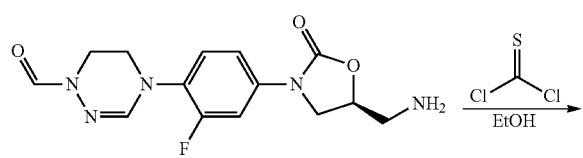

Compound 54 (210 mg, 0.51 mmol, 65%) was obtained from Compound XIII as in Example 53, using ethanol instead of methanol.

$^1$H NMR (600 MHz, CDCl$_3$) δ=8.54 (s, 1H), 7.58 (dd, J$_1$=14 Hz, J$_2$=2.8 Hz, 1H), 7.21 (dd, J$_1$=14 Hz, J$_2$=3.8 Hz, 1H), 7.13 (t, J=8.4 Hz, 1H), 6.88 (s, 1H), 6.75 (t, J=6.3 Hz, 1H), 4.96 (m, 1H), 4.54-4.44 (m, 2H), 4.09-4.02 (m, 3H), 3.98 (t, J=4.8 Hz, 2H), 3.92 (m, 1H), 3.73 (t, J=4.8 Hz, 2H), 1.31 (t, J=7 Hz, 3H).

LCMS: 410 (M+H$^+$) for C$_{17}$H$_{20}$FN$_5$O$_4$S.

EXAMPLE 55

Preparation of Compound 55

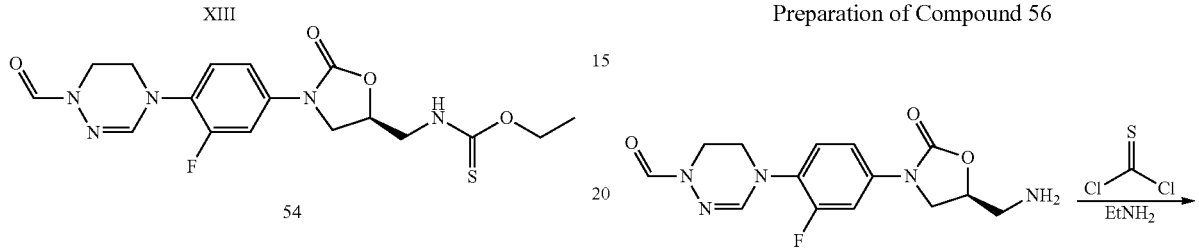

Compound 55 (52 mg, 0.12 mmol, 52%) was obtained from Compound XIII as in Example 53, using isopropanol instead of methanol.

$^1$H NMR (600 MHz, CDCl$_3$) δ=8.55 (s, 1H), 7.58 (dd, J$_1$=13 Hz, J$_2$=2.4 Hz, 1H), 7.22 (dd, J$_1$=9.0 Hz, J$_2$=2.7 Hz, 1H), 7.13 (t, J=8.4 Hz, 1H), 6.88 (s, 1H), 6.57 (t, J=6.3 Hz, 1H), 5.54 (m, 1H), 4.93 (m, 1H), 4.12-4.06 (m, 2H), 4.02 (m, 1H), 3.99 (t, J=4.8 Hz, 2H), 3.92 (m, 1H), 3.73 (t, J=4.8 Hz, 2H), 1.32 (d, J=6 Hz, 3H), 1.27 (d, J=6 Hz, 3H).

LCMS: 424 (M+H$^+$) for C$_{18}$H$_{22}$FN$_5$O$_4$S.

EXAMPLE 56

Preparation of Compound 56

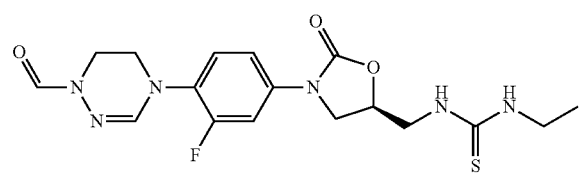

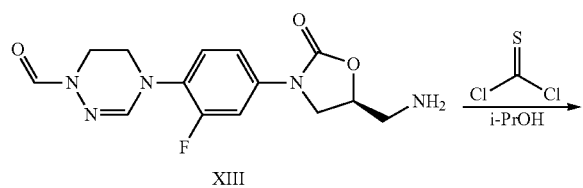

Compound 56 (36 mg, 0.088 mmol, 57%) was obtained from Compound XIII as in Example 53, using ethylamine instead of methanol.

$^1$H NMR (600 MHz, CDCl$_3$) δ=8.54 (s, 1H), 7.58 (dd, 1H, J$_1$=13.2 Hz, J$_2$=2.4 Hz), 7.20-7.19 (m, 1H), 7.13 (t, 1H, J=9.0 Hz), 6.88 (s, 1H), 4.92-4.96 (m, 1H), 4.10-4.06 (m, 3H), 3.99 (t, 2H, J=4.8 Hz), 1.44-1.43 (m,2H), 1.21 (t, 3H, J=7.2 Hz).

LCMS: 409 (M+H$^+$) for C$_{17}$H$_{21}$FN$_6$O$_3$S.

EXAMPLE 57

Preparation of Compound 57

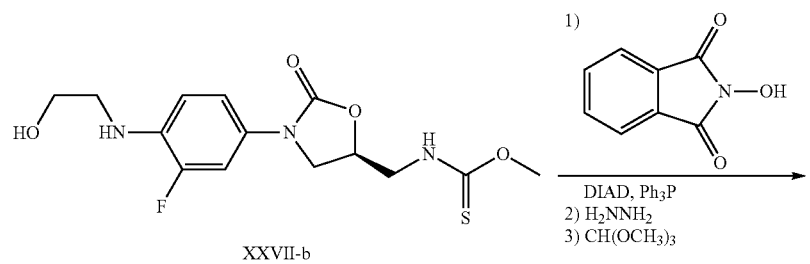

-continued

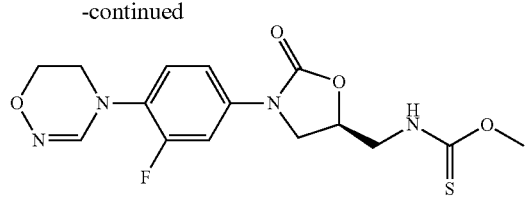

57

Compound XXVII-b prepared in Preparation Example 14 was subjected to Mitsunobu reaction as in Example 16. Then, Compound 57 (84 mg, 0.23 mmol, 31%) was obtained as in Example 28.

$^1$H NMR (600 MHz, CDCl$_3$) δ=8.25 (s, 1H), 7.62 (dd, J$_1$=13 Hz, J$_2$=2.0 Hz, 1H), 7.30 (t, J=9 Hz, 1H), 7.24 (dd, J$_1$=9 Hz, J$_2$=2.0 Hz, 1H), 6.73 (br, t, 1H), 4.94 (m, 1H), 4.21-4.04 (m, 4H), 4.01 (s, 3H), 3.90 (t, J=4.8 Hz, 2H), 3.80 (t, J=4.8 Hz, 2H).

LCMS: 369 (M+H$^+$) for C$_{15}$H$_{17}$FN$_4$O$_4$S.

EXAMPLE 58

Preparation of Compound 58

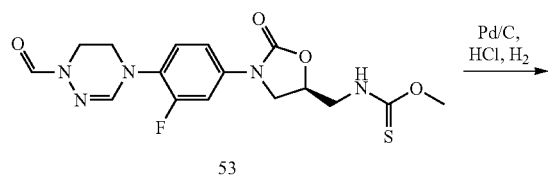

53

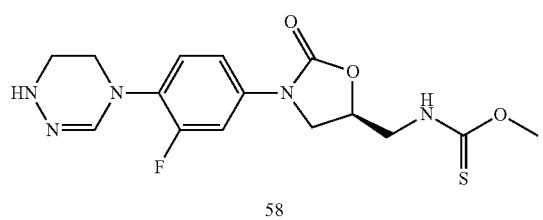

58

Compound 53 (400 mg, 1.01 mmol) was dissolved in methanol (20 mL), stirred for 2 hours under hydrogen balloon after adding 4N HCl dioxane solution (2 mL) and 10% Pd/C (50 mg), filtered with celite, and distilled under reduced pressure to quantitatively obtain Compound 58 as a white solid.

$^1$H NMR (600 MHz, CDCl$_3$) δ=7.51 (dd, J$_1$=14 Hz, J$_2$=1.8 Hz, 1H), 7.16-7.10 (m, 2H), 6.89 (s, 1H), 6.78 (br, t, 1H), 4.93 (m, 1H), 4.10-3.98 (m, 6H), 3.88-3.81 (m, 3H), 3.32 (t, J=4.8 Hz, 2H).

LCMS: 368 (M+H$^+$) for C$_{15}$H$_{18}$FN$_5$O$_3$S.

EXAMPLE 59

Preparation of Compound 59

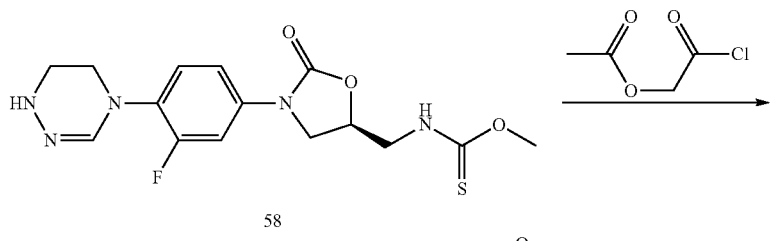

58

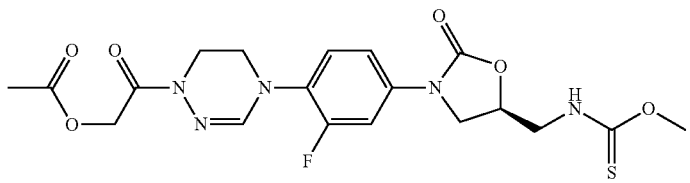

59

Compound 58 (150 mg, 0.41 mmol) was dissolved in dichloromethane (5 mL), stirred at room temperature for 6 hours after adding DIPEA (0.14 mL, 0.82 mmol) and acetoxyacetyl chloride (0.066 mL, 0.61 mmol) at 0° C. The solution was distilled under reduced pressure and separated by column chromatography to obtain Compound 59 (31 mg, 0.066 mmol, 16%) as white solid.

$^1$H NMR (600 MHz, CDCl$_3$) δ 7.58 (dd, J$_1$=13.8 Hz, J$_2$=2.4 Hz, 1H), 7.22-7.11 (m, 2H), 6.83 (s, 1H), 6.69 (t, J=6.0 Hz, 1H), 5.08 (s, 2H), 4.96 (m, 1H), 4.10-3.89 (m, 9H), 3.74 (t, J=4.8 Hz, 2H), 2.20 (s, 3H).

LCMS: 468 (M+H$^+$) for C$_{19}$H$_{22}$FN$_5$O$_6$S.

EXAMPLE 60

Preparation of Compound 60

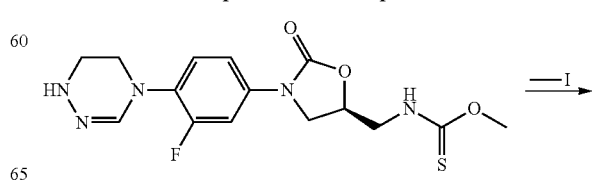

58

87

-continued

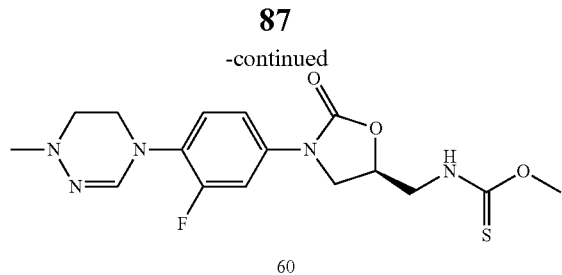
60

Compound 58 (0.013 mg, 0.035 mmol) was dissolved in DMF (2 mL), stirred overnight at room temperature after adding DIPEA (0.01 mL, 0.07 mmol) and iodomethane (0.003 mL, 0.035 mmol), and separated by column chromatography to obtain Compound 60 (3.1 mg, 0.0081 mmol, 23%) as a white solid.

$^1$H NMR (600 MHz, CDCl$_3$) δ=7.52 (dd, J$_1$=14 Hz, J$_2$=2.0 Hz, 1H), 7.15 (dd, J=9 Hz, J$_2$=2.0 Hz, 1H), 7.11 (t, J=9 Hz, 1H), 6.90 (s, 1H), 6.76 (br, t, 1H), 4.94 (m, 1H), 4.10-3.85 (m, 7H), 3.82 (t, J$_1$=4.8 Hz, 2H), 2.99 (t, J$_1$=4.8 Hz, 2H), 2.79 (s, 3H).

LCMS: 382 (M+H$^+$) for C$_{16}$H$_{20}$FN$_5$O$_3$S.

EXAMPLE 61

Preparation of Compound 61

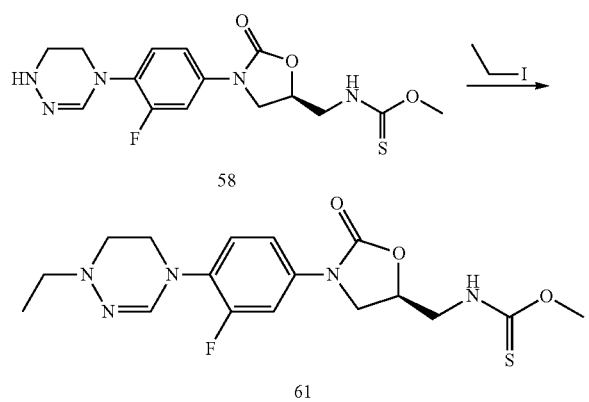

Compound 61 (15 mg, 0.038 mmol, 45%) was obtained from Compound 58 as in Example 60, using iodoethane instead of iodomethane.

$^1$H NMR (600 MHz, CDCl$_3$) δ=7.51 (dd, J$_1$=14 Hz, J$_2$=1.8 Hz, 1H), 7.15 (dd, J$_1$=8.4 Hz, J$_2$=2.4 Hz, 1H), 7.11 (m, 1H), 6.92 (s, 1H), 6.77 (br, t, 1H), 4.93 (m, 1H), 4.11-4.02 (m, 3H), 4.01 (s, 3H), 3.88-3.85 (m, 1H), 3.83 (t, J=4.8 Hz, 2H), 3.02 (t, J=4.8 Hz, 2H), 2.98-2.94 (m, 2H), 1.24 (t, J=7.2 Hz, 3H).

LCMS: 396 (M+H$^+$) for C$_{17}$H$_{22}$FN$_5$O$_3$S.

EXAMPLE 62

Preparation of Compound 62

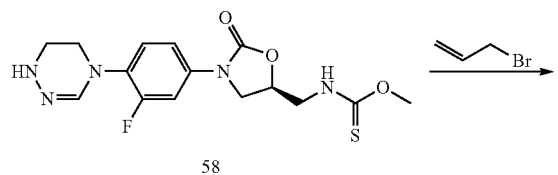
58

88

-continued

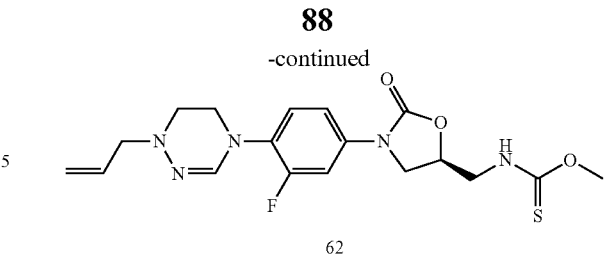
62

Compound 62 (15 mg, 0.037 mmol, 67%) was obtained from Compound 58 as in Example 60, using allyl bromide instead of iodomethane.

$^1$H NMR (600 MHz, chloroform-d$_1$) δ 7.51 (dd, 1H, J$_1$=13.2 Hz, J$_2$=1.8 Hz), 7.15 (dd, 1H, J$_1$=9.0 Hz, J$_2$=2.4 Hz), 7.11 (t, 1H, 8.4 Hz), 6.92 (s, 1H), 6.68 (t, 1H, J=6.0 Hz), 6.08-5.96 (m, 1H), 5.29 (dd, 1H, J$_1$=10.2 Hz, J$_2$=1.8 Hz), 5.24 (dd, 1H, J$_1$=10.2 Hz, J$_2$=1.8 Hz), 4.98-4.88 (m, 1H), 4.12-4.04 (m, 2H), 4.02-3.98 (m, 1H), 4.01 (s, 3H), 3.86 (dd, 1H, J$_1$=9.6 Hz, J$_2$=7.2 Hz), 3.82 (t, 2H, J=4.2 Hz), 3.58 (d, 2H, J=6.0 Hz), 3.00 (t, 2H, J=4.8 Hz).

LCMS: 408 (M+H$^+$) for C$_{18}$H$_{22}$FN$_5$O$_3$S.

EXAMPLE 63

Preparation of Compound 63

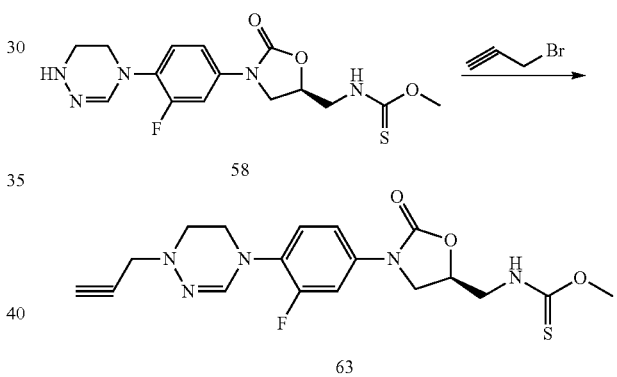

Compound 63 (36 mg, 0.089 mmol, 68%) was obtained from Compound 58 as in Example 60, using propargyl bromide instead of iodomethane.

$^1$H NMR (600 MHz, chloroform-d$_1$) δ 7.53 (dd, 1H, J$_1$=13.8 Hz, J$_2$=2.4 Hz), 7.16 (dd, 1H, J$_1$=9.0 Hz, J$_2$=2.4 Hz), 7.13 (t, 1H, 8.4 Hz), 6.96 (s, 1H), 6.69 (t, 1H, J=6.0 Hz), 4.98-4.90 (m, 1H), 4.14-3.98 (m, 3H), 4.01 (s, 3H), 3.90-3.82 (m, 1H), 3.85 (t, 2H, J=6.6 Hz), 3.83 (d, 2H, J=2.4 Hz), 3.13 (t, 2H, J=5.4 Hz), 2.31 (t, 1H, J=2.4 Hz).

LCMS: 406 (M+H$^+$) for C$_{18}$H$_{20}$FN$_5$O$_3$S.

EXAMPLE 64

Preparation of Compound 64

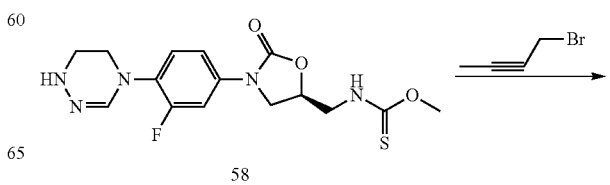
58

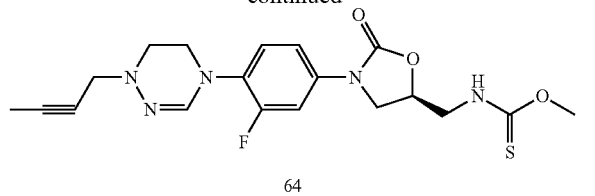

64

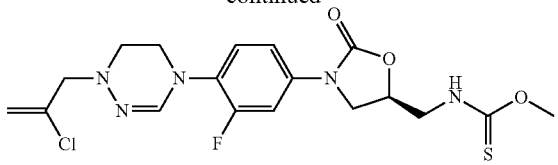

66

Compound 64 (16 mg, 0.038 mmol, 74%) was obtained from Compound 58 as in Example 60, using 1-bromo-2-butyne instead of iodomethane.

$^1$H NMR (600 MHz, CDCl$_3$) δ 7.52 (dd, J$_1$=13.8 Hz, J$_2$=2.4 Hz, 1H), 7.16 (dd, J$_1$=9.0 Hz, J$_2$=2.4 Hz, 1H), 7.12 (t, 8.4 Hz, 1H), 6.95 (s, 1H), 6.70 (t, J=6.0 Hz, 1H), 4.94 (m, 1H), 4.13-3.75 (m, 11H), 3.12 (t, J=5.4 Hz, 2H), 1.87 (t, J=2.4 Hz, 3H).

LCMS: 420 (M+H$^+$) for C$_{19}$H$_{22}$FN$_5$O$_3$S.

Compound 66 (15 mg, 0.034 mmol, 54%) was obtained from Compound 58 as in Example 60, using 2,3-dichloropropene instead of iodomethane.

$^1$H NMR (600 MHz, CDCl$_3$) δ 7.52 (dd, J$_1$=13.8 Hz, J$_2$=2.4 Hz, 1H), 7.16 (dd, J$_1$=9.0 Hz, J$_2$=2.4 Hz, 1H), 7.11 (t, 8.4 Hz, 1H), 6.92 (s, 1H), 6.73 (t, J=6.0 Hz, 1H), 5.49 (s, 1H), 5.42 (s, 1H), 4.94 (m, 1H), 4.12-3.84 (m, 9H), 3.72 (s, 2H), 3.08 (t, J=5.4 Hz, 2H).

LCMS: 442 (M+H$^+$) for C$_{18}$H$_{21}$ClFN$_5$O$_3$S.

EXAMPLE 65

Preparation of Compound 65

EXAMPLE 67

Preparation of Compound 67

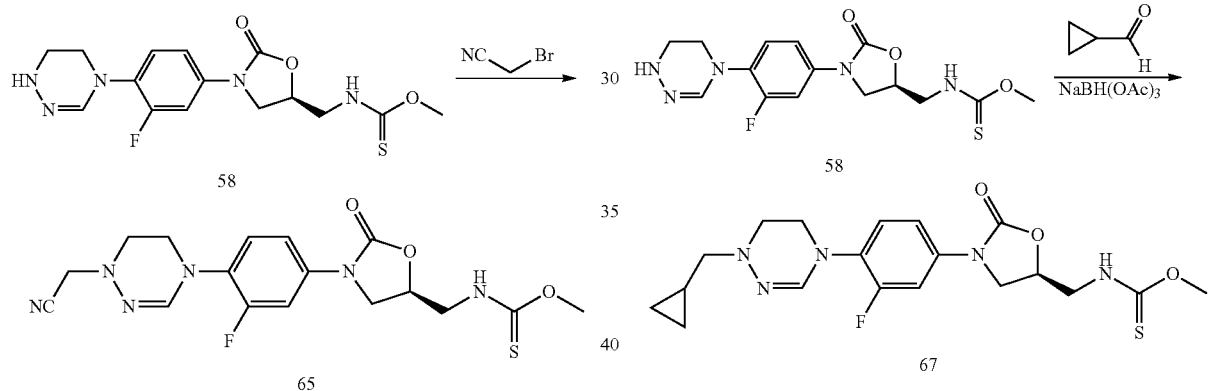

Compound 65 (22 mg, 0.054 mmol, 64%) was obtained from Compound 58 as in Example 60, using bromoacetonitrile instead of iodomethane.

$^1$H NMR (600 MHz, CDCl$_3$) δ 7.56 (dd, J$_1$=13.8 Hz, J$_2$=2.4 Hz, 1H), 7.17 (dd, J$_1$=9.0 Hz, J$_2$=2.4 Hz, 1H), 7.14 (t, 8.4 Hz, 1H), 6.96 (s, 1H), 6.68 (t, J=6.0 Hz, 1H), 4.95 (m, 1H), 4.12-3.86 (m, 11H), 3.15 (t, J=5.4 Hz, 2H).

LCMS: 407 (M+H$^+$) for C$_{17}$H$_{19}$FN$_6$O$_3$S.

Compound 67 (18 mg, 0.043 mmol, 84%) was obtained from Compound 58 as in Example 41, using cyclopropanecarboxaldehyde.

$^1$H NMR (600 MHz, CDCl$_3$) δ 7.51 (dd, J$_1$=13.8 Hz, J$_2$=2.4 Hz, 1H), 7.18 (dd, J$_1$=9.0 Hz, J$_2$=2.4 Hz, 1H), 7.11 (t, 8.4 Hz, 1H), 7.01 (t, J=6.0 Hz, 1H), 6.91 (s, 1H), 4.95 (m, 1H), 4.12-3.83 (m, 9H), 3.13 (t, J=4.8 Hz, 2H), 2.82 (d, J=7.2 Hz, 2H), 1.08 (m, 1H), 0.57 (m, 2H), 0.21 (m, 2H).

LCMS: 422 (M+H$^+$) for C$_{19}$H$_{24}$FN$_5$O$_3$S.

EXAMPLE 66

Preparation of Compound 66

EXAMPLE 68

Preparation of Compound 68

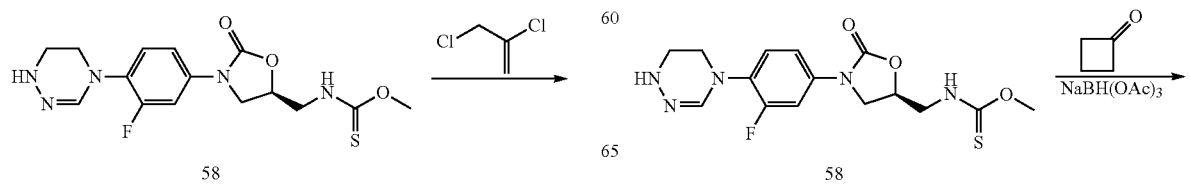

-continued

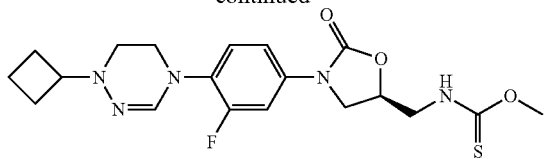

68

Compound 68 (19 mg, 0.045 mmol, 76%) was obtained from Compound 58 as in Example 41, using cyclobutanone.

$^1$H NMR (600 MHz, CDCl$_3$) δ 7.51 (dd, J$_1$=13.8 Hz, J$_2$=2.4 Hz, 1H), 7.16-7.09 (m, 2H), 6.95 (s, 1H), 6.64 (br, t, 1H), 4.94 (m, 1H), 4.11-3.98 (m, 6H), 3.87 (m, 1H), 3.82 (t, J=4.8 Hz, 2H), 3.42 (m, 1H), 2.91 (t, J=4.8 Hz, 2H), 2.23-2.12 (m, 4H), 1.81-1.73 (m, 2H).

LCMS: 422 (M+H$^+$) for C$_{19}$H$_{24}$FN$_5$O$_3$S.

EXAMPLE 69

Preparation of Compound 69

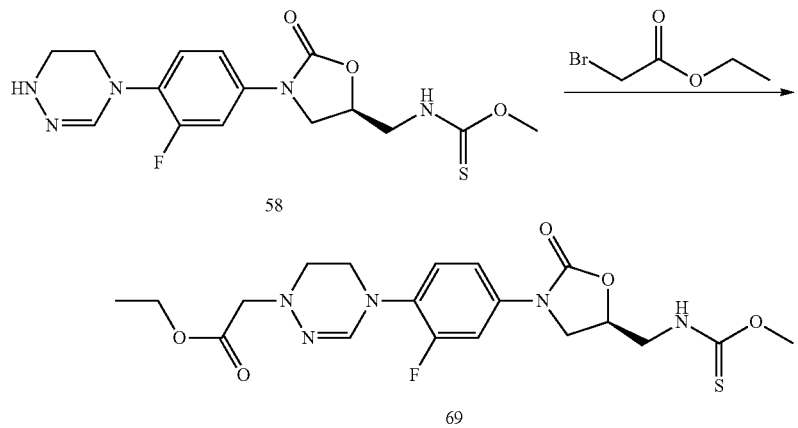

Compound 69 (24 mg, 0.053 mmol, 47%) was obtained from Compound 58 as in Example 60, using ethyl bromoacetate instead of iodomethane.

$^1$H NMR (600 MHz, chloroform-d$_1$) δ 7.52 (dd, 1H, J$_1$=13.2 Hz, J$_2$=1.8 Hz), 7.15 (dd, 1H, J$_1$=9.0 Hz, J$_2$=2.4 Hz), 7.11 (t, 1H, 8.4 Hz), 6.91 (s, 1H), 6.83 (t, 1H, J=6.6 Hz), 4.98-4.90 (m, 1H), 4.26-4.21 (m, 2H), 4.13-3.97 (m, 3H), 4.01 (s, 3H), 3.85 (t, 2H, J=4.2 Hz), 3.78 (s, 2H), 3.24 (t, 2H, J=4.8 Hz), 1.03 (t, 3H, J=7.2 Hz).

LCMS: 454 (M+H$^+$) for C$_{19}$H$_{24}$FN$_5$O$_5$S.

EXAMPLE 70

Preparation of Compound 70

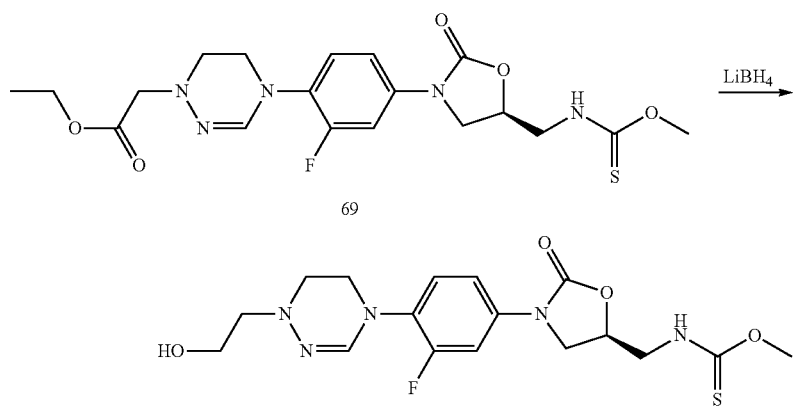

Compound 69 (17 mg, 0.037 mmol) was dissolved in THF (2 mL) and stirred at room temperature for 3 hours after adding 2M LiBH$_4$ solution (1 mL). After adding a small amount of water, the solution was separated by column chromatography to obtain Compound 70 (6.5 mg, 0.016 mmol, 43%) as a white solid.

$^1$H NMR (600 MHz, chloroform-d$_1$) δ 7.53 (dd, 1H, J$_1$=13.2 Hz, J$_2$=1.8 Hz), 7.17 (dd, 1H, J$_1$=8.4 Hz, J$_2$=2.4 Hz), 7.12 (t, 1H, 9.0 Hz), 6.90 (s, 1H), 6.73 (t, 1H, J=6.0 Hz), 4.98-4.90 (m, 1H), 4.18-4.04 (m, 2H), 4.04-3.98 (m, 1H), 4.01 (s, 3H), 3.96 (t, 2H, J=4.8 Hz), 3.87 (dd, 1H, J$_1$=9.0 Hz, J$_2$=7.2 Hz), 3.84 (t, 2H, J=4.8 Hz), 3.07 (t, 2H, J=4.8 Hz), 3.00 (t, 2H, J=4.8 Hz).

LCMS: 412 (M+H$^+$) for C$_{17}$H$_{22}$FN$_5$O$_4$S.

EXAMPLE 71

Preparation of Compound 71

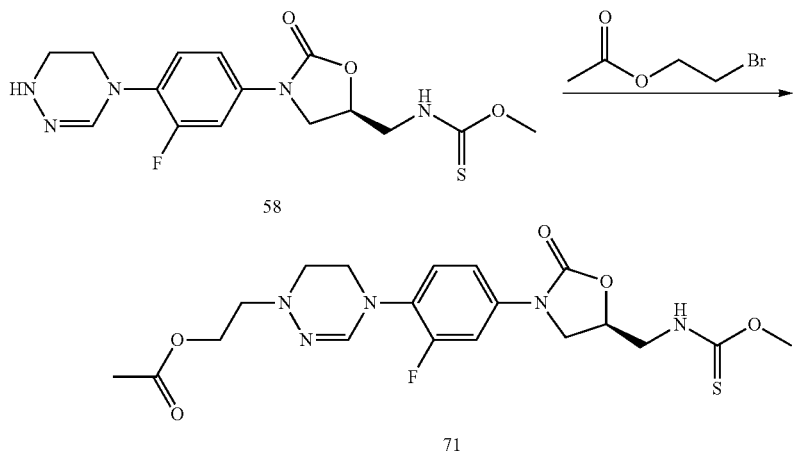

Compound 71 (84 mg, 0.19 mmol, 76%) was obtained from Compound 58 as in Example 60, using bromoethyl acetate instead of iodomethane.

$^1$H NMR (600 MHz, CDCl$_3$) δ 7.51 (dd, J$_1$=13.8 Hz, J$_2$=2.4 Hz, 1H), 7.16-7.07 (m, 2H), 6.91-6.89 (m, 2H), 4.95 (m, 1H), 4.40 (t, J=5.4 Hz, 2H) 4.13-3.86 (m, 7H), 3.83 (t, J=4.8 Hz, 2H), 3.15 (t, J=5.4 Hz, 2H), 3.09 (t, J=4.8 Hz, 2H), 2.10 (s, 3H).

LCMS: 454 (M+H$^+$) for C$_{19}$H$_{24}$FN$_5$O$_5$S.

EXAMPLE 72

Preparation of Compound 72

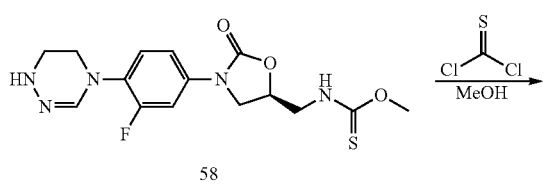

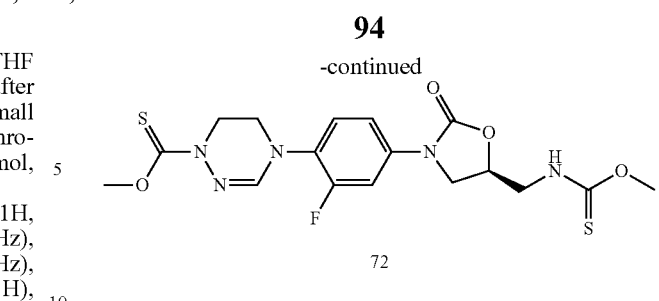

Compound 72 (54 mg, 0.12 mmol, 61%) was obtained from Compound 58 as in Example 53.

$^1$H NMR (600 MHz, DMSO-d$_6$) δ=9.56 (t, J=6 Hz, 1H), 7.62 (dd, J$_1$=14 Hz, J$_2$=2.0 Hz, 1H), 7.43 (t, J=9 Hz, 1H), 7.34 (dd, J$_1$=9 Hz, J$_2$=2.0 Hz, 7.17 (s, 1H), 4.92 (m, 1H), 4.41 (br, t, 2H), 4.17 (t, J$_1$=9 Hz, 1H), 3.99 (s, 3H), 3.88 (s, 3H), 3.85-3.76 (m, 5H).

LCMS: 442 (M+H$^+$) for C$_{17}$H$_{20}$FN$_5$O$_4$S$_2$.

EXAMPLE 73

Preparation of Compound 73

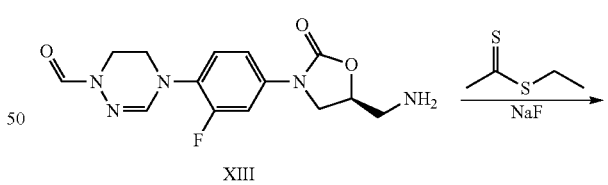

Compound XIII (223 mg, 0.69 mmol) and NaF (38 mg, 1.3 equivalents) were dissolved in ethanol (10 mL) and stirred overnight at room temperature after adding ethyl dithioacetate (0.1 mL, 1.2 equivalents). After distillation under reduced pressure, the mixture was dissolved in ethyl acetate, washed with brine, dried with sodium sulfate, and separated by column chromatography to obtain Compound 73 (220 mg, 0.58 mmol, 84%) as a white solid.

$^1$H NMR (600 MHz, CDCl$_3$) δ=8.52 (s, 1H) 7.91 (br, t, 1H), 7.56 (dd, J$_1$=13 Hz, J$_2$=2.4 Hz, 1H), 7.17 (dd, J$_1$=9.0 Hz, J$_2$=2.7 Hz, 1H), 7.11 (t, J=8.4 Hz, 1H), 6.87 (s, 1H), 4.98 (m, 1H), 4.28-4.24 (m, 1H), 4.12-4.07 (m 2H), 3.97 (t, J=4.8 Hz, 2H), 3.86-3.84 (m, 1H), 3.71 (t, J=4.8 Hz, 2H), 2.58 (s, 3H).

LCMS: 380 (M+H$^+$) for C$_{16}$H$_{18}$—FN$_5$O$_3$S.

EXAMPLE 74

Preparation of Compound 74

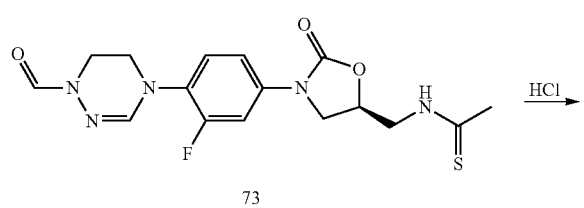

Compound 73 (220 mg, 0.58 mmol) was dissolved in methanol (10 mL) and stirred at room temperature for 2 hours after adding 4 M HCl dioxane solution (1 mL), and concentrated under reduced pressure to quantitatively obtain Compound 74 (240 mg) as hydrochloride salt form.

$^1$H NMR (400 MHz, DMSO-d$_6$) δ=10.5 (br, t, 1H), 7.70 (d, J=14 Hz, 1H), 7.61 (t, J=8.8 Hz, 1H), 7.42 (d, J=8.8 Hz, 1H), 5.00 (m, 1H), 4.20 (m, 1H), 3.94-3.78 (m, 5H), 3.62 (br, t, 2H), 2.45 (s, 3H).

LCMS: 352 (M+H$^+$) for C$_{15}$H$_{18}$—FN$_5$O$_2$S.

EXAMPLE 75

Preparation of Compound 75

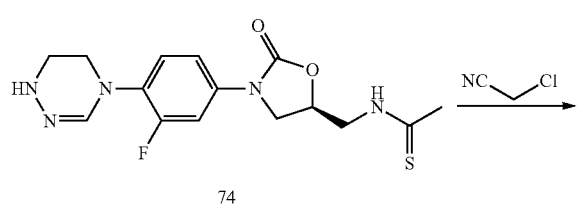

Compound 75 (35 mg, 0.090 mmol, 42%) was obtained from Compound 74 as in Example 7.

$^1$H NMR (600 MHz, CDCl$_3$) δ=7.74 (br, t, 1H), 7.55 (dd, J$_1$=14 Hz, J$_2$=1.8 Hz, 1H), 7.18-7.12 (m, 2H), 6.96 (s, 1H), 5.01 (m, 1H), 4.32 (m, 1H), 4.12-4.04 (m, 2H), 3.96 (s, 2H), 3.88-3.83 (m, 3H), 3.15 (t, J=4. Hz, 2H), 2.98-2.94 (m, 2H), 1.24 (t, J=4.2 Hz, 2H), 2.61 (s, 3H).

LCMS: 391 (M+H$^+$) for C$_{17}$H$_{19}$—FN$_6$O$_2$S.

EXAMPLE 76

Preparation of Compound 76

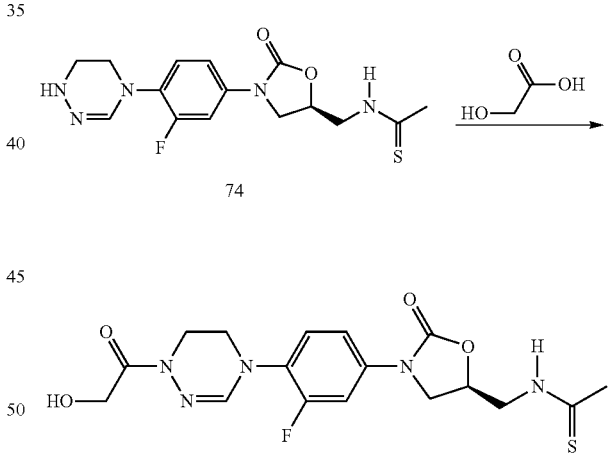

Compound 76 (35 mg, 0.086 mmol, 36%) was obtained from Compound 74 as in Example 12.

$^1$H NMR (600 MHz, CDCl$_3$) δ=7.80 (m, 1H), 7.56 (dd, J$_1$=13 Hz, J$_2$=2.4 Hz), 7.19-7.17 (m, 1H), 7.13-7.10 (m, 1H), 5.00-4.96 (m, 1H), 4.48 (d, J=4.2 Hz, 2H), 4.29-4.25 (m, 1H), 4.10-4.07 (m, 2H), 4.05 (t, J=4.8 Hz, 2H), 3.86-3.83 (m, 1H), 3.74 (t, J=4.8 Hz, 2H), 3.27 (t, J=4.8 Hz, 1H), 2.58 (s, 3H).

LCMS: 410 (M+H$^+$) for C$_{17}$H$_{20}$FN$_5$O$_4$S.

EXAMPLE 77

Preparation of Compound 77

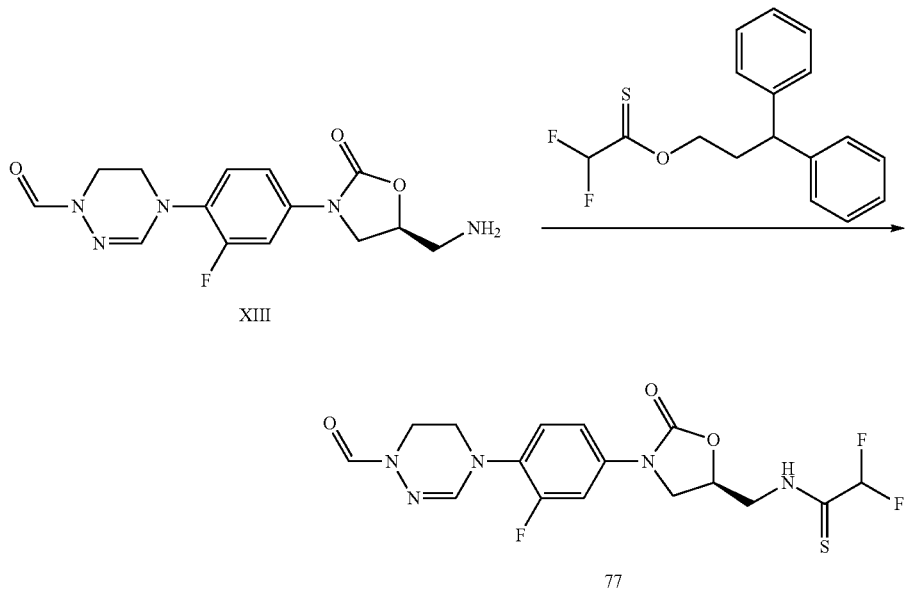

Compound 77 (350 mg, 0.84 mmol, 79%) was obtained by reacting Compound XIII with Ph$_2$CHCH$_2$CH$_2$OC(S)CHF$_2$ overnight at room temperature as in *Bioorg. Med. Chem. Lett.* 2006, 16, 3475-3478.

$^1$H NMR (400 MHz, CDCl$_3$) δ=8.55 (s, 1H), 8.48 (br, t, 1H), 7.56 (dd, J$_1$=14 Hz, J$_2$=2.0 Hz, 1H), 7.20 (dd, J$_1$=8.8 Hz, J$_2$=2.0 Hz, 1H), 7.14 (t, J=8.8 Hz, 1H), 6.89 (s, 1H), 6.22 (t, J=56 Hz, 1H), 5.03 (m, 1H), 4.34 (m, 1H), 4.16 (t, J=8.8 Hz, 1H), 4.06 (m, 1H), 3.99 (t, J=4.8 Hz, 2H), 3.82-3.73 (m, 3H).

*LCMS: 416 (M+H$^+$) for C$_{16}$H$_{16}$F$_3$N$_5$O$_3$S.

EXAMPLE 78

Preparation of Compound 78

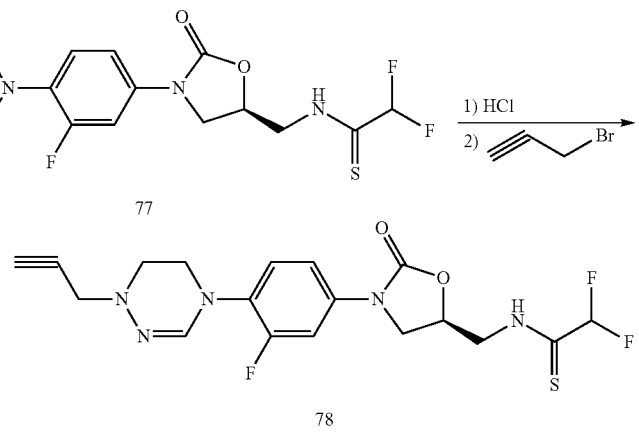

Compound 77 was reacted as Example 74. Then, Compound 78 (26 mg, 0.061 mmol, 35%) was obtained as in Example 5.

$^1$H NMR (600 MHz, CDCl$_3$) δ=8.65 (br, t, 1H), 7.49 (dd, J$_1$=14 Hz, J$_2$=2.0 Hz, 1H), 7.14-7.13 (m, 2H), 6.96 (s, 1H), 6.22 (t, J=56 Hz, 1H), 5.03 (m, 1H), 4.34 (m, 1H), 4.15 (t, J=8.8 Hz, 1H), 4.04 (m, 1H), 3.86-3.78 (m, 5H), 3.14 (t, J=4.8 Hz, 2H), 2.31 (t, J=1.8 Hz, 1H).

LCMS: 426 (M+H$^+$) for C$_{18}$H$_{18}$F$_3$N$_5$O$_2$S.

EXAMPLE 79

Preparation of Compound 79

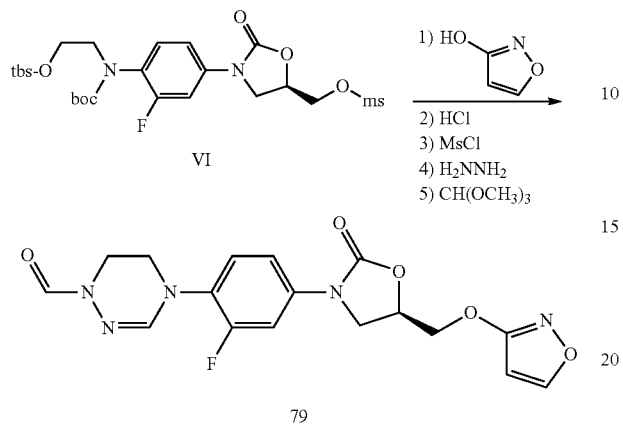

Compound VI prepared in Preparation Example 6 was reacted as in Preparation Example 12, using hydroxyisoxazole instead of boc-aminoisoxazole. Then, Compound 79 (53 mg, 0.14 mmol, 28%) was obtained as in Preparation Example 10.

$^1$H NMR (400 MHz, DMSO-d$_6$) δ=8.71 (d, J=2 Hz, 1H), 8.42 (s, 1H), 7.65 (dd, J$_1$=14 Hz, J$_2$=2.0 Hz, 1H), 7.41-7.37 (m, 2H), 7.07 (s, 1H), 6.39 (d, J=2Hz, 1H), 5.10 (m, 1H), 4.81 (m, 1H), 4.49 (m, 1H), 4.21 (t, J=9.2 Hz, 1H), 3.93 (m, 1H), 3.84 (t, J=5.6 Hz, 2H), 3.70 (t, J=4.8 Hz, 2H).

LCMS: 390 (M+H$^+$) for C$_{17}$H$_{16}$—FN$_5$O$_5$.

EXAMPLE 80

Preparation of Compound 80

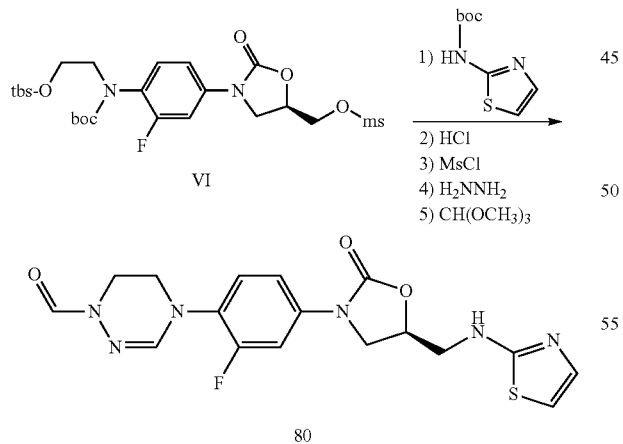

Compound VI was reacted as in Preparation Example 12, using boc-aminothiazole instead of boc-aminoisoxazole. Then, Compound 80 (26 mg, 0.064 mmol, 16%) was obtained as in Preparation Example 10.

$^1$H NMR (400 MHz, CDCl$_3$) δ=8.55 (s, 1H), 7.57 (dd, J$_1$=13 Hz, J$_2$=2.4 Hz, 1H), 7.21 (dd, J$_1$=9.0 Hz, J$_2$=2.7 Hz, 1H), 7.13-7.08 (m, 2H), 6.84 (s, 1H), 6.55 (d, J=3.6 Hz, 1H), 5.34 (br, s, 1H), 4.97 (m, 1H), 4.10 (t, J=8.8 Hz, 1H), 3.99 (t, J=5.4 Hz, 2H), 3.92-3.79 (m, 3H), 3.73 (t, J=5.4 Hz, 2H).

LCMS: 405 (M+H$^+$) for C$_{17}$H$_{17}$—FN$_6$O$_3$S.

EXAMPLE 81

Preparation of Compound 81

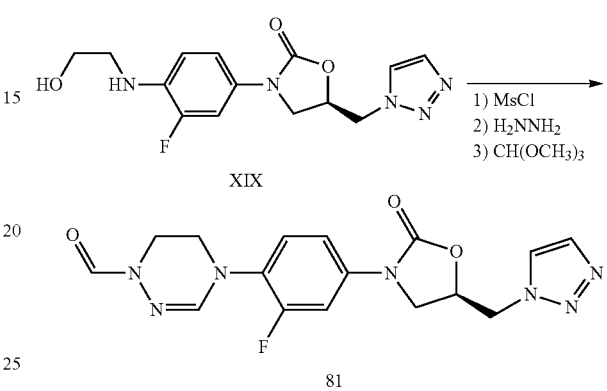

Compound 81 (35 mg, 0.094 mmol, 25%) was obtained from Compound XIX as in Preparation Example 10.

$^1$H NMR (400 MHz, CDCl$_3$) δ=8.49 (s, 1H), 7.77 (d, J=1 Hz, 1H), 7.71 (s, 1H), 7.41 (dd, J$_1$=13 Hz, J$_2$=2.4 Hz, 1H), 7.08-7.04 (m, 2H), 6.84 (d, J=1 Hz, 1H), 6.86 (s, 1H), 5.06 (m, 1H), 4.78 (d, J=4 Hz, 2H), 4.14 (t, J=8.8 Hz, 1H), 3.94-3.64 (m, 7H).

LCMS: 374 (M+H$^+$) for C$_{16}$H$_{16}$—FN$_7$O$_3$.

EXAMPLE 82

Preparation of Compound 82

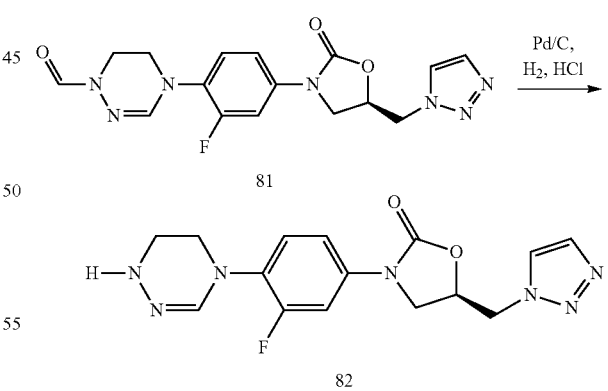

Compound 82 (84 mg, 0.24 mmol, 73%) was obtained from Compound 81 as in Example 2.

$^1$H NMR (400 MHz, DMSO-d$_6$) δ=8.37 (s, 1H), 8.19 (s, 1H), 7.77 (s, 1H), 7.64-7.56 (m, 2H), 7.35 (dd, J$_1$=9.0 Hz, J$_2$=2.4 Hz, 1H), 7.08-7.04 (m, 2H), 5.18 (m, 1H), 4.85 (d, J=5.2 Hz, 2H), 4.27 (t, J=9.2 Hz, 1H), 3.93 (m, 1H), 3.78 (br, t, 2H), 3.35 (br, t, 2H).

LCMS: 346 (M+H$^+$) for C$_{15}$H$_{16}$—FN$_7$O$_2$.

EXAMPLE 83

Preparation of Compound 83

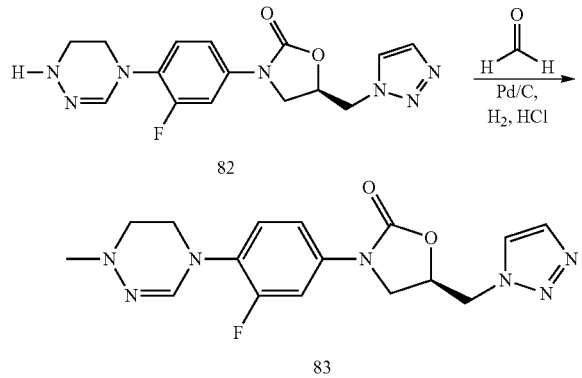

Compound 82 (62 mg, 0.16 mmol) was dissolved in methanol (5 mL) and reacted for 2 hours at room temperature under hydrogen balloon after adding 4 M HCl dioxane solution (0.1 mL), formalin (0.2 mL) and Pd/C (6 mg). The solution was filtered with celite, dissolved in distilled water (10 mL), neutralized, extracted with dichloromethane, dried with sodium sulfate, and concentrated under reduced pressure to obtain Compound 83 (34 mg, 0.086 mmol, 54%).

$^1$H NMR (400 MHz, CDCl$_3$) δ=7.78 (s, 1H), 7.75 (s, 1H), 7.39-7.00 (m, 3H), 6.88 (s, 1H), 5.08 (m, 1H), 4.80 (d, J=4.4 Hz, 2H), 4.15 (t, J=9.2 Hz, 1H), 3.95 (m, 1H), 3.80 (t, J=4.6 Hz, 2H), 2.98 (t, J=4.6 Hz, 2H) 2.79 (s, 3H).

LCMS: 360 (M+H$^+$) for $C_{16}H_{18}$—FN$_7$O$_2$.

EXAMPLE 84

Preparation of Compound 84

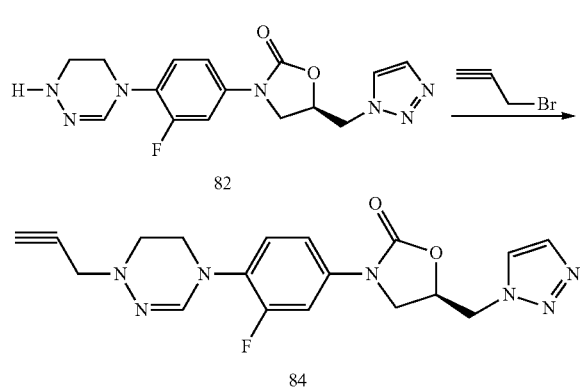

Compound 84 (26 mg, 0.068 mmol, 74%) was obtained from Compound 82 as in Example 5.

$^1$H NMR (400 MHz, CDCl$_3$) δ=7.79 (s, 1H), 7.76 (s, 1H), 7.39-7.03 (m, 3H), 6.94 (s, 1H), 5.08 (m, 1H), 4.80 (d, J=3.6 Hz, 2H), 4.15 (t, J=9.2 Hz, 1H), 3.95 (m, 1H), 3.84-3.82 (m, 4H), 3.12 (br, t, 2H), 2.34 (s, 1H).

LCMS: 384 (M+H$^+$) for $C_{18}H_{18}$—FN$_7$O$_2$.

EXAMPLE 85

Preparation of Compound 85

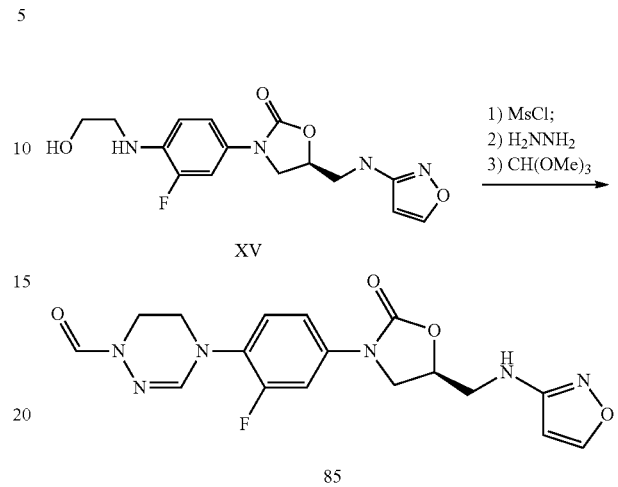

Compound 85 (81 mg, 0.21 mmol, 31%) was obtained from Compound XV as in Preparation Example 10.

$^1$H NMR (400 MHz, CDCl$_3$) δ=8.49 (s, 1H), 8.02 (d, J=2.0 Hz, 1H), 7.54 (dd, J$_1$=13 Hz, J$_2$=2.4 Hz, 1H), 7.17 (dd, J$_1$=9.0 Hz, J$_2$=2.7 Hz, 1H), 7.08 (t, J=8.4 Hz, 1H), 6.86 (s, 1H), 5.86 (d, J=2.0 Hz, 1H), 4.93 (m, 1H), 4.06 (t, J=8.8 Hz, 1H), 3.94 (t, J=5.0 Hz, 2H), 3.87-3.57 (m, 5H).

LCMS: 389 (M+H$^+$) for $C_{17}H_{17}$—FN$_6$O$_4$.

EXAMPLE 86

Preparation of Compound 86

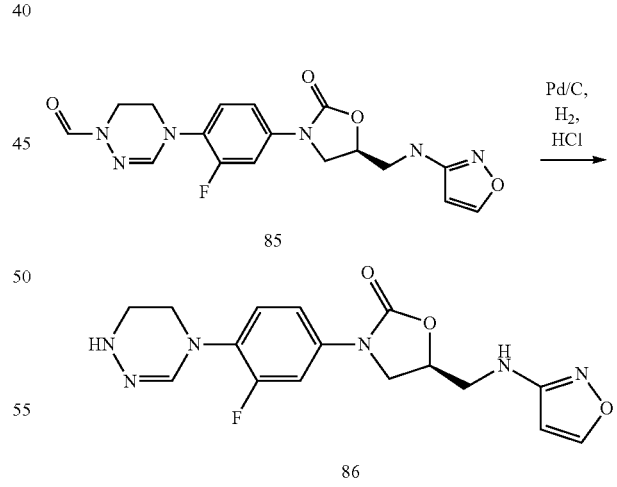

Compound 86 (35 mg, 0.097 mmol, 71%) was obtained from Compound 85 as in Example 2.

$^1$H NMR (600 MHz, DMSO-d$_6$) δ=8.40 (s, 1H), 8.30 (s, 1H), 7.70 (d, J=13 Hz, 1H), 7.60 (t, J=8.4 Hz, 1H), 7.41 (d, J=8.4 Hz, 1H), 6.03 (s, 1H), 5.86 (d, J=2.0 Hz, 1H), 4.92 (m, 1H), 4.20 (t, J=7.8 Hz, 1H), 3.89-3.36 (m, 7H).

LCMS: 361 (M+H$^+$) for $C_{16}H_{17}$—FN$_6$O$_3$.

EXAMPLE 87

Preparation of Compound 87

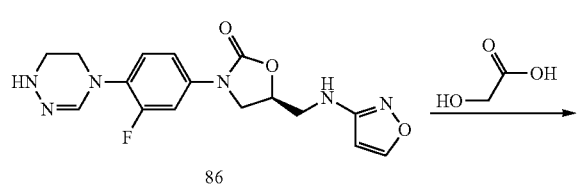

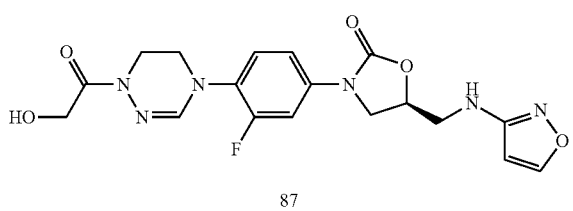

Compound 87 (15 mg, 0.036 mmol, 35%) was obtained from Compound 86 as in Example 12.

$^1$H NMR (600 MHz, DMSO-d$_6$) δ=8.39 (d, J=1.2 Hz, 1H), 7.62 (dd, J$_1$=14 Hz, J$_2$=2.4 Hz, 1H), 7.38-7.33 (m, 1H), 7.07 (s, 1H), 6.56 (t, J=6 Hz, 1H), 6.00 (d, J=1.2 Hz, 1H), 4.91-4.87 (m, 1H), 4.54-4.52 (m, 1H), 4.32 (d, J=6.0 Hz, 2H), 4.18-4.15 (m, 1H), 3.89 (t, J=4.8 Hz, 2H), 3.83-3.80 (m, 1H), 3.70 (t, J=4.8 Hz, 2H), 3.46-3.43 (m, 2H).

LCMS: 419 (M+H$^+$) for C$_{18}$H$_{19}$—FN$_6$O$_5$.

EXAMPLE 88

Preparation of Compound 88

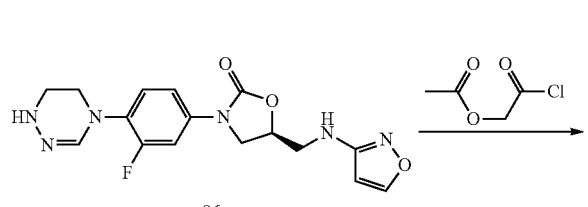

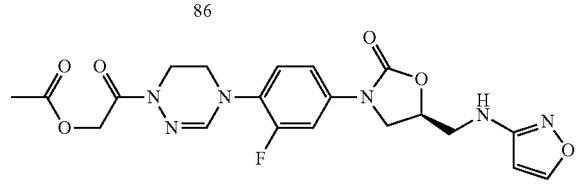

Compound 88 (210 mg, 0.46 mmol, 42%) was obtained from Compound 86 as in Example 59.

$^1$H NMR (600 MHz, CDCl$_3$) δ=8.07 (d, 1H, J=1.8 Hz), 7.58 (dd, 1H, J$_1$=13.2 Hz, J$_2$=3.0 Hz), 7.21 (dd, 1H J$_1$=8.4 Hz, J$_2$=2.4 Hz), 7.11 (t, 1H, J=8.4 Hz), 6.82 (s, 1H), 5.88 (d, 1H, J=1.8 Hz), 5.08 (s, 2H), 4.96-5.00 (m, 1H), 4.40 (t, 1H, J=6.6 Hz), 4.09 (t, 1H, J=9.0 Hz), 4.02 (t, 2H, J=4.8 Hz), 3.77-3.78 (m, 1H), 3.74-3.76 (m, 1H), 3.66-3.62 (m, 1H).

LCMS: 461 (M+H$^+$) for C$_{20}$H$_{21}$—FN$_6$O$_6$.

EXAMPLE 89

Preparation of Compound 89

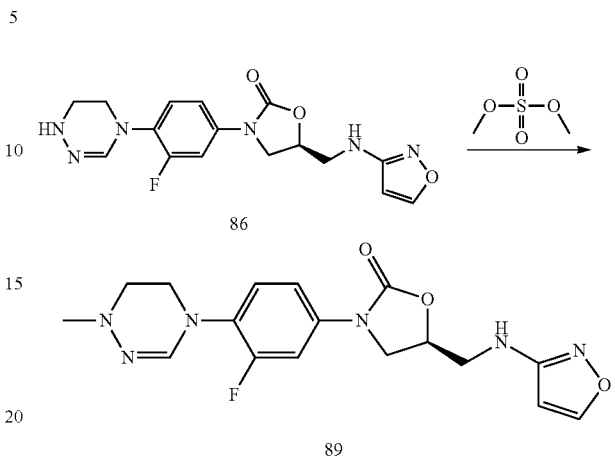

Compound 89 (36 mg, 0.096 mmol, 68%) was obtained from Compound 86 as in Example 3.

$^1$H NMR (600 MHz, CDCl$_3$) δ 8.07 (d, J=1.2 Hz, 1H), 7.51 (dd, J$_1$=13.8 Hz, J$_2$=2.4 Hz, 1H), 7.15 (dd, J$_1$=9.0 Hz, J$_2$=2.4 Hz, 1H), 7.09 (t, 8.4 Hz, 1H), 6.89 (s, 1H), 5.87 (d, J=1.2 Hz 1H), 4.97 (m, 1H), 4.42 (t, J=6 Hz, 1H), 4.08 (t, J=8.4 Hz, 1H), 3.87-3.60 (m, 5H), 2.98 (t, J=4.8 Hz, 2H), 2.79 (s, 3H).

LCMS: 375 (M+H$^+$) for C$_{17}$H$_{19}$—FN$_6$O$_3$.

EXAMPLE 90

Preparation of Compound 90

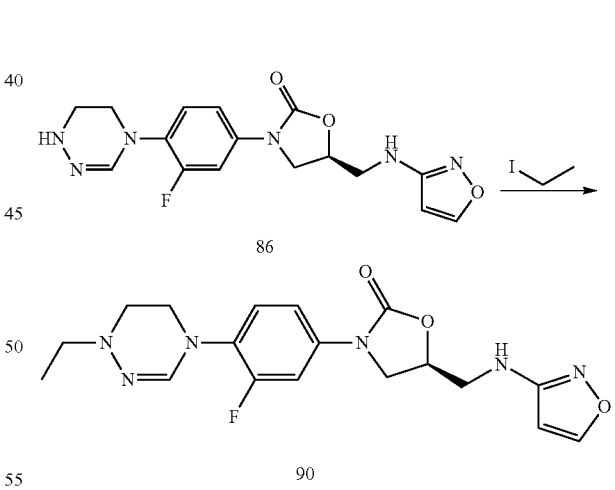

Compound 90 (15 mg, 0.039 mmol, 45%) was obtained from Compound 86 as in Example 6.

$^1$H NMR (400 MHz, CDCl$_3$) δ=8.07 (d, 1H, J=1.6 Hz), 7.51 (dd, 1H, J$_1$=13.6 Hz, J$_2$=2.4 Hz), 7.15 (dd, 1H, J$_1$=9.2 Hz, J$_2$=2.4 Hz), 7.09 (t, 1H, J=8.8 Hz), 6.91 (s, 1H), 5.87 (dd, 1H, J=1.6 Hz), 4.99-4.93 (m, 1H), 4.40 (t, 1H, J=6.4 Hz), 4.07 (t, 1H, J=9.0 Hz), 3.86-3.81 (m, 3H), 3.78-3.72 (m, 1H), 3.64 (t, 1H, J=3.2 Hz), 3.62-3.58 (m, 1H), 3.01 (t, 2H, J=4.8 Hz), 2.95 (t, 2H, J=7.07 Hz), 1.23 (t, 3H, J=7.0 Hz).

LCMS: 389 (M+H$^+$) for C$_{18}$H$_{21}$—FN$_6$O$_3$.

EXAMPLE 91

Preparation of Compound 91

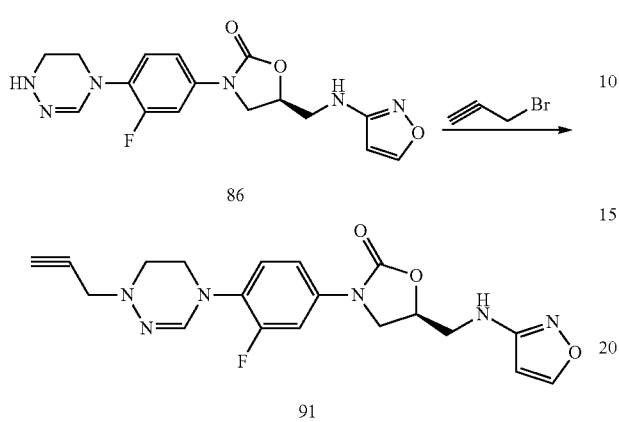

Compound 91 (25 mg, 0.063 mmol, 64%) was obtained from Compound 86 as in Example 5.

$^1$H NMR (600 MHz, CDCl$_3$) δ 8.07 (d, J=1.8 Hz, 1H), 7.53 (dd, J$_1$=13.8 Hz, J$_2$=2.4 Hz, 1H), 7.16 (dd, J$_1$=9.0 Hz, J$_2$=2.4 Hz, 1H), 7.11 (t, 8.4 Hz, 1H), 6.95 (s, 1H), 5.87 (d, J=1.8 Hz 1H), 4.96 (m, 1H), 4.35 (t, J=6.6 Hz, 1H), 4.08 (t, J=9 Hz, 1H), 3.87-3.60 (m, 7H), 3.13 (t, J=4.8 Hz, 2H), 2.31 (t, J=2.4 Hz, 1H).

LCMS: 399 (M+H$^+$) for C$_{19}$H$_{19}$—FN$_6$O$_3$.

EXAMPLE 92

Preparation of Compound 92

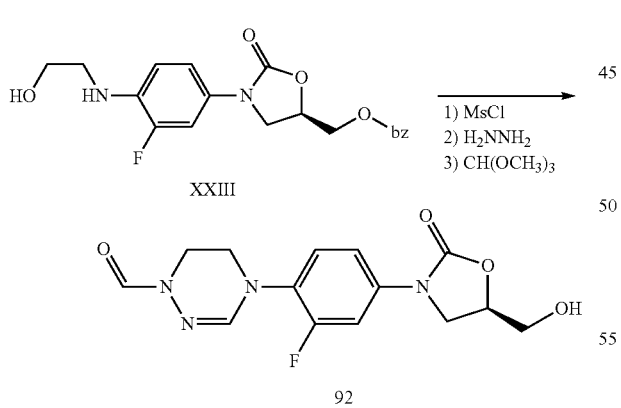

Compound 92 (240 mg, 0.75 mmol, 32%) was obtained from Compound XXIII as in Preparation Example 10.

$^1$H NMR (600 MHz, CDCl$_3$) δ=8.55 (s, 1H), 7.61 (dd, J$_1$=13 Hz, J$_2$=2.4 Hz, 1H), 7.25 (dd, J$_1$=9.0 Hz, J$_2$=2.7 Hz, 1H), 7.14 (t, J=8.4 Hz, 1H), 6.90 (s, 1H), 4.79 (m, 1H), 4.04-3.99 (m, 5H), 3.79-3.73 (m, 3H), 2.58 (br, s, 1H).

LCMS: 323 (M+H$^+$) for C$_{14}$H$_{15}$—FN$_4$O$_4$.

EXAMPLE 93

Preparation of Compound 93

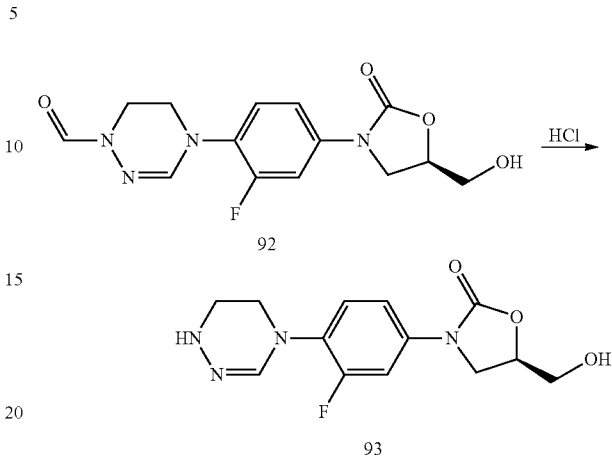

Compound 93 (190 mg, 0.65 mmol, 74%) was obtained from Compound 92 as in Example 2.

$^1$H NMR (600 MHz, DMSO-d$_6$) δ=7.73 (dd, J$_1$=13.8 Hz, J$_2$=2.4 Hz, 1H), 7.60 (t, J=9 Hz, 1H), 7.45 (dd, J$_1$=9.0 Hz, J$_2$=2.4 Hz, 1H), 4.75 (m, 1H), 4.11 (t, J=9.0 Hz, 1H), 3.88 (m, 1H), 3.78 (t, J=4.8 Hz, 2H), 3.70-3.55 (m, 2H), 3.36 (t, J=4.8 Hz, 2H).

LCMS: 295 (M+H$^+$) for C$_{13}$H$_{15}$—FN$_4$O$_3$.

EXAMPLE 94

Preparation of Compound 94

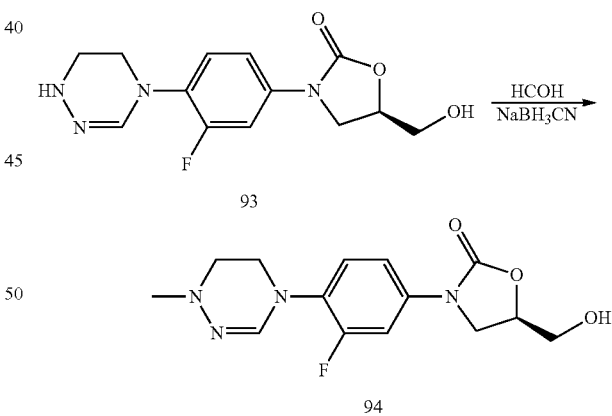

Compound 93 (150 mg, 0.51 mmol) was dissolved in methanol (5 mL), formaldehyde (37% aqueous solution, 0.21 mL, 2.55 mmol) and stirred for 1 hour at room temperature after adding acetic acid (0.03 mL, 0.51 mmol) and NaBH$_3$CN (48 mg, 0.77 mmol). The solution was distilled under reduced pressure, dissolved in dichloromethane (100 mL), sequentially washed with saturated aqueous sodium bi-carbonate solution and saturated aqueous sodium chloride solution (brine), dried with anhydrous sodium sulfate, concentrated under reduced pressure, and separated by column chromatography to obtain Compound 94 (71 mg, 0.23 mmol, 45%).

¹H NMR (600 MHz, DMSO-d₆) δ=7.59 (dd, J₁=13.8 Hz, J₂=2.4 Hz, 1H), 7.33-7.30 (m, 2H), 6.84 (s, 1H), 5.23 (t, J=5.4 Hz, 1H), 4.70 (m, 1H), 4.07 (t, J=9.0 Hz, 1H), 3.82 (m, 1H), 3.71 (t, J=4.8 Hz, 2H), 3.69-3.54 (m, 2H), 2.87 (t, J=4.8 Hz, 2H), 2.61 (s, 3H).

LCMS: 309 (M+H⁺) for C₁₄H₁₇—FN₄O₃.

EXAMPLE 95

Preparation of Compound 95

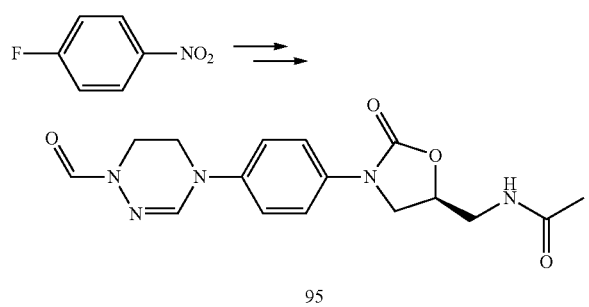

95

Compound 95 (300 mg, 0.86 mmol) was obtained from 4-fluoronitrobenzene according to Scheme 6, as in the synthesis of Compound 1.

¹H NMR (600 MHz, CDCl₃) δ=8.56 (s, 1H), 7.55 (m, 2H), 7.11 (s, 1H), 7.07 (m, 2H), 6.00 (br, t, 1H), 4.79 (m, 1H), 4.07 (t, J=9.6 Hz, 1H), 4.02 (t, J=4.8 Hz, 2H), 3.81 (m, 1H), 3.76 (t, J=4.8 Hz, 2H), 3.72-3.61 (m, 2H), 2.03 (s, 3H).

LCMS: 346 (M+H⁺) for C₁₆H₁₉N₅O₄.

EXAMPLE 96

Preparation of Compound 96

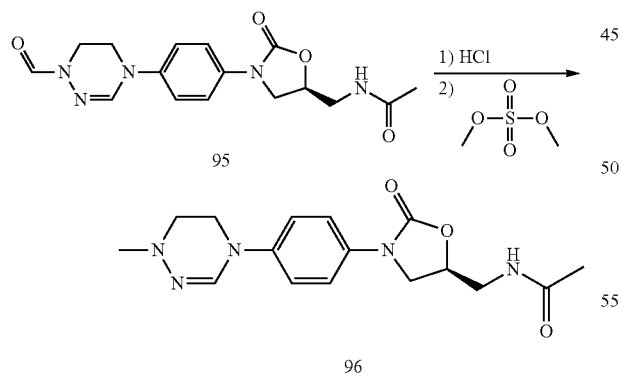

Compound 96 (42 mg, 0.13 mmol, 48%) was obtained from Compound 95 as in Example 3.

¹H NMR (600 MHz, CDCl₃) δ=7.48 (d, J=9.0 Hz, 2H), 7.22 (s, 1H), 7.02 (d, J=9.0 Hz, 2H), 5.93 (br, t, 1H), 4.77 (m, 1H), 4.05 (t, J=9.6 Hz, 1H), 3.81 (t, J=4.8 Hz, 2H), 3.79-3.58 (m, 3H), 3.01 (t, J=4.8 Hz, 2H), 2.80 (s, 3H), 2.03 (s, 3H).

LCMS: 332 (M+H⁺) for C₁₆H₂₁N₅O₃.

EXAMPLE 97

Preparation of Compound 97

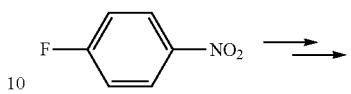

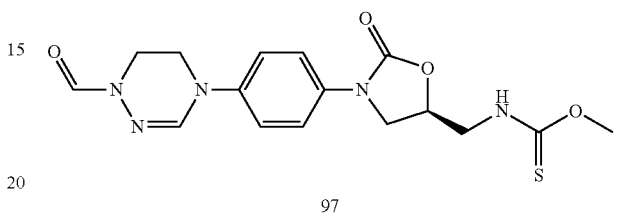

97

Compound 97 (540 mg, 1.4 mmol) was obtained from 4-fluoronitrobenzene according to Scheme 6, as in the synthesis of Compound 53.

¹H NMR (600 MHz, CDCl₃) δ=8.56 (s, 1H), 7.55 (d, J=9.0 Hz, 2H), 7.11 (s, 1H), 7.07 (d, J=9.0 Hz, 2H), 6.69 (br, t, 1H), 4.94 (m, 1H), 4.13-4.05 (m, 3H), 4.04-3.99 (m, 5H), 3.90 (m, 1H), 3.76 (t, J=4.8 Hz, 2H).

LCMS: 378 (M+H⁺) for C₁₆H₁₉N₅O₄S.

EXAMPLE 98

Preparation of Compound 98

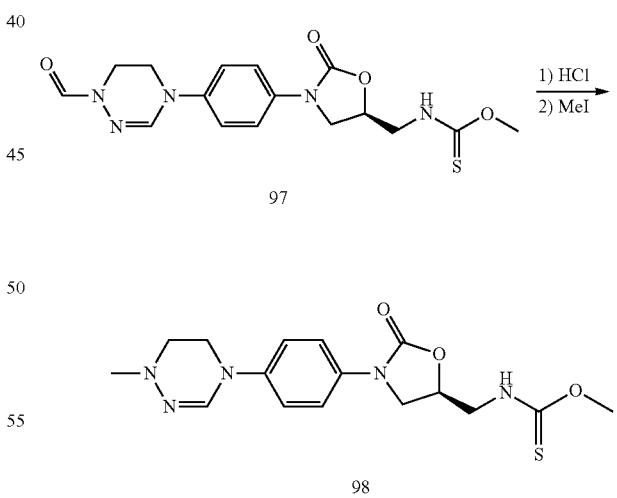

Compound 98 (160 mg, 0.44 mmol, 62%) was obtained from Compound 97 as in Example 60.

¹H NMR (600 MHz, CDCl₃) δ=7.48 (d, J=9.0 Hz, 2H), 7.21 (s, 1H), 7.02 (d, J=9.0 Hz, 2H), 6.69 (br, t, 1H), 4.92 (m, 1H), 4.13-4.08 (m, 2H), 4.01-3.95 (m, 4H), 3.86 (m, 1H), 3.81 (t, J=4.8 Hz, 2H), 3.01 (t, J=4.8 Hz, 2H), 2.80 (s, 3H).

LCMS: 364 (M+H⁺) for C₁₆H₂₁N₅O₃S.

EXAMPLE 99

Preparation of Compound 99

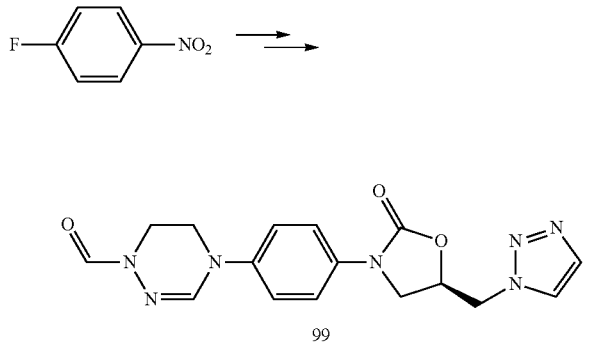

Compound 99 (340 mg, 0.96 mmol) was obtained from 4-fluoronitrobenzene according to Scheme 6, as in the synthesis of Compound 81.

$^1$H NMR (600 MHz, CDCl$_3$) δ=8.55 (s, 1H), 7.80 (d, J=1 Hz, 1H), 7.75 (d, J=1 Hz, 1H), 7.40 (d, J=9.0 Hz, 2H), 7.09 (s, 1H), 7.03 (d, J=9.0 Hz, 2H), 5.08 (m, 1H), 4.81 (d, J=4 Hz, 2H), 4.17 (t, J=8.4 Hz, 1H), 4.00-3.97 (m, 4H), 3.73 (t, J=4.8 Hz, 2H).

LCMS: 356 (M+H$^+$) for C$_{16}$H$_{17}$—N$_7$O$_3$.

EXAMPLE 100

Preparation of Compound 100

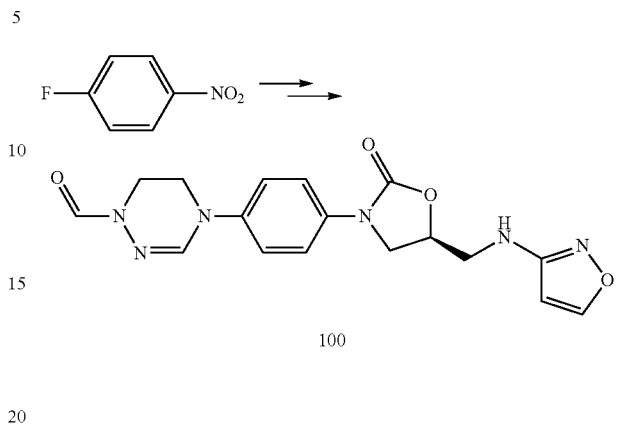

Compound 100 (280 mg, 0.76 mmol) was obtained from 4-fluoronitrobenzene according to Scheme 6, as in the synthesis of Compound 85.

$^1$H NMR (600 MHz, CDCl$_3$) δ=8.55 (s, 1H), 8.06 (d, J=1.8 Hz, 1H), 7.54 (d, J=9 Hz, 2H), 7.10 (s, 1H), 7.06 (d, J=9 Hz, 2H), 5.89 (d, J=1.8 Hz, 1H), 4.96 (m, 1H), 4.10 (t, J=9 Hz, 1H), 3.99 (t, J=4.8 Hz, 2H), 3.89 (m, 1H), 3.75-3.72 (m, 3H), 3.62 (m, 1H).

LCMS: 371 (M+H$^+$) for C$_{17}$H$_{18}$—N$_6$O$_4$.

EXAMPLE 101

Preparation of Compound 101

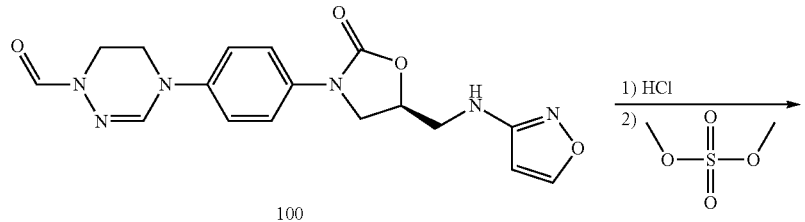

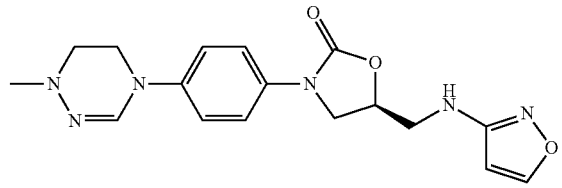

Compound 101 (37 mg, 0.10 mmol, 68%) was obtained from Compound 100 as in Example 89.

$^1$H NMR (600 MHz, CDCl$_3$) δ=8.07 (s, 1H), 7.48 (d, J=9 Hz, 2H), 7.21 (s, 1H), 7.01 (d, J=9 Hz, 2H), 5.87 (s, 1H), 4.95 (m, 1H), 4.40 (br, t, J=6 Hz, 1H), 4.09 (t, J=9 Hz, 1H), 3.85 (t, J=8.4 Hz, 1H), 3.80 (t, J=4.8 Hz, 2H), 3.89 (m, 1H), 3.76-3.59 (m, 2H), 3.00 (t, J=4.8 Hz, 2H), 2.80 (s, 3H).

LCMS: 357 (M+H$^+$) for C$_{17}$H$_{20}$—N$_6$O$_3$.

EXAMPLE 102

Preparation of Compound 102

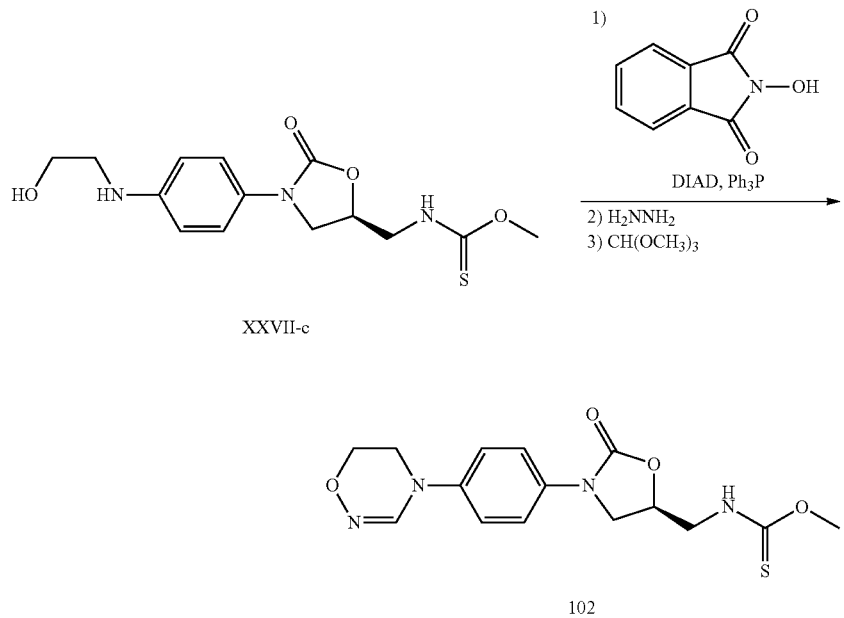

Compound 102 (24 mg, 0.069 mmol, 37%) was obtained from Compound XXVII-c, which was prepared from 4-fluoronitrobenzene according to Scheme 6 as in Preparation Example 14, as in Example 57.

$^1$H NMR (600 MHz, CDCl$_3$) δ=7.56 (s, 1H), 7.54 (d, J=9 Hz, 2H), 7.06 (d, J=9 Hz, 2H), 6.67 (br, t, 1H), 4.93 (m, 1H), 4.21 (t, J=4.8 Hz, 2H), 4.13-4.07 (m, 3H), 4.01 (s, 3H), 3.88 (t, J=9 Hz, 1H), 3.77 (t, J=4.8 Hz, 2H).

LCMS: 351 (M+H$^+$) for C$_{15}$H$_{18}$—N$_4$O$_4$S.

EXAMPLE 103

Preparation of Compound 103

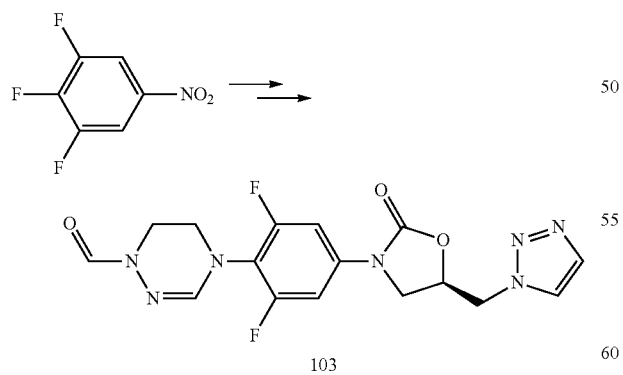

Compound 103 (350 mg, 0.90 mmol) was obtained from 3,4,5-trifluoronitrobenzene according to Scheme 6, as in the synthesis of Compound 81.

$^1$H NMR (600 MHz, CDCl$_3$) δ=8.54 (s, 1H), 7.77 (d, J=1 Hz, 1H), 7.75 (d, J=1 Hz, 1H), 7.15 (s, 1H), 7.13 (s, 1H), 6.69 (s, 1H), 5.11 (m, 1H), 4.81 (d, J=4 Hz, 2H), 4.15 (t, J=8.8 Hz, 1H), 4.02-3.98 (m, 3H), 3.65 (t, J=4.8 Hz, 2H).

LCMS: 392 (M+H$^+$) for C$_{16}$H$_{15}$—F$_2$N$_7$O$_3$.

EXAMPLE 104

Preparation of Compound 104

Compound 104 (23 mg, 0.061 mmol, 62%) was obtained from Compound 103 as in Example 83.

$^1$H NMR (400 MHz, CDCl$_3$) δ=7.79 (s, 1H), 7.74 (s, 1H), 7.11 (s, 1H), 7.09 (s, 1H), 6.65 (s, 1H), 5.11 (m, 1H), 4.81 (d, J=4 Hz, 2H), 4.16 (t, J=9 Hz, 1H), 3.95 (m, 1H), 3.73 (t, J=4.8 Hz, 2H), 2.99 (t, J=4.8 Hz, 2H).

LCMS: 378 (M+H$^+$) for C$_{16}$H$_{17}$—F$_2$N$_7$O$_2$.

EXAMPLE 105

Preparation of Compound 105

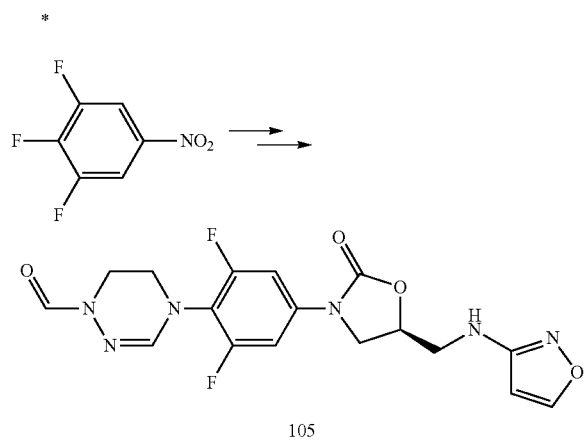

105

Compound 105 (640 mg, 1.6 mmol) was obtained from 3,4,5-trifluoronitrobenzene according to Scheme 6, as in the synthesis of Compound 85.

$^1$H NMR (400 MHz, CDCl$_3$) δ=8.54 (s, 1H), 8.08 (d, J=1.6 Hz, 1H), 7.29 (s, 1H), 7.27 (s, 1H), 6.71 (s, 1H), 5.89 (d, J=1.6 Hz, 1H), 4.99 (m, 1H), 4.54 (t, J=6.4 Hz, 1H), 4.08 (t, J=9 Hz, 1H), 4.00 (t, J=4.8 Hz, 2H), 3.90-3.73 (m, 2H), 3.69-3.62 (m, 3H).

LCMS: 407 (M+H$^+$) for C$_{17}$H$_{16}$—F$_2$N$_6$O$_4$.

EXAMPLE 106

Preparation of Compound 106

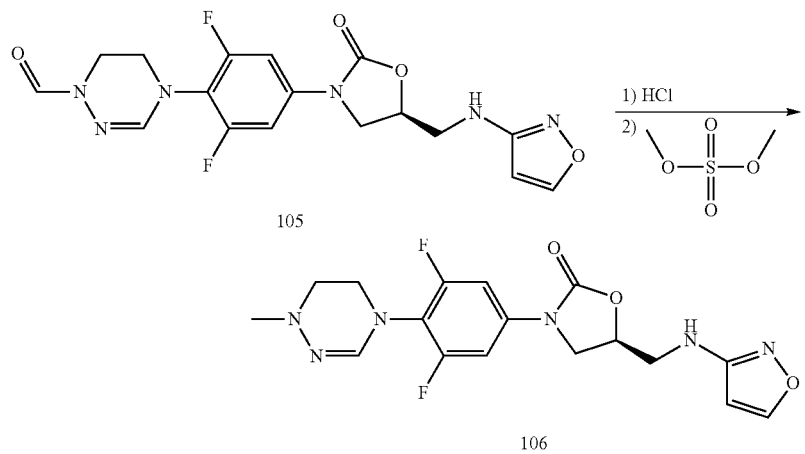

Compound 106 (24 mg, 0.061 mmol, 74%) was obtained from Compound 105 as in Example 89.

$^1$H NMR (400 MHz, CDCl$_3$) δ=8.06 (d, J=1.6 Hz, 1H), 7.23 (s, 1H), 7.18 (s, 1H), 6.65 (s, 1H), 5.90 (d, J=1.6 Hz, 1H), 4.99 (m, 1H), 4.92 (t, J=6.4 Hz, 1H), 4.06 (t, J=8.8 Hz, 1H), 3.89-3.61 (m, 5H), 3.00 (t, J=4.8 Hz, 2H).

LCMS: 393 (M+H$^+$) for C$_{17}$H$_{18}$—F$_2$N$_6$O$_3$.

TEST EXAMPLE 1

Measurement of in vitro Antibacterial Activity

In order to test the antibacterial activity of the oxazolidinone derivatives synthesized in Examples 1 to 106, in vitro activity test was carried out as followed.

In vitro antibacterial activity of the oxazolidinone derivatives of Examples 1 to 106 was evaluated by broth microdilution method, as compared with bacterial growth in the non-treated control group. Minimum inhibitory concentration of an antibiotic at which the growth of bacteria can be inhibited up to 90% (MIC$_{90}$, ug/mL) was measured. MIC$_{90}$ measurement was made according to the broth microdilution method based on the CLSI document [Clinical and Laboratory Standards Institute Document. (2000) Methods for Dilution Antimicrobial Susceptibility Test for Bacteria that Grow Aerobically—Fifth Edition: M7-A5. CLSI, Villanova, Pa.].

1) Test bacteriaAntibacterial activity was measured against 14 bacterial species including methicillin-susceptible *Staphylococcus aureus* (MSSA), methicillin-resistant *Staphylococcus aureus* (MRSA), vancomycin-resistant *Enterococcus* (VRE), linezolid- and vancomycin-resistant *Enterococcus faecalis* (LYRE), *Haemophilus influenzae* and *Moraxellacatarrhalis* (*S. aureus*, *S. aureus*$^{MR}$, *S. epidermidis*, *S. epidermidis*$^{MR}$, *E. faecalis*, *E. faecalis*$^{VanA}$, *E. faecalis*$^{VanALR}$, *E. faecium*$^{VanA}$, *E. faecium*, *E. coli*, *P. aeruginosa*, *K. pneumoniae*, *H. influenzae* and *M. catarrhalis*). The MIC$_{90}$ result against the most important two bacteria, MRSA and LYRE is given in Table 1.

2) Preparation of Test Compound

Test compounds (Compounds 1 to 106, i.e., the oxazolidinone derivatives synthesized in Examples 1 to 106) were dissolved in DMSO at the concentration of 10240 ug/mL and subjected to two-fold serial dilution with DMSO. The test compounds in DMSO solution were further diluted 20-fold with sterile distilled water. The final concentration of test compound in antibacterial incubations was from 0.0625 to 128 ug/mL. The final concentration of DMSO, which was used as an excipient, was 2.5% (v/v). Linezolid (Chemical Formula B) was used as a comparison compound. The results of antibacterial activity of test compounds are summarized in Table 1.

[Chemical Formula B]

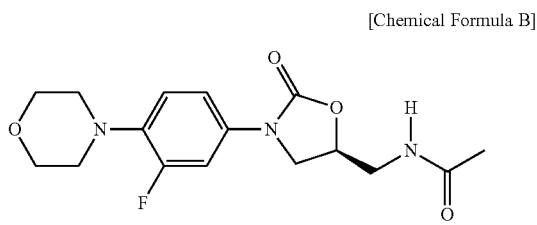

Accordingly, it is appreciated that the oxazolidinone derivatives of the present invention can be used as antibiotics having a broad antibacterial spectrum against Gram-positive bacteria.

TEST EXAMPLE 2

Measurement of Solubility in Water

Water solubilities of methanesulfonates (MSA) of representative compounds among the oxazolidinone derivatives of Chemical Formula 1 were measured. Linezolid of Chemical Formula B was used as a reference material. The results are given in Table 2.

Solubility measurement was done by $^1$H NMR according to the following method. First, a methanesulfonate (100 mg) of the compound was added to $D_2O$ (0.5 mL). After preparing a saturated solution by vigorous shaking for 30 minutes, the solution was filtered and 0.3 mL is taken therefrom. A reference compound solution (0.3 mL) (In this test example, DMSO diluted with $D_2O$ was used.) with an exactly known concentration was added thereto. From the $^1$H NMR spectrum of the solution, the integral ratio of the sample peak to the reference (DMSO) peak was calculated. Since the concentration of the reference solution is known, the mols of the

TABLE 1

Antibacterial activity (MIC$_{90}$, ug/mL) of compounds represented by Chemical Formula 1

| Cpd | MRSA[1] | LVRE[2] | Cpd | MRSA | LVRE | Cpd | MRSA | LVRE |
|---|---|---|---|---|---|---|---|---|
| Linezolid | 2 | 32 | 36 | 2 | 8 | 72 | 0.5 | 2 |
| 1 | 1 | 8 | 37 | 2 | 8 | 73 | 0.0625 | 2 |
| 2 | 2 | 16 | 38 | 4 | 8 | 74 | 0.25 | 2 |
| 3 | 2 | 8 | 39 | 2 | 8 | 75 | 0.25 | 2 |
| 4 | 1 | 8 | 40 | 2 | 8 | 76 | 0.5 | 2 |
| 5 | 1 | 8 | 41 | 2 | 4 | 77 | 0.5 | 4 |
| 6 | 2 | 8 | 42 | 8 | 32 | 78 | 0.5 | 4 |
| 7 | 1 | 8 | 43 | 2 | 32 | 79 | 8 | >64 |
| 8 | 4 | 16 | 44 | 8 | 64 | 80 | 2 | 16 |
| 9 | 0.5 | 8 | 45 | 1 | 4 | 81 | 1 | 16 |
| 10 | 4 | 32 | 46 | 2 | 16 | 82 | 2 | 32 |
| 11 | 1 | 8 | 47 | 2 | 8 | 83 | 1 | 16 |
| 12 | 2 | 8 | 48 | 4 | 16 | 84 | 0.5 | 16 |
| 13 | 4 | 16 | 49 | 1 | 8 | 85 | 0.5 | 16 |
| 14 | 2 | 8 | 50 | 2 | 16 | 86 | 0.5 | 8 |
| 15 | 4 | 8 | 51 | 1 | 4 | 87 | 0.5 | 8 |
| 16 | 128 | >128 | 52 | 2 | 16 | 88 | 0.5 | 8 |
| 17 | 1 | 8 | 53 | 0.5 | 8 | 89 | 0.5 | 8 |
| 18 | 4 | 16 | 54 | 0.5 | 4 | 90 | 2 | 8 |
| 19 | 0.5 | 4 | 55 | 2 | 8 | 91 | 0.5 | 8 |
| 20 | 16 | 64 | 56 | 4 | 8 | 92 | 1 | 64 |
| 21 | 2 | 4 | 57 | 0.25 | 2 | 93 | 1 | 32 |
| 22 | 16 | 128 | 58 | 0.25 | 4 | 94 | 1 | 64 |
| 23 | 32 | 64 | 59 | 0.5 | 2 | 95 | 1 | 16 |
| 24 | 2 | 16 | 60 | 0.25 | 2 | 96 | 2 | 16 |
| 25 | 4 | 32 | 61 | 0.5 | 4 | 97 | 0.5 | 8 |
| 26 | 16 | 64 | 62 | 0.0625 | 2 | 98 | 1 | 16 |
| 27 | 4 | 64 | 63 | 0.5 | 4 | 99 | 2 | 32 |
| 28 | 2 | 16 | 64 | 2 | 8 | 100 | 0.5 | 32 |
| 29 | 0.5 | 4 | 65 | 0.5 | 4 | 101 | 1 | 32 |
| 30 | 1 | 4 | 66 | 0.5 | 4 | 102 | 0.25 | 4 |
| 31 | 1 | 8 | 67 | 0.5 | 4 | 103 | 0.25 | 16 |
| 32 | 8 | 32 | 68 | 0.25 | 2 | 104 | 2 | 32 |
| 33 | 2 | 8 | 69 | 2 | 8 | 105 | 0.5 | 16 |
| 34 | 0.5 | 4 | 70 | 1 | 4 | 106 | 0.5 | 16 |
| 35 | 2 | 8 | 71 | 0.5 | 4 | | | |

[1] methicillin-resistant *Staphylococcus aureus*
[2] linezolid- and vancomycin-resistant *Enterococcus faecalis*

As seen from Table 1, the oxazolidinone derivatives of the present invention showed potent antibacterial activity against some Gram-positive bacteria resistant to existing antibiotics, such as methicillin-resistant *Staphylococcus aureus* and vancomycin-resistant *Enterococcus faecalis*, at much lower concentrations when compared to the comparator compound linezolid. Although not shown in Table 1, they were also effective against various Gram-positive bacteria, and some of them were effective against Gram-negative bacteria, such as *Haemophilus influenzae, Moraxella catarrhalis*. Especially, since they show excellent antibacterial activity against linezolid-resistant *Enterococcus faecalis*, they can be usefully used against linezolid-resistant bacteria, which are spreading nowadays.

sample can be calculated from the integral ratio. Then, the solubility of the sample was calculated.

TABLE 2

Solubility of methanesulfonate in water

| Compound | Linezolid | 83 | 89 | 94 |
|---|---|---|---|---|
| Solubility (mg/mL) | 3 | 117 | 129 | 136 |
| (% solubility) | (0.3%) | (12%) | (13%) | (14%) |

As seen from the table, the solubilities of the compounds represented by Chemical Formula 1 in water are greater than 10%, because they can be prepared as salts. In contrast, the solubility of the linezolid in water is only 0.3%. That is to say, the solubilities of the compounds of the present invention in water are up to 50 times higher than that of linezolid. This advantage allows the development of the compounds of the present invention into antibiotics that can be administered orally or intravenously as bolus, which is not feasible for linezolid. Further, since they are effective against linezolid-resistant bacteria, as well as MRSA and VRE, they can be developed into outstanding antibiotics capable of replacing linezolid.

TEST EXAMPLE 3

Cytotoxicity and MAO (Monoamine Oxidase) Inhibition

1) Cytotoxicity Measurement by MTT Assay

The MTT assay is a qualitative, colorimetric assay for mammalian cell survival and cell proliferation. It depends on the reduction of tetrazolium salt MTT by the mito-chondrial succinate dehrogenase of viable cells to form a blue formazan product. The assay measures cell respiration, and the amount of formazan product to the number of living cells present in culture. In this test, Chinese hamster ovary cells (CHO-K1) were purchased from ATCC (USA). Subcultured CHO cells were detached from the culture flask by treating with trypsin-EDTA solution, and seeded on a 96-well microplate, with 5000 cells per each well. After culturing for 24 hours in a 37° C., 5% $CO_2$ incubator, the cells were treated with the oxazolidinone derivatives according to the present invention synthesized in the above examples, at 7 different concentrations. After further culturing for 48 hours in a 37° C., 5% $CO_2$ incubator, 15 uL of 5 ug/mL MTT solution was added to each well. The cells were further incubated in the 37° C., 5% $CO_2$ incubator for about 2 hours. Then, the culture medium was discarded and 100 uL of DMSO solution was added to each well. After agitating the microplate for 30 minutes, absorbance was measured at 550 nm using Spectramax plus 190 plate reader (Molecular Devices, USA). The absorbance decrease of the compound-treated groups compared to the non-treated control group is an indication of the decrease of surviving cells, which enables the measurement of the cytotoxicity of the compounds. The $CC_{50}$ value, i.e., the concentration at which the cell proliferation is reduced to 50%, of the compounds according to the present invention was computed using the GraFit statistical analysis program (version 5.0.12) purchased from Erithacus Software after calculating the percentages of the absorbance at various concentrations as compared to the control group.

2) MAO Inhibition

Linezolid is known to act as a nonselective, reversible inhibitor of monoamine oxidases, and may possibly interact with adrenergic or serotonergic drugs. The oxazolidinone derivatives according to the present invention synthesized in the examples were tested for inhibition of monoamine oxidase A (MAO A) and monoamine oxidase B (MAO B). MAO-GLO assay kit was purchased from Promega (USA) and MAO A and MAO B enzymes were purchased from Sigma-Aldrich (USA). From the aldehyde product resulting from the action of the MAO enzyme on the amine group of the substrate, luciferin methyl ester is produced. The luciferin detection reagent is then added to inactivate the MAO enzymes. The esterase and the luciferase included in the reagent oxidize luciferin, thereby emitting light. The light emission is detected to measure the activity of MAO. The light emission was detected using LEADseeker (Amershan Bioscience, Sweden). MAO activity was measured in the presence of the compounds according to the present invention at 3.9-500 uM and compared with the non-treated control group. Linezolid was used as a comparison compound. For the measurement of the MAO inhibition activity of the compounds represented by Chemical Formula 1, the $IC_{50}$ value, i.e., the concentration of the compounds at which the enzymatic activity is inhibited by 50% (This value is related with the inhibition constant $K_i$), can be determined. The concentration of the inhibitor at which the rate of hydrolysis of the substrate is reduced to 50% (i.e., the $IC_{50}$ value) can be determined from a log plot of the relative rate of hydrolysis (as compared to the non-inhibited control group) versus the concentration of the compounds of Chemical Formula 1.

The MAO inhibition effect of the compounds of Chemical Formula 1 was measured by determining the inhibition constant $K_i$.

$$K_i = IC_{50}/\{1+([S]/K_m)\} \qquad \text{Equation 1}$$

In Equation 1, $K_m$ is the Michaelis-Menten constant, i.e., the concentration of the substrate at which the rate of enzymatic reaction is half of the maximum, and $IC_{50}$ is the concentration of the inhibitor at which the rate of the hydrolysis of the substrate is reduced by 50%. The $IC_{50}$ value was measured by plotting a log plot of the relative rate of hydrolysis (as compared to the non-inhibited control group) versus the concentration of the compounds of Chemical Formula 1. GraFit statistical analysis program (version 5.0.12) purchased from Erithacus Software was used.

Cytotoxicity test and MAO inhibition test results for representative compounds among the oxazolidinone derivatives of Chemical Formula 1 are given in Table 3.

Since the comparison compound linezolid exhibits significant inhibitory action against MAO enzymes and has the possibility of causing toxicity or other side effects, a lot of efforts has been made to find a compound with no MAO inhibition effect. In general, oxazolidinone-based compounds show such a strong MAO inhibition effect as to be used as MAO inhibitors. However, although the MAO inhibitor may provide a therapeutic effect for those who need it, it may result in toxicity or other side effects when it is used as an antibiotic. Accordingly, the determination of the MAO inhibition effect of oxazolidinone antibiotics is absolutely required, and one with less such effect is favored.

Linezolid and TR-700 of Chemical Formula D, developed by Trius Therapeutics, were used as comparison compounds. Since TR-701 is a prodrug of TR-700, TR-700 was used.

TABLE 3

| | $CC_{50}$ (uM) | MAOA (uM) | MAOB (uM) |
|---|---|---|---|
| Linezolid | >130 | 7.9 | 4.3 |
| TR-700 | 28 | <2.0 | 6.1 |
| 53 | >130 | 24 | 58 |
| 83 | >130 | 19 | 207 |
| 89 | >130 | 5.2 | >250 |
| 94 | >130 | 4 | 176 |
| 102 | >130 | 89 | 84 |

As seen from the table 3, TR-700 exhibits substantial amount of cytotoxic effect and potent inhibitory effect against MAO A and MAO B as well. In contrast, most of the compounds of the present invention are safe in terms of cytotoxicity and exhibit less inhibitory effect than TR-700 by 1/10.

Because the compounds of the present invention exhibit high solubility and good antibacterial activity with less toxicity, they are highly promising probable as next-generation antibiotics.

The present application contains subject matter related to Korean Patent Application No. 10-2008-0093712, filed in the Korean Intellectual Property Office on Sep. 24, 2008, the entire contents of which is incorporated herein by reference.

While the present invention has been described with respect to the specific embodiments, it will be apparent to those skilled in the art that various changes and modifications may be made without departing from the spirit and scope of the invention as defined in the following claims.

INDUSTRIAL APPLICABILITY

As described above, the novel oxazolidinone derivatives of the present invention exhibit an antibacterial spectrum against resistant bacteria including methicillin-resistant *Staphylococcus* (MRSA), a low toxicity, and a strong antibacterial activity against resistant bacteria to existing antibiotics, such as *Staphylococcus aureus* and *Enterococcus faecalis*, especially an excellent antibacterial activity against linezolid-resistant *Enterococcus faecalis*. Therefore, they can be usefully used as the 2nd generation oxazolidinone antibiotics. Further, the oxazolidinone derivatives with a cyclic amidoxime or cyclic amidrazone group according to the present invention can be easily prepared into formulation for oral administration or injection because they have higher solubility in water than other existing oxazolidinone compounds.

The invention claimed is:

1. A novel oxazolidinone derivative represented by Chemical Formula 1, an in vivo hydrolysable ester thereof, an in vivo hydrolysable phosphate ester thereof, an isomer thereof, or a pharmaceutically acceptable salt thereof:

[Chemical Formula 1]

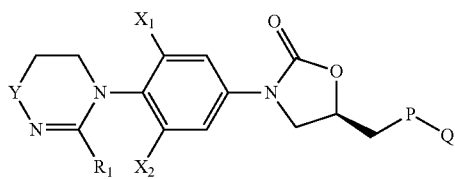

wherein $R_1$ represents hydrogen, $(C_1\text{-}C_6)$alkyl, or $(C_3\text{-}C_6)$cycloalkyl;

Y represents —O—, or —N($R_2$)—;

$R_2$ represents hydrogen, cyano, $(C_1\text{-}C_6)$alkyl, $(C_3\text{-}C_6)$cycloalkyl, —$(CH_2)_m$OC(=O)$R_{11}$, —$(CH_2)_m$C(=O)$R_{12}$, —$(CH_2)_m$C(=S)$R_{12}$, or —SO$_2$$R_{13}$, wherein the alkyl of $R_2$ may be further substituted by one or more substituent(s) selected from a group consisting of $(C_2\text{-}C_6)$alkenyl, $(C_2\text{-}C_6)$alkynyl, halogen, halo$(C_1\text{-}C_6)$alkyl, $(C_1\text{-}C_6)$alkyl$(C_2\text{-}C_6)$alkynyl, hydroxyl, $(C_3\text{-}C_6)$cycloalkyl and cyano;

$R_{11}$ through $R_{13}$ independently represent hydrogen, $(C_1\text{-}C_6)$alkyl, $(C_1\text{-}C_6)$alkoxy, amino, $(C_3\text{-}C_6)$cycloalkyl, $(C_2\text{-}C_6)$alkenyl, $(C_2\text{-}C_6)$alkynyl, or $(C_1\text{-}C_6)$alkylcarbonyl, wherein the alkyl, alkoxy or amino of $R_{11}$ through $R_{13}$ may be further substituted by one or more substituent(s) selected from halogen, amino, hydroxyl, cyano, $(C_1\text{-}C_6)$alkyl, $(C_1\text{-}C_6)$alkylcarbonyloxy and hydroxy $(C_1\text{-}C_6)$alkyl;

m represents an integer from 0 to 2;

$X_1$ and $X_2$ independently represent hydrogen or fluorine;

P represents —O—, —NH—, or a five-membered aromatic heterocycle with the following structure

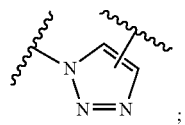

Q represents hydrogen, —C(=O)$R_3$, —C(=S)$R_4$, —C(=O)NR$_5$R$_6$, —C(=S)NR$_5$R$_6$, or a five-membered aromatic heterocycle with a structure selected from the followings:

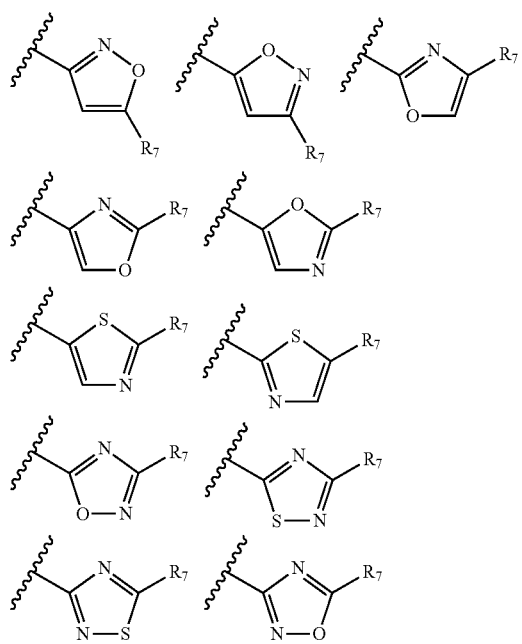

-continued

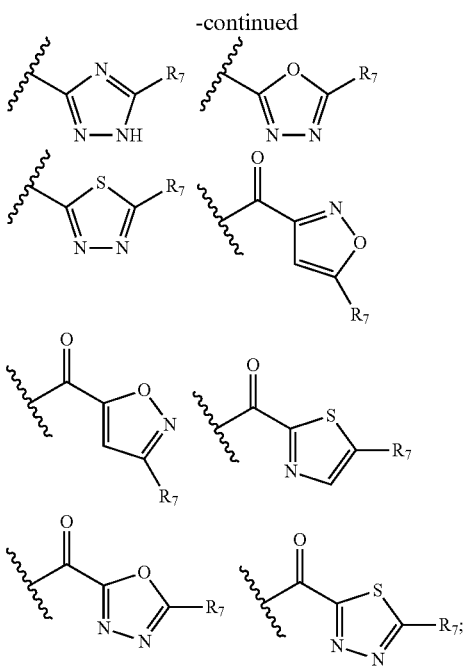

R$_3$ and R$_4$ independently represent hydrogen, (C$_1$-C$_6$)alkyl, (C$_1$-C$_6$)alkoxy, (C$_3$-C$_6$)cycloalkyl, (C$_2$-C$_6$)alkenyl, or (C$_2$-C$_6$)alkynyl;

R$_5$ and R$_6$ independently represent hydrogen, (C$_1$-C$_6$)alkyl, (C$_3$-C$_6$)cycloalkyl, or (C$_2$-C$_6$)alkenyl;

R$_7$ represents hydrogen, halogen, (C$_1$-C$_6$)alkyl, or (C$_3$-C$_6$)cycloalkyl; and the alkyl of R$_3$ through R$_7$ may be further substituted by one or more substituent(s) selected from a group consisting of hydroxyl, cyano, halogen, (C$_1$-C$_6$)alkylcarbonyloxy and amino.

2. The novel oxazolidinone derivative according to claim 1, which is represented by Chemical Formula 2 or 3, an in vivo hydrolysable ester thereof, an in vivo hydrolysable phosphate ester thereof, an isomer thereof, or a pharmaceutically acceptable salt thereof:

[Chemical Formula 2]

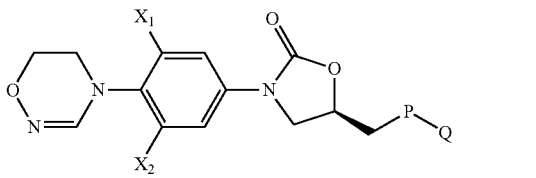

[Chemical Formula 3]

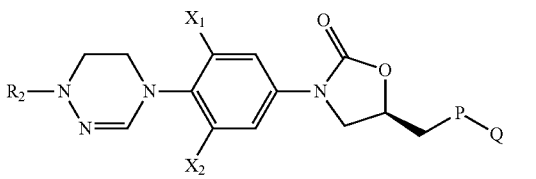

wherein R$_2$, X$_1$, X$_2$, P and Q are the same as defined in claim 1.

3. The novel oxazolidinone derivative according to claim 2, which is represented by Chemical Formula 4, 5, or 6, an in vivo hydrolysable ester thereof, an in vivo hydrolysable phosphate ester thereof, a hydrate thereof, an isomer thereof, or a pharmaceutically acceptable salt thereof:

[Chemical Formula 4]

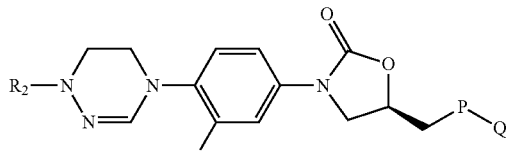

[Chemical Formula 5]

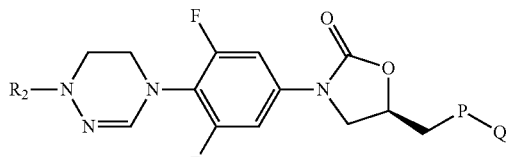

[Chemical Formula 6]

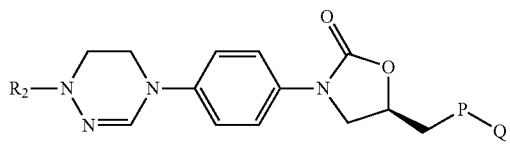

wherein

R$_2$ represents hydrogen, cyano, (C$_1$-C$_6$)alkyl, (C$_3$-C$_6$)cycloalkyl, —(CH$_2$)$_m$OC(=O)R$_{11}$, —(CH$_2$)$_m$C(=O)R$_{12}$, —(CH$_2$)$_m$C(=S)R$_{12}$, or —SO$_2$R$_{13}$, wherein the alkyl of R$_2$ may be further substituted by one or more substituent(s) selected from a group consisting of (C$_2$-C$_6$)alkenyl, (C$_2$-C$_6$)alkynyl, halogen, halo(C$_1$-C$_6$)alkyl, (C$_1$-C$_6$)alkyl(C$_2$-C$_6$)alkynyl, hydroxyl, (C$_3$-C$_6$)cycloalkyl and cyano;

R$_{11}$ through R$_{13}$ independently represent hydrogen, (C$_1$-C$_6$)alkyl, (C$_1$-C$_6$)alkoxy, amino, (C$_3$-C$_6$)cycloalkyl, or (C$_1$-C$_6$)alkylcarbonyl, and the alkyl, alkoxy, or amino of R$_{11}$ through R$_{13}$ may be further substituted by one or more substituent(s) selected from halogen, amino, hydroxyl, cyano, (C$_1$-C$_6$)alkyl, (C$_1$-C$_6$)alkylcarbonyloxy and hydroxy(C$_1$-C$_6$)alkyl;

m represents an integer from 0 to 2;

P represents —O—, —NH—, or a five-membered aromatic heterocycle with the following structure

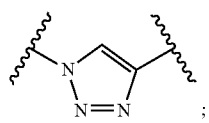

;

Q represents hydrogen, —C(=O)R$_3$, —C(=S)R$_4$, —C(=O)NR$_5$R$_6$, —C(=S)NR$_5$R$_6$, or a five-membered aromatic heterocycle with a structure selected from the followings:

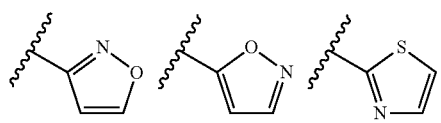

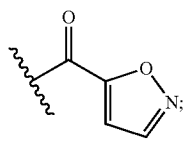

R$_3$ and R$_4$ independently represent hydrogen, (C$_1$-C$_6$)alkyl, or (C$_1$-C$_6$)alkoxy;

R$_5$ and R$_6$ independently represent hydrogen, or (C$_1$-C$_6$)alkyl; and the alkyl of R$_3$ through R$_6$ may be further substituted by one or more substituent(s) selected from a group consisting of hydroxyl, cyano, halogen, (C$_1$-C$_6$)alkylcarbonyloxy and amino.

4. The novel oxazolidinone derivative according to claim 2, which is represented by Chemical Formula 7, 8, or 9, an in vivo hydrolysable ester thereof, an in vivo hydrolysable phosphate ester thereof, an isomer thereof, or a pharmaceutically acceptable salt thereof:

[Chemical Formula 7]

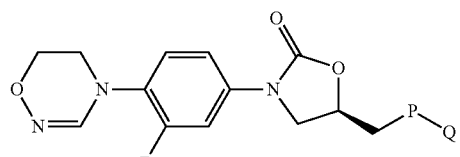

[Chemical Formula 8]

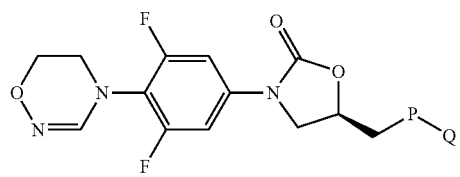

[Chemical Formula 9]

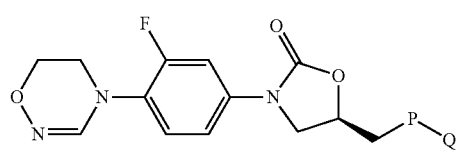

wherein

P represents —O—, —NH—, or a five-membered aromatic heterocycle with the following structure

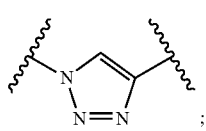

Q represents hydrogen, —C(=O)R$_3$, —C(=S)R$_4$, —C(=O)NR$_5$R$_6$, —C(=S)NR$_5$R$_6$, or a five-membered aromatic heterocycle with a structure selected from the followings:

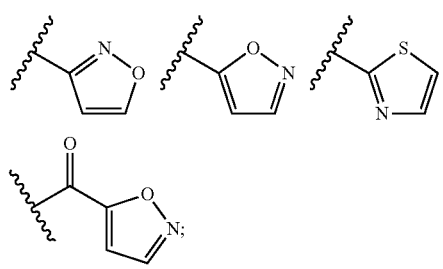

R$_3$ and R$_4$ independently represent hydrogen, (C$_1$-C$_6$)alkyl, or (C$_1$-C$_6$)alkoxy;

R$_5$ and R$_6$ independently represent hydrogen, or (C$_1$-C$_6$)alkyl; and the alkyl of R$_3$ through R$_6$ may be further substituted by one or more substituent(s) selected from a group consisting of hydroxyl, cyano, halogen, (C$_1$-C$_6$)alkylcarbonyloxy and amino.

5. The novel oxazolidinone derivative according to claim 3, which is selected from the following compounds, an in vivo hydrolysable ester thereof, an in vivo hydrolysable phosphate ester thereof, an isomer thereof, or a pharmaceutically acceptable salt thereof:

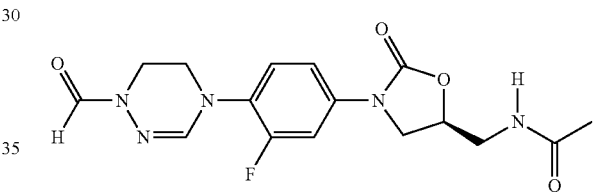

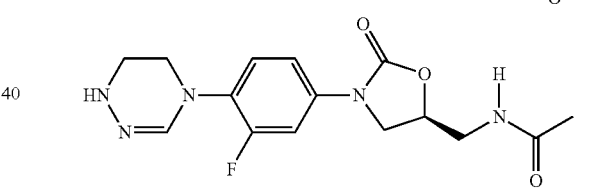

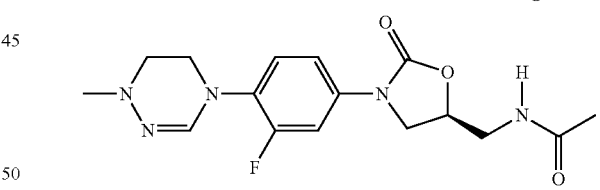

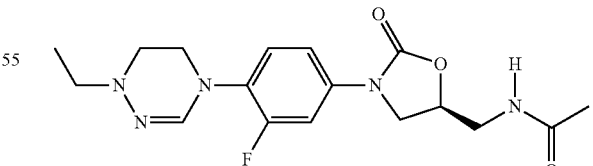

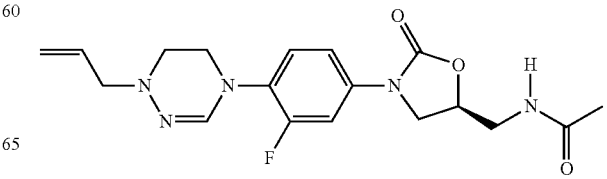

125
-continued
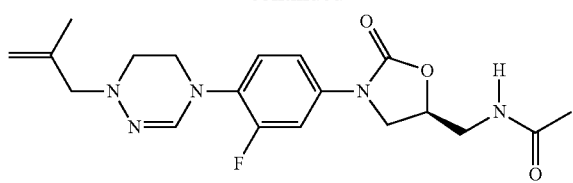
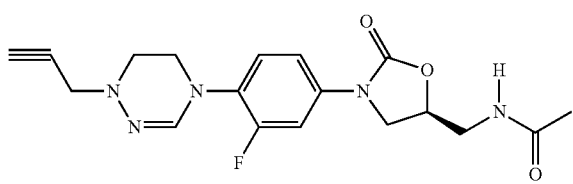
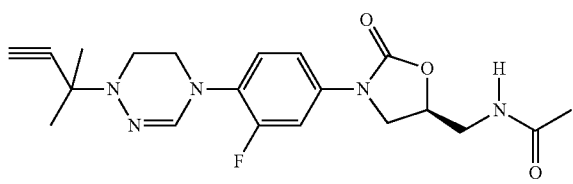
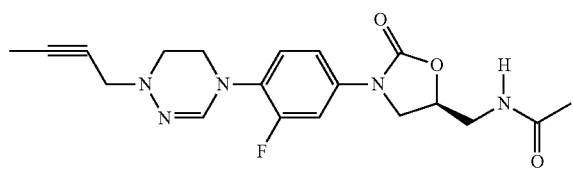
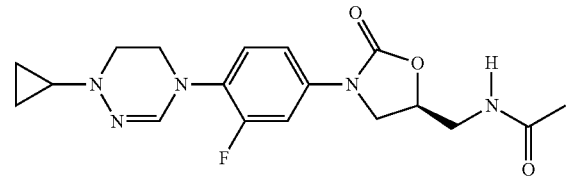
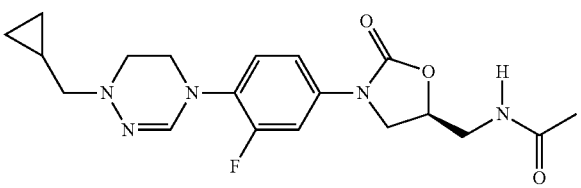
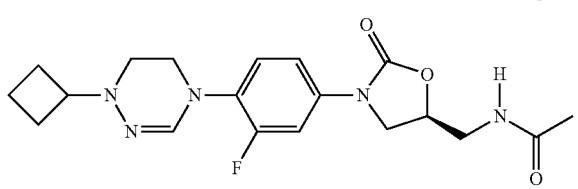
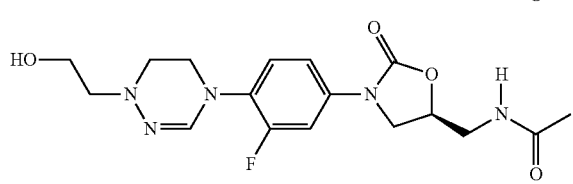
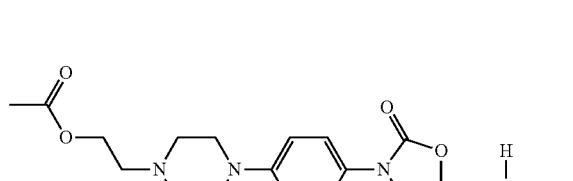
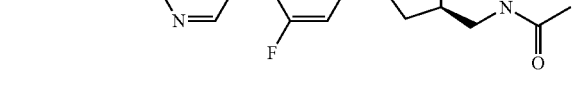
126
-continued
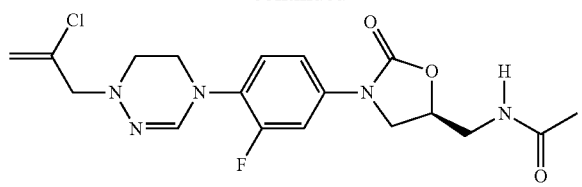
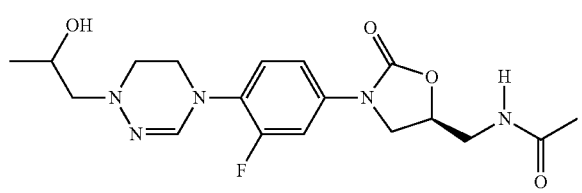
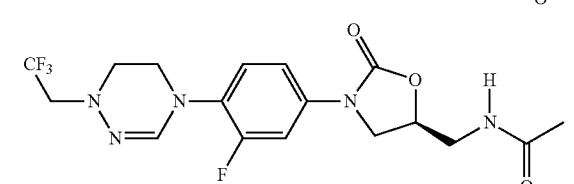
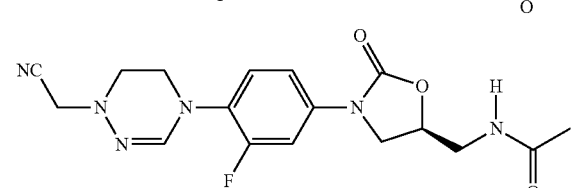
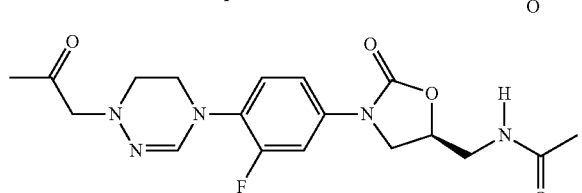
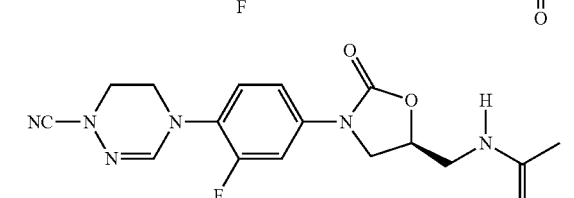
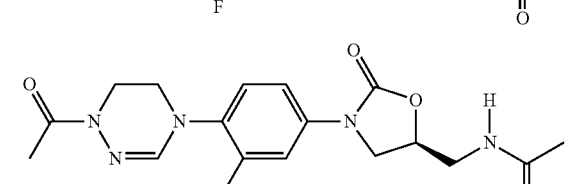
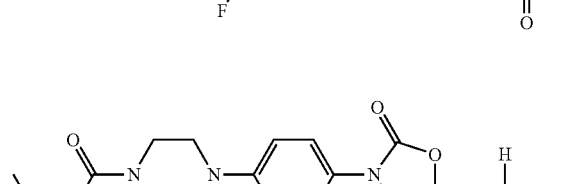
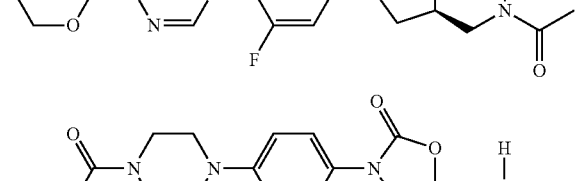
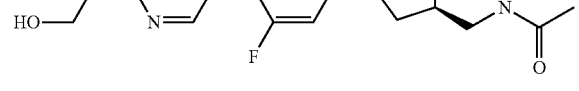

127
-continued
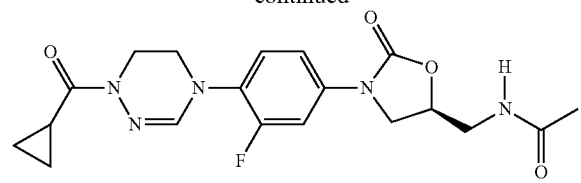
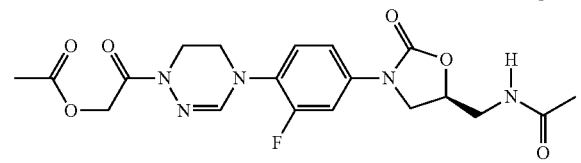
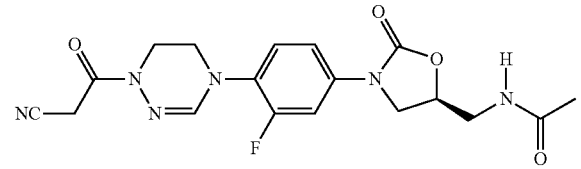
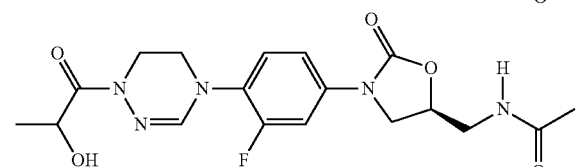
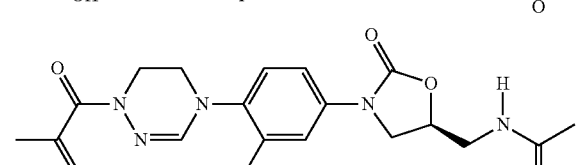
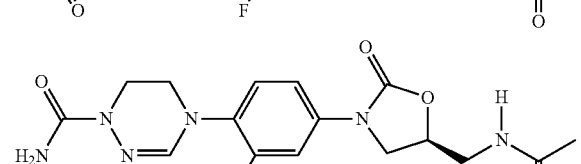
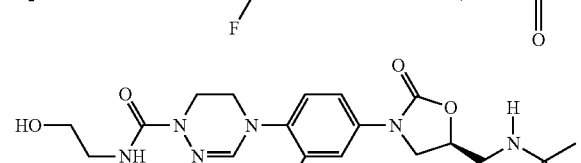
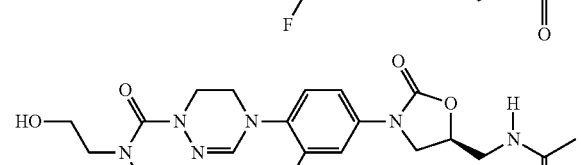
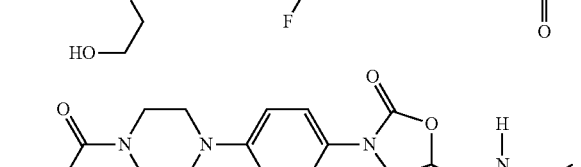
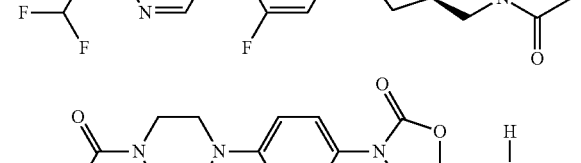
128
-continued
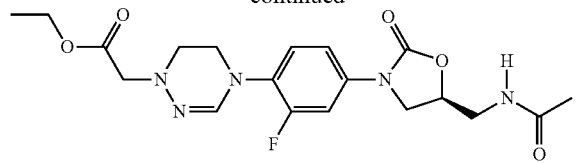
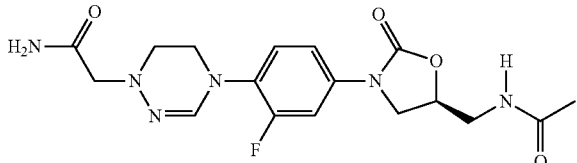
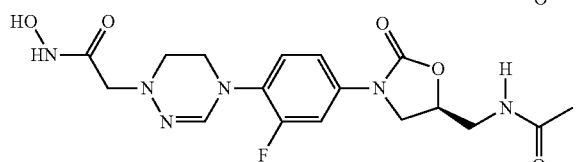
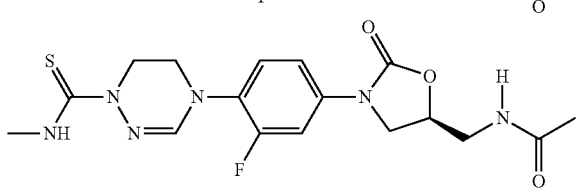
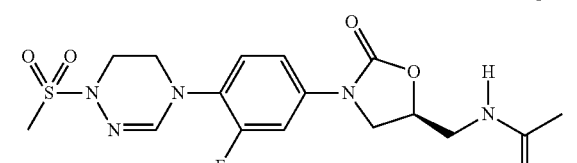
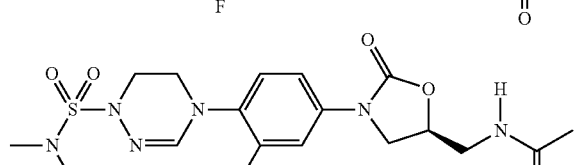
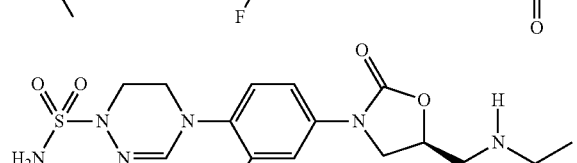
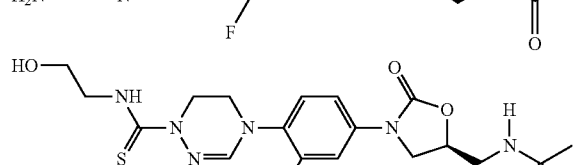
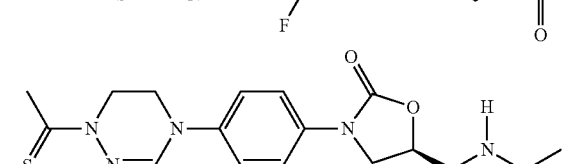
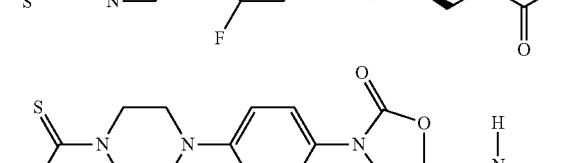

129
-continued

130
-continued

131
-continued

132
-continued

133
-continued
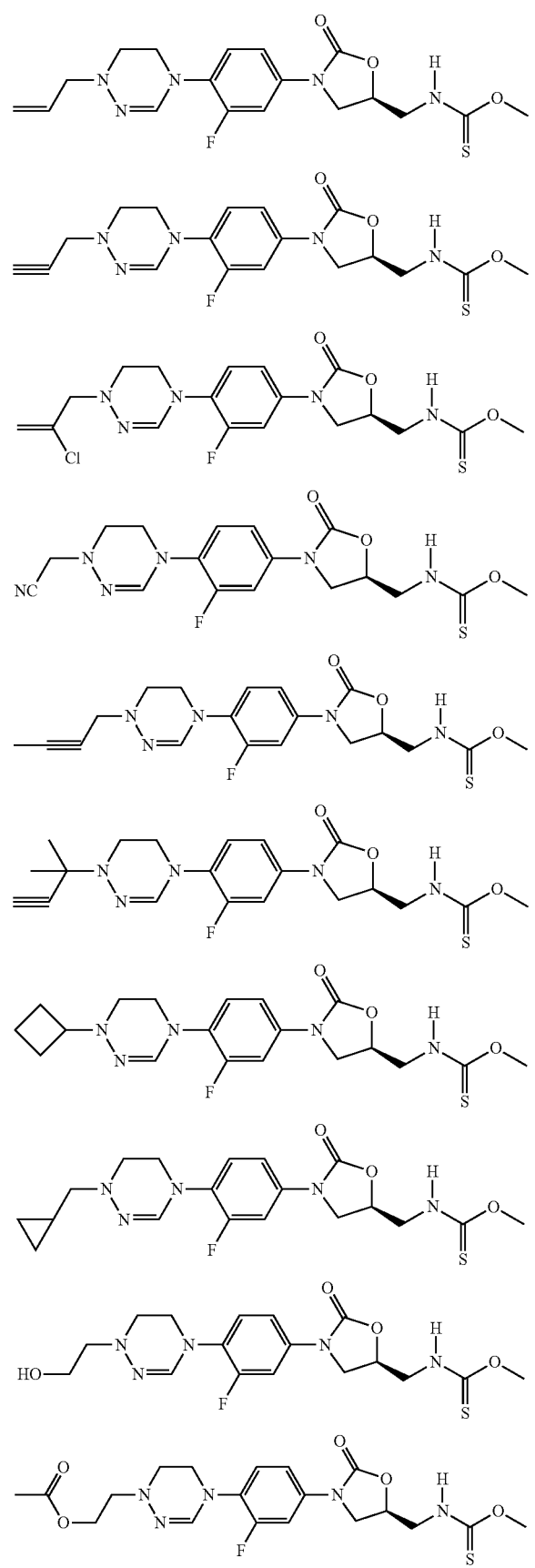
134
-continued
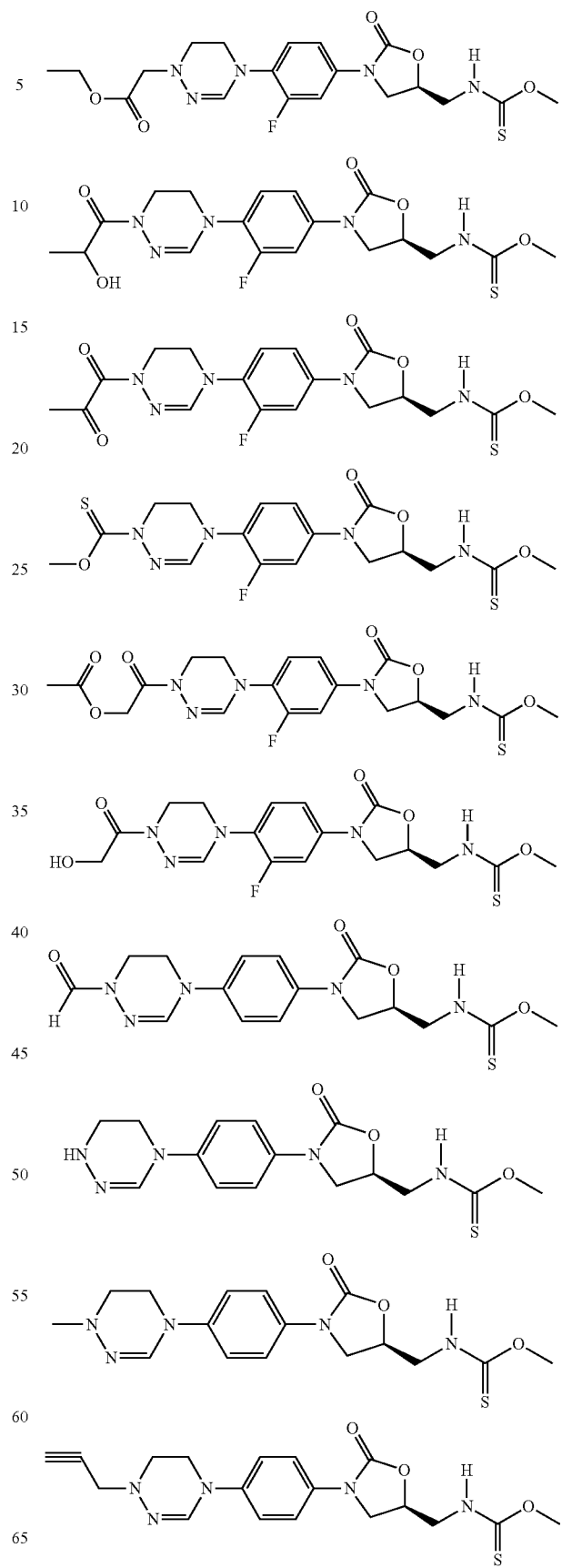

135
-continued
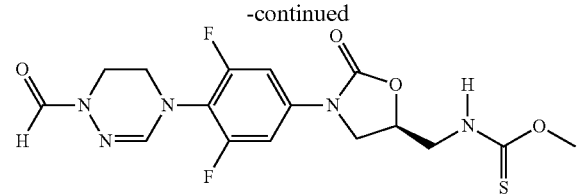
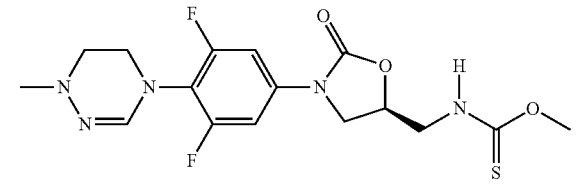
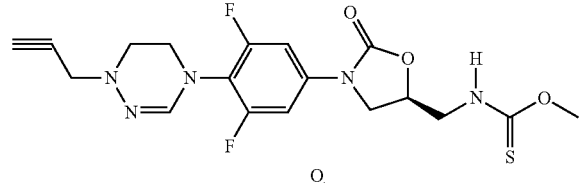
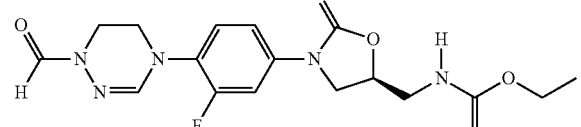
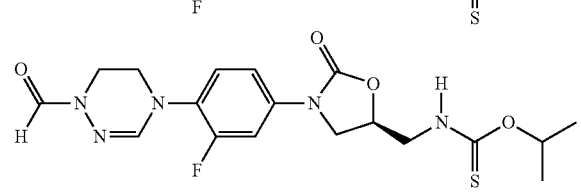
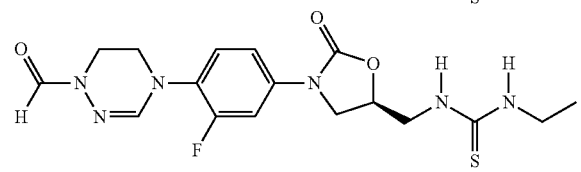
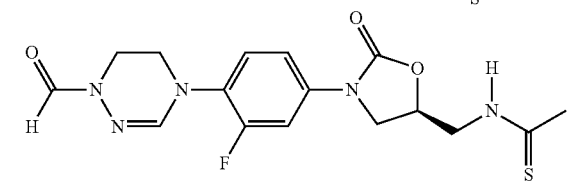
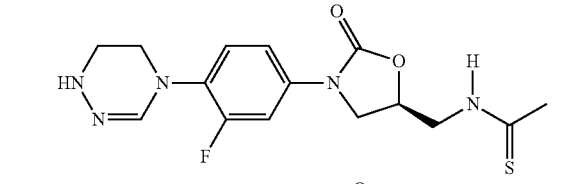
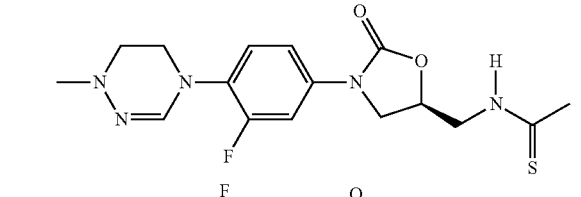
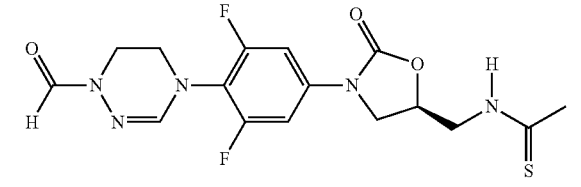
136
-continued
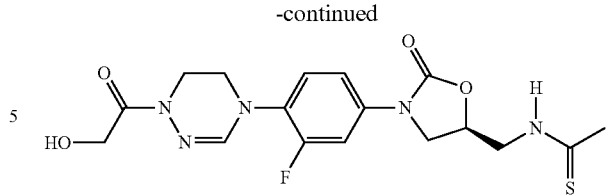
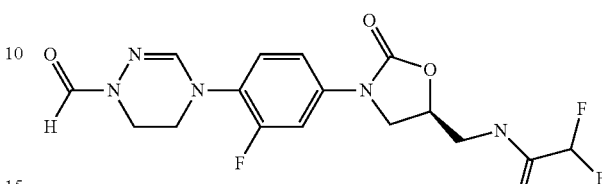
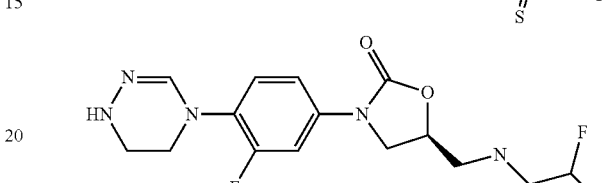
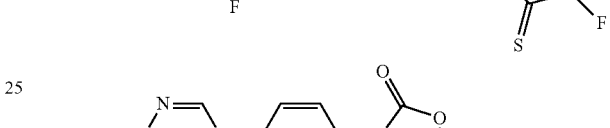
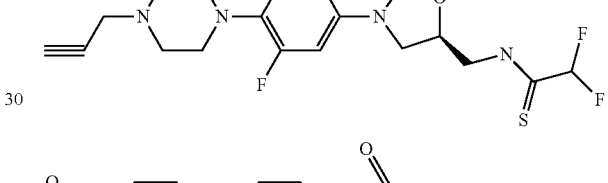
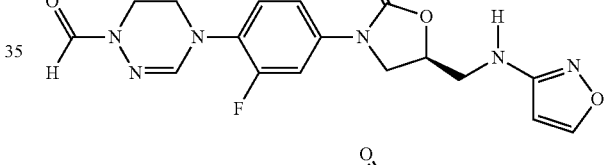
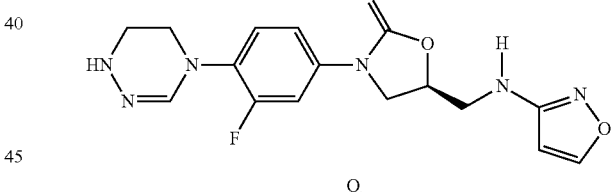
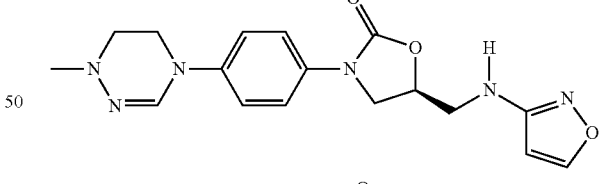
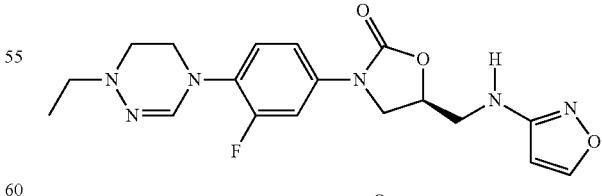
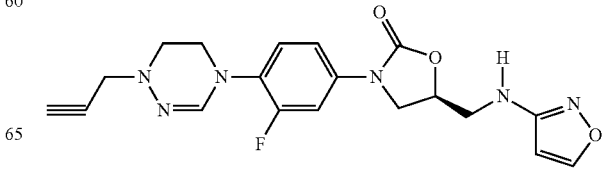

137
-continued
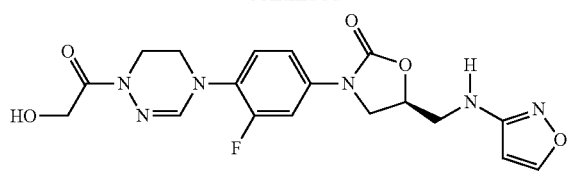
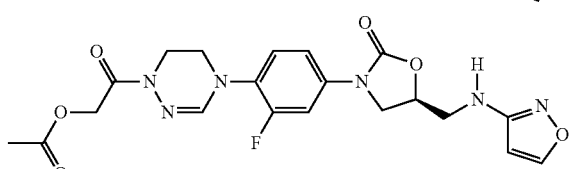
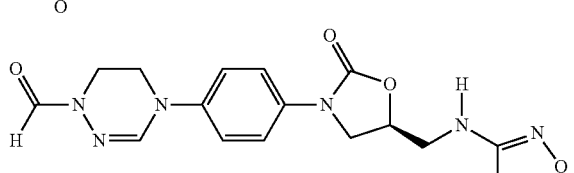
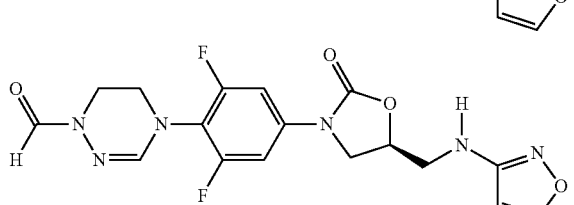
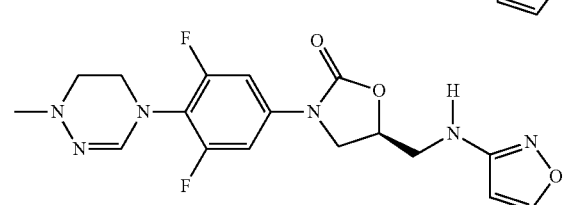
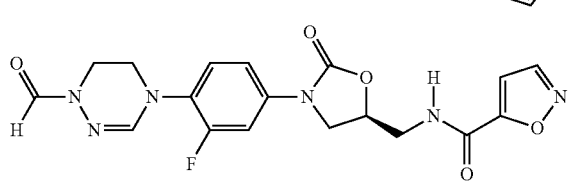
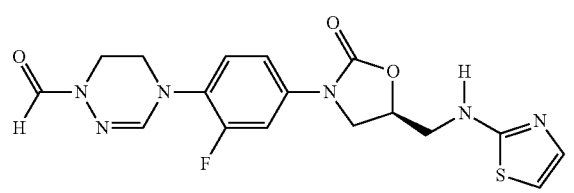
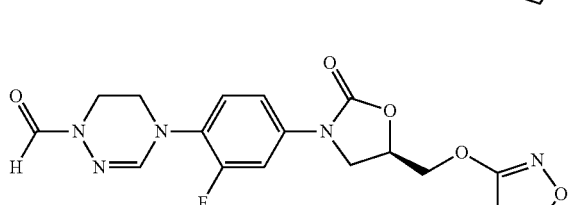
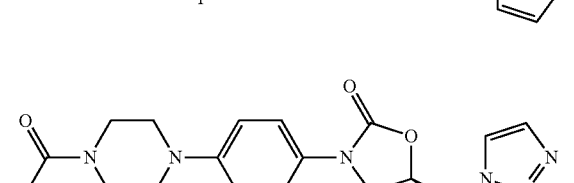
138
-continued
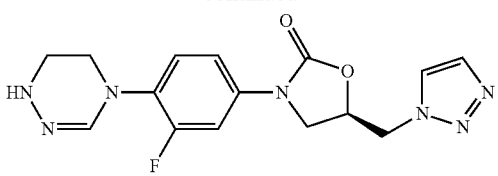
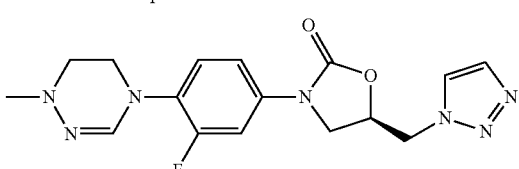
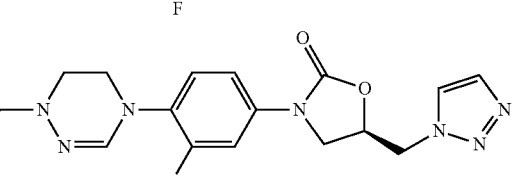
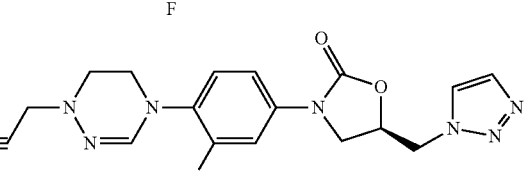
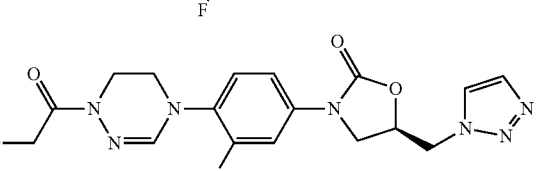
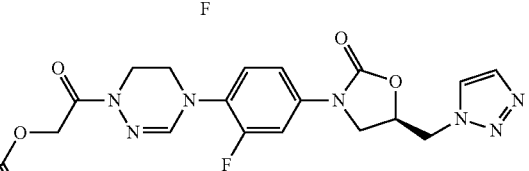
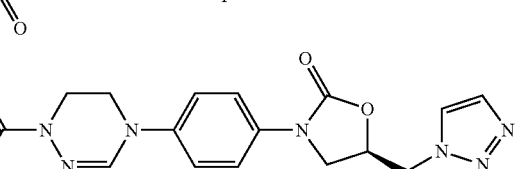
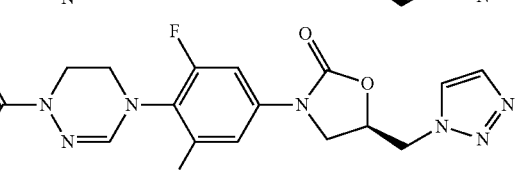
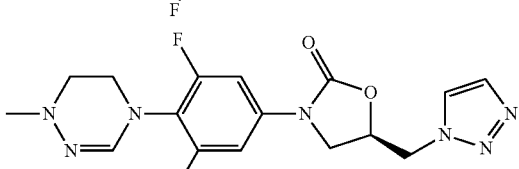
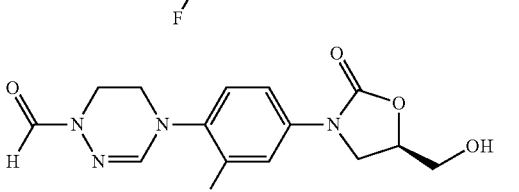

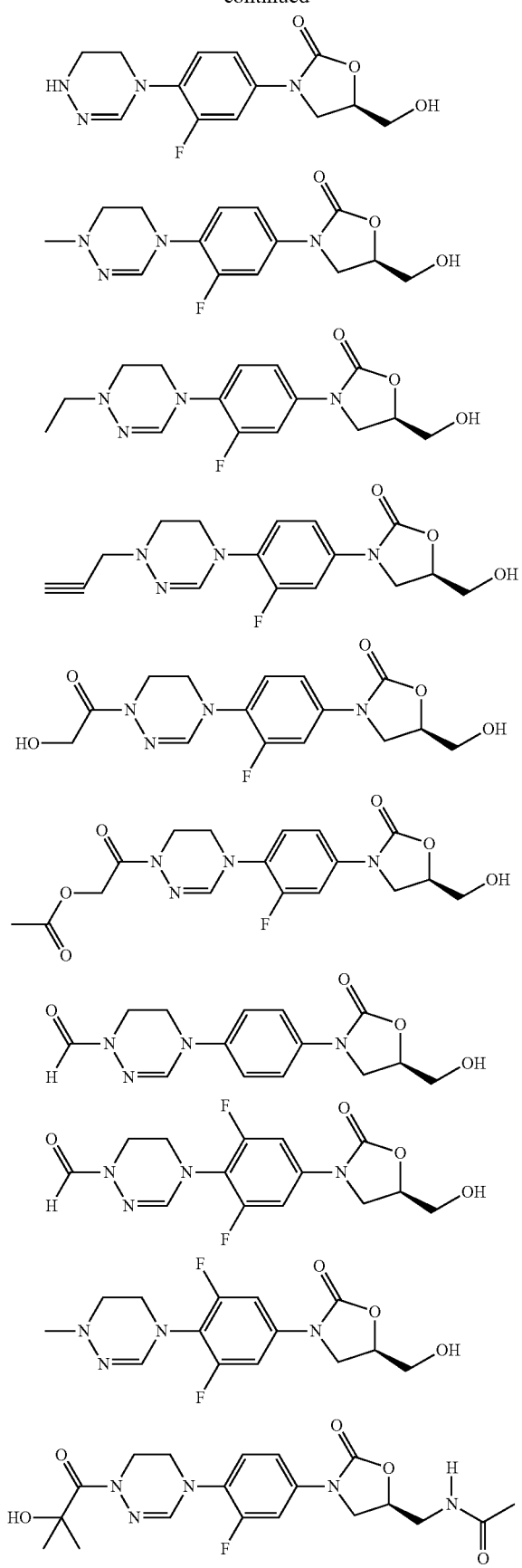
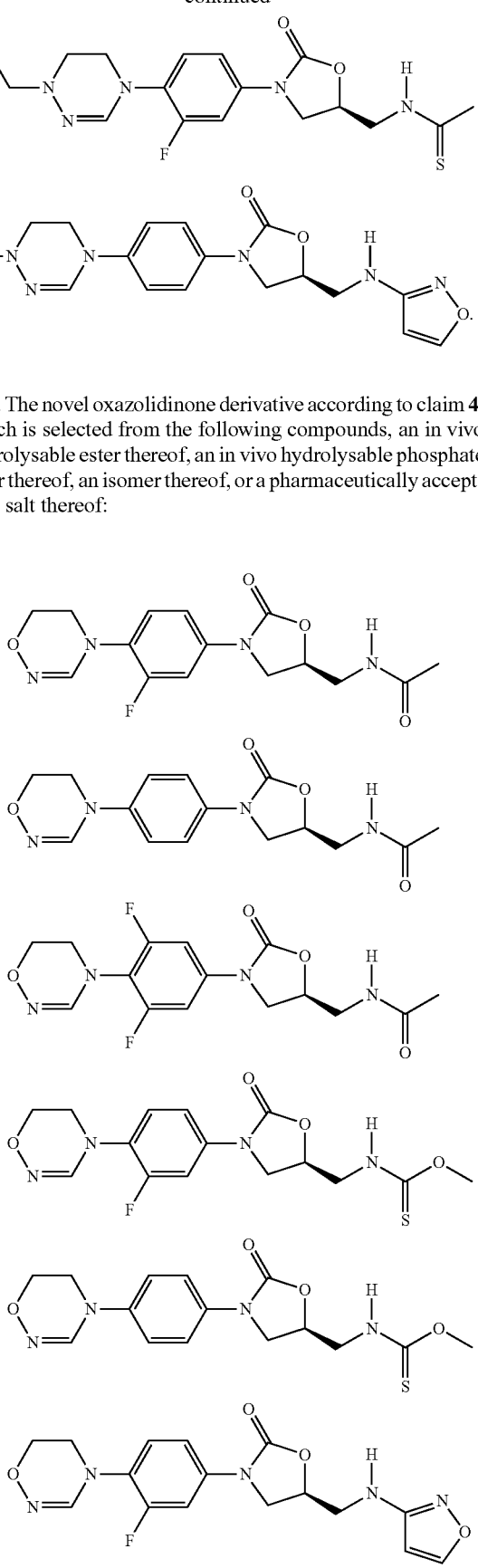
6. The novel oxazolidinone derivative according to claim 4, which is selected from the following compounds, an in vivo hydrolysable ester thereof, an in vivo hydrolysable phosphate ester thereof, an isomer thereof, or a pharmaceutically acceptable salt thereof:

-continued

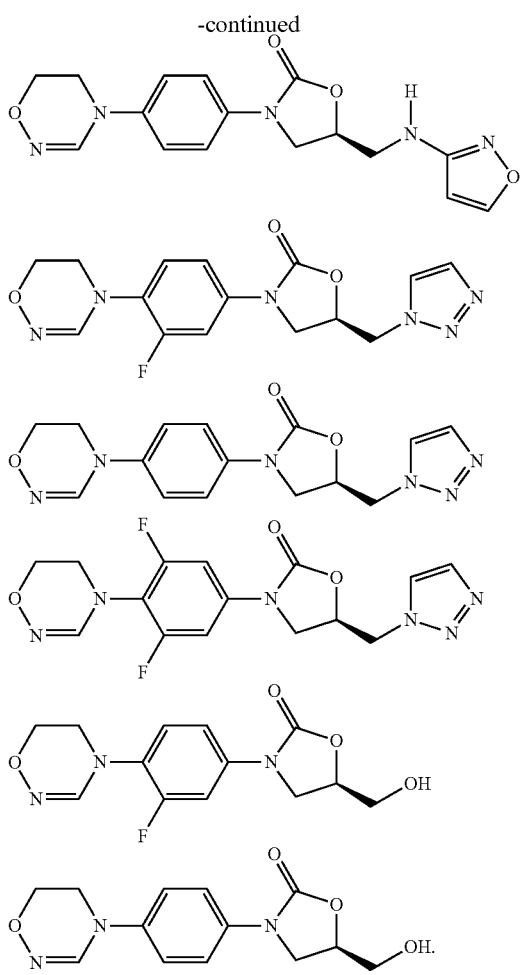

7. A pharmaceutical composition comprising the novel oxazolidinone derivative according to claim 1, an in vivo hydrolysable ester thereof, an in vivo hydrolysable phosphate ester thereof, an isomer thereof, or a pharmaceutically acceptable salt thereof, as an effective ingredient.

8. A pharmaceutical composition comprising the novel oxazolidinone derivative according to claim 2, an in vivo hydrolysable ester thereof, an in vivo hydrolysable phosphate ester thereof, an isomer thereof, or a pharmaceutically acceptable salt thereof, as an effective ingredient.

9. A pharmaceutical composition comprising the novel oxazolidinone derivative according to claim 3, an in vivo hydrolysable ester thereof, an in vivo hydrolysable phosphate ester thereof, an isomer thereof, or a pharmaceutically acceptable salt thereof, as an effective ingredient.

10. A pharmaceutical composition comprising the novel oxazolidinone derivative according to claim 4, an in vivo hydrolysable ester thereof, an in vivo hydrolysable phosphate ester thereof, an isomer thereof, or a pharmaceutically acceptable salt thereof, as an effective ingredient.

11. A pharmaceutical composition comprising the novel oxazolidinone derivative according to claim 5, an in vivo hydrolysable ester thereof, an in vivo hydrolysable phosphate ester thereof, an isomer thereof, or a pharmaceutically acceptable salt thereof, as an effective ingredient.

12. A pharmaceutical composition comprising the novel oxazolidinone derivative according to claim 6, an in vivo hydrolysable ester thereof, an in vivo hydrolysable phosphate ester thereof, an isomer thereof, or a pharmaceutically acceptable salt thereof, as an effective ingredient.

13. A method of treating a bacterial infection in a subject, comprising administering to the subject the novel oxazolidinone derivative according to claim 1.

14. A method of treating a bacterial infection in a subject, comprising administering to the subject the novel oxazolidinone derivative according to claim 2.

15. A method of treating a bacterial infection in a subject, comprising administering to the subject the novel oxazolidinone derivative according to claim 3.

16. A method of treating a bacterial infection in a subject, comprising administering to the subject the novel oxazolidinone derivative according to claim 4.

17. A method of treating a bacterial infection in a subject, comprising administering to the subject the novel oxazolidinone derivative according to claim 5.

18. A method of treating a bacterial infection in a subject, comprising administering to the subject the novel oxazolidinone derivative according to claim 6.

19. The method of claim 1, wherein the bacterial infection results from a Gram-positive bacterium.

20. The method of claim 1, wherein the bacterial infection results from a Gram-negative bacterium.

21. The method of claim 13, wherein the Gram-positive bacterium is selected from the group consisting of *Staphylococcus, Enterococcus, Streptococcus* and acid-fast bacteria.

22. The method of claim 13, wherein the Gram-negative bacterium is selected from the group consisting of *Haemophilus influenzae, Moraxella catarrhalis* and *Staphylococcus*.

* * * * *